United States Patent
Hoffmann et al.

(10) Patent No.: US 9,035,026 B2
(45) Date of Patent: May 19, 2015

(54) ANTI-CD16 BINDING MOLECULES

(75) Inventors: Karin Hoffmann, Schwetzingen (DE); Sergey Kipriyanov, Heidelberg (DE); Stefan Knackmuss, Plankstadt (DE); Fabrice Le Gall, Edingen-Neckarhausen (DE); Melvyn Little, Neckargemünd (DE); Uwe Reusch, Maikammer (DE)

(73) Assignee: Affimed GMBH, Heidelberg (DE)

( * ) Notice: Subject to any disclaimer, the term of this patent is extended or adjusted under 35 U.S.C. 154(b) by 1195 days.

(21) Appl. No.: 11/921,123

(22) PCT Filed: May 26, 2006

(86) PCT No.: PCT/EP2006/005057
§ 371 (c)(1),
(2), (4) Date: Mar. 13, 2009

(87) PCT Pub. No.: WO2006/125668
PCT Pub. Date: Nov. 30, 2006

(65) Prior Publication Data
US 2009/0214574 A1 Aug. 27, 2009

(30) Foreign Application Priority Data
May 26, 2005 (GB) .................................. 0510790.9

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| C07K 16/28 | (2006.01) |
| A61K 47/48 | (2006.01) |
| C07K 17/00 | (2006.01) |

(52) U.S. Cl.
CPC ......... *C07K 16/283* (2013.01); *A61K 47/48676* (2013.01); *C07K 16/2878* (2013.01); *C07K 2317/31* (2013.01); *C07K 2317/622* (2013.01); *C07K 2317/732* (2013.01); *C07K 2317/92* (2013.01); *C07K 2319/30* (2013.01); *C07K 2317/34* (2013.01)

(58) Field of Classification Search
None
See application file for complete search history.

(56) References Cited

U.S. PATENT DOCUMENTS

| | | | | |
|---|---|---|---|---|
| 4,281,061 | A | * | 7/1981 | Zuk et al. .................. 435/7.9 |
| 5,770,195 | A | | 6/1998 | Hudziak et al. |
| 5,968,511 | A | | 10/1999 | Akita et al. |
| 6,033,876 | A | | 3/2000 | Lemke et al. |
| 6,132,992 | A | * | 10/2000 | Ledbetter et al. ............ 435/69.7 |
| 6,699,473 | B2 | | 3/2004 | Raisch et al. |
| 7,351,803 | B2 | * | 4/2008 | Johnson et al. ............. 530/387.1 |

FOREIGN PATENT DOCUMENTS

| | | |
|---|---|---|
| EP | 0429242 B1 | 6/1995 |
| EP | 0502812 B1 | 8/1996 |
| EP | 1005870 A2 | 6/2000 |
| EP | 1005870 A3 | 10/2002 |
| EP | 1314741 B1 | 3/2007 |
| WO | WO 86/03223 A1 | 6/1986 |
| WO | WO 88/05054 A1 | 7/1988 |
| WO | WO 98/50433 A2 | 11/1998 |
| WO | WO 98/50433 A3 | 2/1999 |
| WO | WO 01/92340 A2 | 12/2001 |
| WO | WO 01/92340 A3 | 4/2002 |
| WO | WO 02/053596 A2 | 7/2002 |
| WO | WO 03/025018 A2 | 3/2003 |
| WO | WO 03/030835 A2 | 4/2003 |
| WO | WO 03/035904 A2 | 5/2003 |
| WO | WO 03/025018 A3 | 8/2003 |
| WO | WO 03/030835 A3 | 10/2003 |
| WO | WO 03/035904 A3 | 10/2003 |
| WO | WO 03/101485 A1 | 12/2003 |
| WO | WO 02/053596 A3 | 1/2004 |
| WO | WO 2004/071529 A2 | 8/2004 |
| WO | WO 2004/106383 A1 | 12/2004 |
| WO | WO 2004/071529 A3 | 5/2005 |

OTHER PUBLICATIONS

Rudikoff et al. PNAS 1982 vol. 79, pp. 1979-1983.*
Rader et al. PNAS. 1998. 95:8910-8915.*
SEQ ID No. 18 alignment. May 19, 2011. pp. 1-68.*
SEQ ID No. 35 alignment. May 19, 2011. pp. 1-2.*
Sleister et al. Journal of Immunological Methods 261 (2002) 213-220.*
Kipriyanov et al. J. Immunol 2002;169;137-144.*
Dörsam et al. FEBS Letters 1997, 414:7-13.*
Altuvia, et al. Ranking potential binding peptides to MHC molecules by a computational threading approach. J. Mol. Biol. 1995; 249:244-2450.
Anderson, et al. Fc gamma receptor type III (CD16) is included in the zeta NK receptor complex expressed by human natural killer cells. PNAS. 1990; 87(6):2274-2278.
Arndt, et al. A bispecific diabody that mediates natural killer cell cytotoxicity against xenotransplantated human Hodgkin's tumors. Blood. 1999; 94:2562-2568.
Bander, et al. Targeted systemic therapy of prostate cancer with a monoclonal antibody to prostate-specific membrane antigen. Semin. Oncol. 2003; 30:667-677.
Buto, et al., Production and characterization of monoclonal antibodies directed against the laminin receptor precursor.1997, Int. J. Biol. Markers 12:1-5 (abstract).

(Continued)

*Primary Examiner* — Chun Dahle
(74) *Attorney, Agent, or Firm* — Perkins Coie LLP; Viola T. Kung

(57) ABSTRACT

The present invention relates to binding molecules that specifically bind to the human Fc gamma receptor expressed on the surface of natural killer (NK) cells and macrophages (i.e. FcγRIIIA), and in particular binding molecules that specifically bind the A form FcγRIII but do not bind to the B form of FcγRIII, as well as to the use of such binding molecules in the diagnosis and treatment of disease. The invention further extends to polynucleotides encoding such binding molecules, host cells comprising such polynucleotides and methods of producing binding molecules of the invention using such host cells.

21 Claims, 9 Drawing Sheets

(56) References Cited

OTHER PUBLICATIONS

Carter, et al. Humanization of an anti-p185HER2 antibody for human cancer therapy. Proc Natl Acad Sci U S A. May 15, 1992;89(10):4285-9.
Chesla, et al. The membrane anchor influences ligand binding two-dimensional kinetic rates and three-dimensional affinity of FcgammaRIII (CD16). J Biol Chem. Apr. 7, 2000;275(14):10235-46.
Cochlovius, et al. Cure of Burkitt's lymphoma in severe combined immunodeficiency mice by T cells, tetravalent CD3 × CD19 tandem diabody, and CD28 costimulation. Cancer Res. 2000; 60:4336-4341.
Cooper, et al. The biology of human natural killer-cell subsets. Trends Immunol. 2001; 22:633-640.
Dahlenborg, et al. Human monoclonal antibodies specific for the tumour associated Thomsen-Friedenreich antigen. Int. J. Cancer. 1997; 70:63-71.
Dörsam, et al. Antibodies to steroids from a small human naive IgM library. FEBS Lett. Sep. 1, 1997;414(1):7-13.
Dreier, et al. Extremely potent, rapid and costimulation-independent cytotoxic T-cell response against lymphoma cells catalyzed by a single-chain bispecific antibody. Int. J. Cancer. 2002; 100:690-697.
Gessner, et al. The human low affinity immunoglobulin G Fc receptor III-A and III-B genes. Molecular characterization of the promoter regions. J Biol Chem. Jan. 20, 1995;270(3):1350-61.
Hermanson, G.T. Bioconjugate Techniques. Academic Press, London, 1996, for standard methodologies relating to the use of cross-linking reagents.
Hombach, et al. A CD16/CD30 bispecific monoclonal antibody induces lysis of Hodgkin's cells by unstimulated natural killer cells in vitro and in vivo. Int. J. Cancer. 1993; 55:830-836.
Huizinga, et al. Biallelic neutrophil Na-antigen system is associated with a polymorphism on the phospho-inositol-linked Fc gamma receptor III (CD16). Blood. 1990; 75:213-7.
Kipriyanov, et al. Bispecific tandem diabody for tumor therapy with improved antigen binding and pharmacokinetics. J. Mol. Biol. 1999; 293:41-56.
Kipriyanov, et al., Recent advances in the generation of bispecific antibodies for tumor immunotherapy. 2004, Curr. Opin. Drug Discov. Devel., 7:233-242.
Koene, et al. Fc gamma RIIIB gene duplication: evidence for presence and expression of three distinct Fc gamma RIIIB genes in NA(1+,2+)SH(+) individuals. Blood. 1998; 91:673-679.
Koene, et al. Fc gammaRIIIa-158V/F polymorphism influences the binding of IgG by natural killer cell Fc gammaRIIIa, independently of the Fc gammaRIIIa-48L/R/H phenotype. Blood. 1997; 90:1109-1114.
Le Gall, et al. Immunosuppressive properties of anti-CD3 single-chain Fv and diabody. J. Immunol. Methods. 2004; 285:111-127.
Le Gall, et al. Di-, tri- and tetrameric single chain Fv antibody fragments against human CD19: effect of valency on cell binding. FEBS Letts. 1999; 453:164-168.
Li, et al. Recombinant CD16A-Ig forms a homodimer and cross-blocks the ligand binding functions of neutrophil and monocyte Fcgamma receptors. Mol Immunol. Jan. 2001;38(7):527-38.
Little, et al. Generation of a large complex antibody library from multiple donors. J. Immunol. Methods. 1999; 231:3-9.
Mandelboim, et al. Recognition of haemagglutinins on virus-infected cells by NKp46 activates lysis by human NK cells. Nature. 2001; 409:1055-1060.
Mandelboim, et al. Human CD16 as a lysis receptor mediating direct natural killer cell cytotoxicity. PNAS. 1999; 96:5640-5644.
Marvin, et al., Recombinant approaches to IgG-like bispecific antibodies. 2005, Acta Pharmacol. Sin., 26:649-658.

McCall, et al. Increasing the affinity for tumor antigen enhances bispecific antibody cytotoxicity. J. Immunol. 2001;166:6112-6117.
Nagarajan, et al. Ligand binding and phagocytosis by CD16 (Fc gamma receptor III) isoforms. Phagocytic signaling by associated zeta and gamma subunits in Chinese hamster ovary cells. J Biol Chem. Oct. 27, 1995;270(43):25762-70.
Nanus, et al. Clinical use of monoclonal antibody HuJ591 therapy: targeting prostate specific membrane antigen. 2003, J. Urol., 170:S84-S88.
Nouri, et al. A new highly specific monoclonal antibody against placental alkaline phosphatase: a potential marker for the early detection of testis tumour. BJU Int. 2000;86:894-900.
Ory, et al. Characterization of polymorphic forms of Fc receptor III on human neutrophils. J. Clin. Invest. 1989; 83:1676-81.
Presta, et al. Humanization of an antibody directed against IgE. J. Immunol. 1993;151:2623-2632.
Ravetch, et al. Alternative membrane forms of Fc gamma RIII(CD16) on human natural killer cells and neutrophils. Cell type-specific expression of two genes that differ in single nucleotide substitutions. J Exp Med. Aug. 1, 1989;170(2):481-97.
Ravn, et al. Multivalent scFv display of phagemid repertoires for the selection of carbohydrate-specific antibodies and its application to the Thomsen-Friedenreich antigen. J. Mol. Biol. 2004;343:985-996.
Reff, et al. Depletion of B cells in vivo by a chimeric mouse human monoclonal antibody to CD20. Blood. 1994;83:435-445.
Renner, et al. Targeting properties of an anti-CD16/anti-CD30 bispecific antibody in an in vivo system. Cancer Immunol. Immunother. 2001;50:102-108.
Reusch, et al. Effect of tetravalent bispecific CD19×CD3 recombinant antibody construct and CD28 costimulation on lysis of malignant B cells from patients with chronic lymphocytic leukemia by autologous T cells. Int. J. Cancer. 2004;112:509-518.
Robertson, et al. Biology and clinical relevance of human natural killer cells. Blood. 1990; 76:2421-2438.
Schueler-Furman, et al. Structure-based prediction of binding peptides to MHC class I molecules: application to a broad range of MHC alleles. Protein Sci. 2000;9:1838-1846.
Schwarz, et al. Single-chain antibodies for the conformation-specific blockade of activated platelet integrin alphaIIbbeta3 designed by subtractive selection from naive human phage libraries. FASEB J. 2004;18:1704-6.
Selvaraj, et al. Natural killer cell and granulocyte Fc gamma receptor III (CD16) differ in membrane anchor and signal transduction. J Immunol. Nov. 15, 1989;143(10):3283-8.
Studnicka, et al. Human-engineered monoclonal antibodies retain full specific binding activity by preserving non-CDR complementarity-modulating residues. Protein Eng. 1994;7:805-814.
Tamm, et al. The binding epitopes of human CD16 (Fc gamma RIII) monoclonal antibodies. J. Immunol. 1996;157:1576-1581.
Van De Winkel, et al. Human IgG Fc receptor heterogeneity: molecular aspects and clinical implications. Immunol. Today. 1993;14(5):215-221.
Van Spriel, et al. Immunotherapeutic perspective for bispecific antibodies. Immunol Today. Aug. 2000;21(8):391-7.
Vivier, et al. Structure and function of the CD16:zeta:gamma complex expressed on human natural-killer cells.1992, Int. J. Cancer Suppl. 7:11-14 (abstract).
Wirthmueller, et al. Signal transduction by Fc gamma RIII (CD16) is mediated through the gamma chain. J. Exp. Med. 1992;175:1381-1390.
Biocytex; "Data Sheet of CD16-PE" (Oct. 2005).
Zilber et al.; "CD38 Expressed on Human Monocytes: A Coaccessory Molecule in the Superantigen-Induced Proliferation"; PNAS; vol. 97, No. 6, pp. 2840-2845 (Mar. 14, 2000).

* cited by examiner

FIGURE 6

| | | | | | | |
|---|---|---|---|---|---|---|
| CD16B_NA1 | MWQLLLPTAL | LLLVSAGMRT | EDLPKAVVFL | EPQWYRVLEK | DSVTLKCQGA | 32(50) |
| CD16B_NA2 | MWQLLLPTAL | LLLVSAGMRT | EDLPKAVVFL | EPQWYSVLEK | DSVTLKCQGA | 32(50) |
| CD16B_SH | MWQLLLPTAL | LLLVSAGMRT | EDLPKAVVFL | EPQWYSVLEK | DSVTLKCQGA | 32(50) |
| CD16A_48R_158F | MWQLLLPTAL | LLLVSAGMRT | EDLPKAVVFL | EPQWYRVLEK | DSVTLKCQGA | 32(50) |
| CD16A_48R_158V | MWQLLLPTAL | LLLVSAGMRT | EDLPKAVVFL | EPQWYRVLEK | DSVTLKCQGA | 32(50) |

| | | | | | | |
|---|---|---|---|---|---|---|
| CD16B_NA1 | YSPEDNSTQW | FHNENLISSQ | ASSYFIDAAT | VDDSGEYRCQ | TNLSTLSDPV | 82(100) |
| CD16B_NA2 | YSPEDNSTQW | FHNESLISSQ | ASSYFIDAAT | VNDSGEYRCQ | TNLSTLSDPV | 82(100) |
| CD16B_SH | YSPEDNSTQW | FHNESLISSQ | ASSYFIDDAT | VNDSGEYRCQ | TNLSTLSDPV | 82(100) |
| CD16A_48R_158F | YSPEDNSTQW | FHNESRISSQ | ASSYFIDAAT | VDDSGEYRCQ | TNLSTLSDPV | 82(100) |
| CD16A_48R_158V | YSPEDNSTQW | FHNESRISSQ | ASSYFIDAAT | VDDSGEYRCQ | TNLSTLSDPV | 82(100) |

| | | | | | | |
|---|---|---|---|---|---|---|
| CD16B_NA1 | QLEVHVGWLL | LQAPRWVFKE | EDPIHLRCHS | WKNTALHKVT | YLQNGKDRKY | 132(150) |
| CD16B_NA2 | QLEVHIGWLL | LQAPRWVFKE | EDPIHLRCHS | WKNTALHKVT | YLQNGKDRKY | 132(150) |
| CD16B_SH | QLEVHIGWLL | LQAPRWVFKE | EDPIHLRCHS | WKNTALHKVT | YLQNGKDRKY | 132(150) |
| CD16A_48R_158F | QLEVHIGWLL | LQAPRWVFKE | EDPIHLRCHS | WKNTALHKVT | YLQNGKGRKY | 132(150) |
| CD16A_48R_158V | QLEVHIGWLL | LQAPRWVFKE | EDPIHLRCHS | WKNTALHKVT | YLQNGKGRKY | 132(150) |

| | | | | | | |
|---|---|---|---|---|---|---|
| CD16B_NA1 | FHHNSDFHIP | KATLKDSGSY | FCRGIVGSKN | VSSETVNITI | TQGLAVSTIS | 182(200) |
| CD16B_NA2 | FHHNSDFHIP | KATLKDSGSY | FCRGIVGSKN | VSSETVNITI | TQGLAVSTIS | 182(200) |
| CD16B_SH | FHHNSDFHIP | KATLKDSGSY | FCRGIVGSKN | VSSETVNITI | TQGLAVSTIS | 182(200) |
| CD16A_48R_158F | FHHNSDFYIP | KATLKDSGSY | FCRGIFGSKN | VSSETVNITI | TQGLAVSTIS | 182(200) |
| CD16A_48R_158V | FHHNSDFYIP | KATLKDSGSY | FCRGIVGSKN | VSSETVNITI | TQGLAVSTIS | 182(200) |

| | | |
|---|---|---|
| CD16B_NA1 | SFSPPG | 188(206) |
| CD16B_NA2 | SFSPPG | 188(206) |
| CD16B_SH | SFSPPG | 188(206) |
| CD16A_48R_158F | SFFPPG | 188(206) |
| CD16A_48R_158V | SFFPPG | 188(206) |

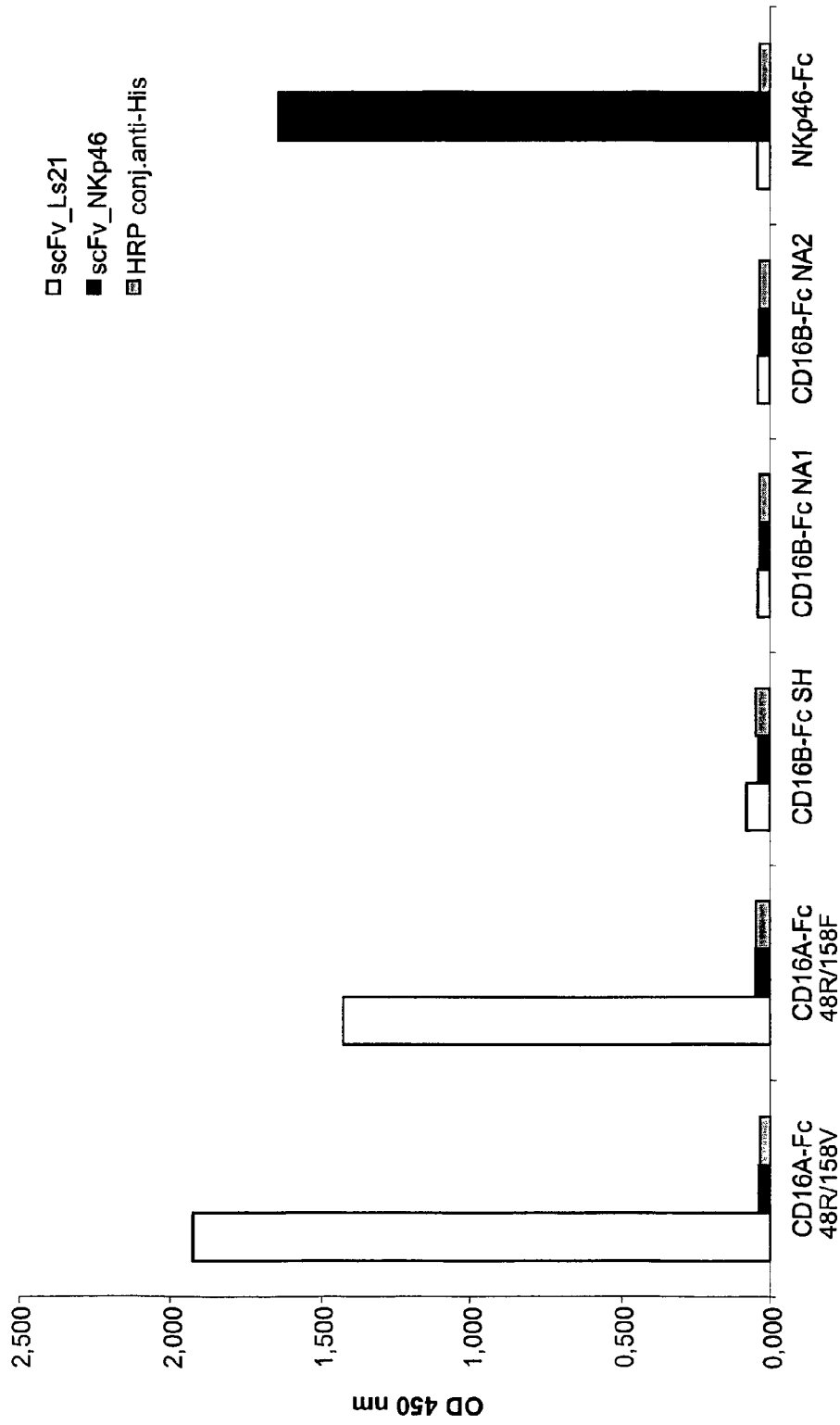

FIGURE 8
[A]
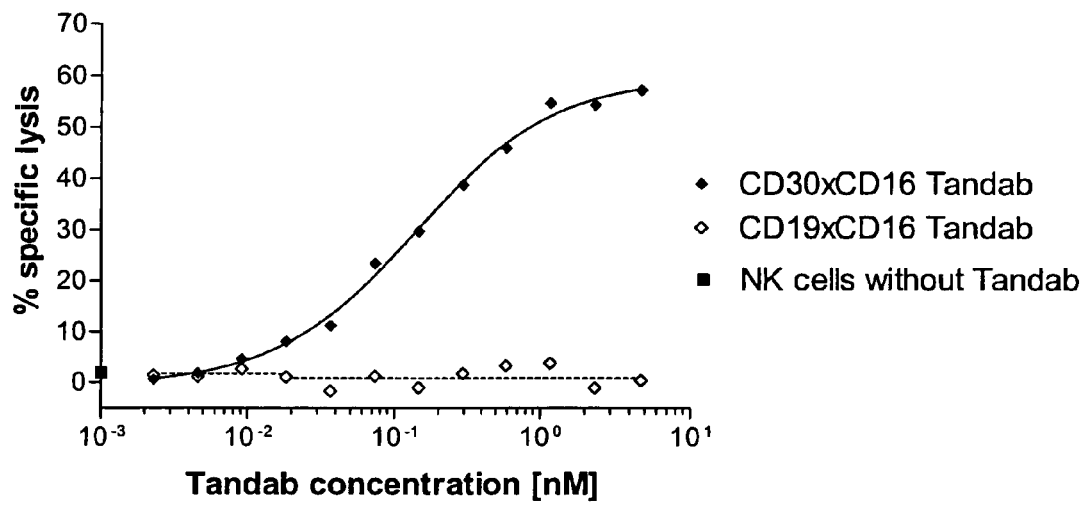
[B]
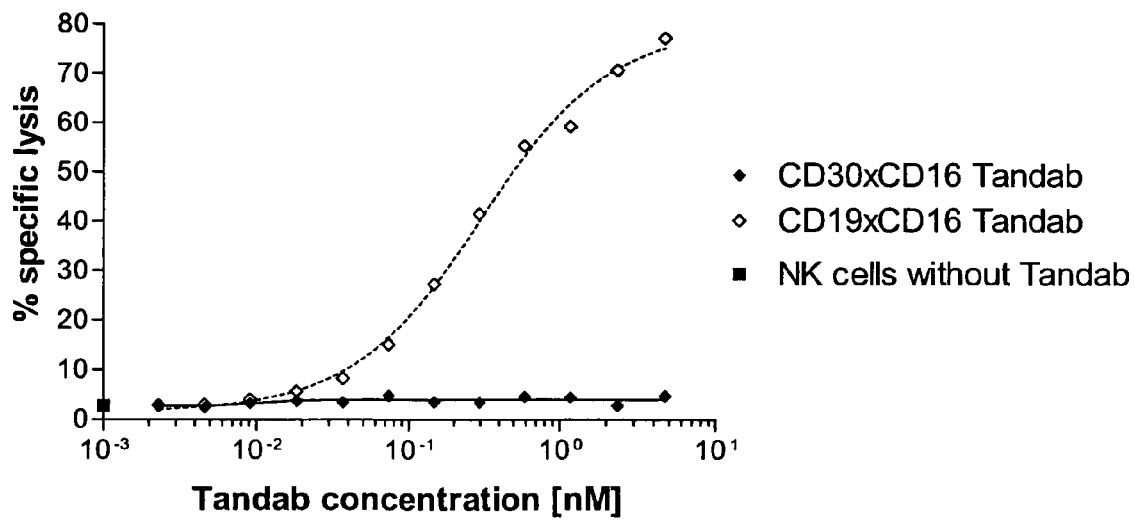

SEQUENCE LISTING

```
<160> NUMBER OF SEQ ID NOS: 54

<210> SEQ ID NO 1
<211> LENGTH: 360
<212> TYPE: DNA
<213> ORGANISM: H. sapiens

<400> SEQUENCE: 1
gaggtccagc tggtacagtc tggagcagag gtgaaaaagc ccggggagtc tctgaaggtt      60
tcctgcaagg catctggata caccttcacc agctactata tgcactgggt gcgacaggcc     120
cctggacaag ggcttgagtg gatgggaata atcaacccta gtggtggtag cacaagctac     180
gcacagaagt tccagggcag agtcaccatg acccgggaca cgtccacgag cacagtctac     240
atggagctta gcagcctgag atctgaggac acggccgtgt attactgtgc tagaggtagt     300
gcttattact acgattttgc tgactactgg ggccaggaa ccctggtcac cgtctcctca      360

<210> SEQ ID NO 2
<211> LENGTH: 318
<212> TYPE: DNA
<213> ORGANISM: H. sapiens

<400> SEQUENCE: 2
tcctatgagc tgatgcagcc accctcagtg tccgtgtcct caggacagac agccagcatc      60
ccctgctctg gagataaatt ggaggaaaaa tatgtttcct ggtatcaaca gaggccaggc     120
cagtcccctg tgttggtcat ttatcaggat aataagcggc cctcagggat ccctgagcga     180
ttctctggct ccaactctgg gaacacagcc actctgacca tcagcgggac ccaggcgatg     240
gatgaggctg actactattg tcaggtgtgg gacaattaca gtgtgctatt cggcggaggg     300
accaagctga ccgtccta                                                    318

<210> SEQ ID NO 3
<211> LENGTH: 318
<212> TYPE: DNA
<213> ORGANISM: Artificial sequence
<220> FEATURE:
<223> OTHER INFORMATION: 3-LB3 VL region

<400> SEQUENCE: 3
tcctatgagc tgacacagcc actctcagag tcagtggccc agggacagac ggccaggatt      60
acctgtgggg gaaacaacat tgaaagtaga aatgttcact ggtaccagca gaagccaggc     120
caggcccctg tgttggtcat ctagggat aacaaccggc cctctgggat ccctgagcga       180
ttctctggct ccaattcggg gaacatggcc accctgacca tcagcagagc ccaagccggg     240
```

```
gatgcagctg actattactg tcaggtgtgg gacaactaca ctgtgctatt cggcggaggg    300
accaagctga ccgtccta                                                  318

<210> SEQ ID NO 4
<211> LENGTH: 318
<212> TYPE: DNA
<213> ORGANISM: Artificial sequence
<220> FEATURE:
<223> OTHER INFORMATION: 3-LB5 VL region

<400> SEQUENCE: 4
tcctatgagc tgacacagcc accctcagtg gcagtggccc caggaaagac ggccaggatt    60
acctgtgggg gaaacaacat tggaagtaaa aatgtgcact ggtaccagca gaagccaggc   120
caggcccctg tgctggtcat ctatagggat agcaaccggc cctctgggat ccctgagcga   180
ttctctggct ccaactcggg gaacacggcc accctgacca tcagcagagc caagccgggg   240
gatgaggctg acttttattg tcaggtgtgg gacaactata ttgtgctgtt cggcggaggg   300
accaagctga ccgtcctg                                                  318

<210> SEQ ID NO 5
<211> LENGTH: 318
<212> TYPE: DNA
<213> ORGANISM: Artificial sequence
<220> FEATURE:
<223> OTHER INFORMATION: 3-LB6 VL region

<400> SEQUENCE: 5
caggctgtgc tgactcagcc gccctcagtg tcagtggccc caggacagac ggccaggatt    60
ccctgtgagg gaaacaacat tggaagtaaa aatgtccact ggtatcggca gaagccaggc   120
caggtccctg tcctggtcat gtatgatgat agcgaccggc cctcagggat ccctgagcga   180
ttctctggct ccaactctgg gaacacagcc actctgacca tcagcgggac ccaggcgatg   240
gatgaggctg actactattg tcaggtgtgg gacaattaca gtgtgctatt cggcggaggg   300
accaagctga ccgtccta                                                  318

<210> SEQ ID NO 6
<211> LENGTH: 318
<212> TYPE: DNA
<213> ORGANISM: Artificial sequence
<220> FEATURE:
<223> OTHER INFORMATION: 3-LS49 VL region

<400> SEQUENCE: 6
cagcctgtgc tgactcagcc actctcagtg tcagtggccc cgggacagac ggccaggatt    60
acctgtgggg gaaacaacat tggaagtaaa aatgtgcact ggtaccagca gaagccaggc   120
caggcccctg tactggtcat ctatagggac agcagccggc cctctgggat ccctgagcga   180
ctctctggct ccaactcggg ggacacggcc accctgacca tcagcagagc ccaggccggg   240
gatgaggctg actattactg tcaggtgtgg gacgactaca ttgtggtctt cggcggaggg   300
accaagctga ccgtccta                                                  318

<210> SEQ ID NO 7
<211> LENGTH: 318
<212> TYPE: DNA
<213> ORGANISM: Artificial sequence
<220> FEATURE:
<223> OTHER INFORMATION: 4-LS14 VL region

<400> SEQUENCE: 7
```

```
tcctatgagc tgacacagcc accctcggtg tcagtgaccc caggacagac ggccacgatt    60
acctgcgggg caaacgacat tggaaaaaga aatgtccact ggtaccaaca gaggccaggc   120
cagtcccctg tgttggtcat ttatcaggat aataagcggc cctcagggat ccctgagcga   180
ttctctggct ccaactctgg aacacagcc actctgacca tcagcgggac ccaggcgatg    240
gatgaggctg actactattg tcaggtgtgg gacaattaca gtgtgctatt cggcggaggg   300
accaagctga ccgtccta                                                 318

<210> SEQ ID NO 8
<211> LENGTH: 318
<212> TYPE: DNA
<213> ORGANISM: Artificial sequence
<220> FEATURE:
<223> OTHER INFORMATION: 4-LS21 VL region

<400> SEQUENCE: 8
cagcctgtgc tgactcagcc atcctcggtg tcagtggccc caggacagac ggccacgatc    60
tcctgtgggg gacacaacat tgggagtaaa aatgtgcact ggtaccagca gaggccaggc   120
cagtcccctg tgttggtcat ttatcaggat aataagcggc cctcagggat ccctgagcga   180
ttctctggct ccaactctgg aacacagcc actctgacca tcagcgggac ccaggcgatg    240
gatgaggctg actactattg tcaggtgtgg gacaattaca gtgtgctatt cggcggaggg   300
accaagctga ccgtccta                                                 318

<210> SEQ ID NO 9
<211> LENGTH: 121
<212> TYPE: PRT
<213> ORGANISM: H. sapiens

<400> SEQUENCE: 9

Glu Glu Val Gln Leu Val Gln Ser Gly Ala Glu Val Lys Lys Pro Gly
1               5                   10                  15

Glu Ser Leu Lys Val Ser Cys Lys Ala Ser Gly Tyr Thr Phe Thr Ser
            20                  25                  30

Tyr Tyr Met His Trp Val Arg Gln Ala Pro Gly Gln Gly Leu Glu Trp
        35                  40                  45

Met Gly Ile Ile Asn Pro Ser Gly Gly Ser Thr Ser Tyr Ala Gln Lys
    50                  55                  60

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Gly Ser Ala Tyr Tyr Tyr Asp Phe Ala Asp Tyr Trp Gly
            100                 105                 110

Gln Gly Thr Leu Val Thr Val Ser Ser
        115                 120

<210> SEQ ID NO 10
<211> LENGTH: 106
<212> TYPE: PRT
<213> ORGANISM: H. sapiens

<400> SEQUENCE: 10

Ser Tyr Glu Leu Met Gln Pro Pro Ser Val Ser Val Ser Ser Gly Gln
1               5                   10                  15

Thr Ala Ser Ile Pro Cys Ser Gly Asp Lys Leu Glu Glu Lys Tyr Val
```

```
                    20                  25                  30

Ser Trp Tyr Gln Gln Arg Pro Gly Gln Ser Pro Val Leu Val Ile Tyr
            35                  40                  45

Gln Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 11
<211> LENGTH: 106
<212> TYPE: PRT
<213> ORGANISM: Artificial sequence
<220> FEATURE:
<223> OTHER INFORMATION: 3-LB3 VL amino acid sequence

<400> SEQUENCE: 11

Ser Tyr Glu Leu Thr Gln Pro Leu Ser Glu Ser Val Ala Gln Gly Gln
1               5                   10                  15

Thr Ala Arg Ile Thr Cys Gly Gly Asn Asn Ile Glu Ser Arg Asn Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Met Ala Thr Leu Thr Ile Ser Arg Ala Gln Ala Gly
65                  70                  75                  80

Asp Ala Ala Asp Tyr Tyr Cys Gln Val Trp Asp Asn Tyr Thr Val Leu
                85                  90                  95

Phe Gly Gly Gly Thr Lys Leu Thr Val Leu
            100                 105

<210> SEQ ID NO 12
<211> LENGTH: 106
<212> TYPE: PRT
<213> ORGANISM: Artificial sequence
<220> FEATURE:
<223> OTHER INFORMATION: 3-LB5 VL amino acid sequence

<400> SEQUENCE: 12

Ser Tyr Glu Leu Thr Gln Pro Pro Ser Val Ala Val Ala Pro Gly Lys
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Phe Tyr Cys Gln Val Trp Asp Asn Tyr Ile Val Leu
                85                  90                  95

Phe Gly Gly Gly Thr Lys Leu Thr Val Leu
            100                 105
```

<210> SEQ ID NO 13
<211> LENGTH: 106
<212> TYPE: PRT
<213> ORGANISM: Artificial sequence
<220> FEATURE:
<223> OTHER INFORMATION: 3-LB6 VL amino acid sequence

<400> SEQUENCE: 13

Gln Ala Val Leu Thr Gln Pro Pro Ser Val Ser Val Ala Pro Gly Gln
1               5                   10                  15

Thr Ala Arg Ile Pro Cys Glu Gly Asn Asn Ile Gly Ser Lys Asn Val
            20                  25                  30

His Trp Tyr Arg Gln Lys Pro Gly Gln Val Pro Val Leu Val Met Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 14
<211> LENGTH: 106
<212> TYPE: PRT
<213> ORGANISM: Artificial sequence
<220> FEATURE:
<223> OTHER INFORMATION: 3-LS49 VL amino acid sequence

<400> SEQUENCE: 14

Gln Pro Val Leu Thr Gln Pro Leu Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Ser Arg Pro Ser Gly Ile Pro Glu Arg Leu Ser Gly Ser
    50                  55                  60

Asn Ser Gly Asp Thr Ala Thr Leu Thr Ile Ser Arg Ala Gln Ala Gly
65                  70                  75                  80

Asp Glu Ala Asp Tyr Tyr Cys Gln Val Trp Asp Asp Tyr Ile Val Val
                85                  90                  95

Phe Gly Gly Gly Thr Lys Leu Thr Val Leu
            100                 105

<210> SEQ ID NO 15
<211> LENGTH: 106
<212> TYPE: PRT
<213> ORGANISM: Artificial sequence
<220> FEATURE:
<223> OTHER INFORMATION: 4-LS14 VL amino acid sequence

<400> SEQUENCE: 15

Ser Tyr Glu Leu Thr Gln Pro Pro Ser Val Ser Val Thr Pro Gly Gln
1               5                   10                  15

Thr Ala Thr Ile Thr Cys Gly Ala Asn Asp Ile Gly Lys Arg Asn Val
            20                  25                  30

His Trp Tyr Gln Gln Arg Pro Gly Gln Ser Pro Val Leu Val Ile Tyr

```
            35                  40                  45

Gln Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 16
<211> LENGTH: 106
<212> TYPE: PRT
<213> ORGANISM: Artificial sequence
<220> FEATURE:
<223> OTHER INFORMATION: 4-LS21 VL amino acid sequence

<400> SEQUENCE: 16

Gln Pro Val Leu Thr Gln Pro Ser Ser Val Ser Val Ala Pro Gly Gln
 1               5                  10                  15

Thr Ala Thr Ile Ser Cys Gly Gly His Asn Ile Gly Ser Lys Asn Val
                20                  25                  30

His Trp Tyr Gln Gln Arg Pro Gly Gln Ser Pro Val Leu Val Ile Tyr
            35                  40                  45

Gln Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 17
<211> LENGTH: 6
<212> TYPE: PRT
<213> ORGANISM: H. sapiens

<400> SEQUENCE: 17

Thr Ser Tyr Tyr Met His
 1               5

<210> SEQ ID NO 18
<211> LENGTH: 17
<212> TYPE: PRT
<213> ORGANISM: H. sapiens

<400> SEQUENCE: 18

Ile Ile Asn Pro Ser Gly Gly Ser Thr Ser Tyr Ala Gln Lys Phe Gln
 1               5                  10                  15

Gly

<210> SEQ ID NO 19
<211> LENGTH: 11
<212> TYPE: PRT
<213> ORGANISM: H. sapiens

<400> SEQUENCE: 19

Gly Ser Ala Tyr Tyr Tyr Asp Phe Ala Asp Tyr
 1               5                  10
```

<210> SEQ ID NO 20
<211> LENGTH: 11
<212> TYPE: PRT
<213> ORGANISM: H. sapiens

<400> SEQUENCE: 20

Ser Gly Asp Lys Leu Glu Glu Lys Tyr Val Ser
1               5                   10

<210> SEQ ID NO 21
<211> LENGTH: 7
<212> TYPE: PRT
<213> ORGANISM: H. sapiens

<400> SEQUENCE: 21

Gln Asp Asn Lys Arg Pro Ser
1               5

<210> SEQ ID NO 22
<211> LENGTH: 9
<212> TYPE: PRT
<213> ORGANISM: H. sapiens

<400> SEQUENCE: 22

Gln Val Trp Asp Asn Tyr Ser Val Leu
1               5

<210> SEQ ID NO 23
<211> LENGTH: 11
<212> TYPE: PRT
<213> ORGANISM: Artificial sequence
<220> FEATURE:
<223> OTHER INFORMATION: 3-LB3 LC CDR1

<400> SEQUENCE: 23

Gly Gly Asn Asn Ile Glu Ser Arg Asn Val His
1               5                   10

<210> SEQ ID NO 24
<211> LENGTH: 7
<212> TYPE: PRT
<213> ORGANISM: Artificial sequence
<220> FEATURE:
<223> OTHER INFORMATION: 3-LB3 LC CDR2

<400> SEQUENCE: 24

Arg Asp Asn Asn Arg Pro Ser
1               5

<210> SEQ ID NO 25
<211> LENGTH: 9
<212> TYPE: PRT
<213> ORGANISM: Artificial sequence
<220> FEATURE:
<223> OTHER INFORMATION: 3-LB3 LC CDR3

<400> SEQUENCE: 25

Gln Val Trp Asp Asn Tyr Thr Val Leu
1               5

<210> SEQ ID NO 26
<211> LENGTH: 11
<212> TYPE: PRT
<213> ORGANISM: Artificial sequence
<220> FEATURE:

```
<223> OTHER INFORMATION: 3-LB5 LC CDR1

<400> SEQUENCE: 26

Gly Gly Asn Asn Ile Gly Ser Lys Asn Val His
1               5                   10

<210> SEQ ID NO 27
<211> LENGTH: 7
<212> TYPE: PRT
<213> ORGANISM: Artificial sequence
<220> FEATURE:
<223> OTHER INFORMATION: 3-LB5 LC CDR2

<400> SEQUENCE: 27

Arg Asp Ser Asn Arg Pro Ser
1               5

<210> SEQ ID NO 28
<211> LENGTH: 9
<212> TYPE: PRT
<213> ORGANISM: Artificial sequence
<220> FEATURE:
<223> OTHER INFORMATION: 3-LB5 LC CDR3

<400> SEQUENCE: 28

Gln Val Trp Asp Asn Tyr Ile Val Leu
1               5

<210> SEQ ID NO 29
<211> LENGTH: 11
<212> TYPE: PRT
<213> ORGANISM: Artificial sequence
<220> FEATURE:
<223> OTHER INFORMATION: 3-LB6 LC CDR1

<400> SEQUENCE: 29

Glu Gly Asn Asn Ile Gly Ser Lys Asn Val His
1               5                   10

<210> SEQ ID NO 30
<211> LENGTH: 7
<212> TYPE: PRT
<213> ORGANISM: Artificial sequence
<220> FEATURE:
<223> OTHER INFORMATION: 3-LB6 LC CDR2

<400> SEQUENCE: 30

Asp Asp Ser Asp Arg Pro Ser
1               5

<210> SEQ ID NO 31
<211> LENGTH: 7
<212> TYPE: PRT
<213> ORGANISM: Artificial sequence
<220> FEATURE:
<223> OTHER INFORMATION: 3-LS49 LC CDR2

<400> SEQUENCE: 31

Arg Asp Ser Ser Arg Pro Ser
1               5

<210> SEQ ID NO 32
<211> LENGTH: 9
<212> TYPE: PRT
<213> ORGANISM: Artificial sequence
<220> FEATURE:
<223> OTHER INFORMATION: 3-LS49 LC CDR3
```

<400> SEQUENCE: 32

Gln Val Trp Asp Asp Tyr Ile Val Val
1               5

<210> SEQ ID NO 33
<211> LENGTH: 11
<212> TYPE: PRT
<213> ORGANISM: Artificial sequence
<220> FEATURE:
<223> OTHER INFORMATION: 4-LS14 LC CDR1

<400> SEQUENCE: 33

Gly Ala Asn Asp Ile Gly Lys Arg Asn Val His
1               5                   10

<210> SEQ ID NO 34
<211> LENGTH: 11
<212> TYPE: PRT
<213> ORGANISM: Artificial sequence
<220> FEATURE:
<223> OTHER INFORMATION: 4-LS21 LC CDR1

<400> SEQUENCE: 34

Gly Gly His Asn Ile Gly Ser Lys Asn Val His
1               5                   10

<210> SEQ ID NO 35
<211> LENGTH: 7
<212> TYPE: PRT
<213> ORGANISM: Artificial sequence
<220> FEATURE:
<223> OTHER INFORMATION: 4-LS21 LC CDR2

<400> SEQUENCE: 35

Gln Asp Asn Lys Arg Pro Ser
1               5

<210> SEQ ID NO 36
<211> LENGTH: 921
<212> TYPE: DNA
<213> ORGANISM: Artificial sequence
<220> FEATURE:
<223> OTHER INFORMATION: clone pSKK2-50NI

<400> SEQUENCE: 36

```
atgaaatacc tattgcctac ggcagccgct ggcttgctgc tgctggcagc tcagccggcc      60
atggcggagg tccagctggt acagtctgga gcagaggtga aaaagcccgg ggagtctctg     120
aaggtttcct gcaaggcatc tggatacacc ttcaccagct actatatgca ctgggtgcga     180
caggcccctg gacaagggct tgagtggatg gaataatca  accctagtgg tggtagcaca     240
agctacgcac agaagttcca gggcagagtc accatgaccc gggacacgtc cacgagcaca     300
gtctacatgg agcttagcag cctgagatct gaggacacgg ccgtgtatta ctgtgctaga     360
ggtagtgctt attactacga ttttgctgac tactggggcc agggaaccct ggtcaccgtc     420
tcctcaggga gtgcatccgc cccaacccct aagcttgaag aaggtgaatt ttcagaagca     480
cgcgtatcct atgagctgat gcagccaccc tcagtgtccg tgtcctcagg acagacagcc     540
agcatcccct gctctggaga taaattggag gaaaaatatg tttcctggta tcaacagagg     600
ccaggccagt cccctgtgtt ggtcatttat caggataata gcggccctc  agggatccct     660
gagcgattct ctggctccaa ctctgggaac acagccactc tgaccatcag cgggacccag     720
```

```
gcgatggatg aggctgacta ctattgtcag gtgtgggaca attacagtgt gctattcggc    780
ggagggacca agctgaccgt cctaggtcag cccaaggctg cccctcggt cactctgttc     840 ccgccgtccg cggccgctgg atccgaacaa aagctgatct cagaagaaga cctaaactca    900
catcaccatc accatcacta a                                              921
```

<210> SEQ ID NO 37
<211> LENGTH: 921
<212> TYPE: DNA
<213> ORGANISM: Artificial sequence
<220> FEATURE:
<223> OTHER INFORMATION: clone pSKK2-3-LB3

<400> SEQUENCE: 37

```
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg gacaagggct tgagtggatg gaataatca ccctagtgg tggtagcaca     240 agctacgcac agaagttcca gggcagagtc accatgaccc gggacacgtc cacgagcaca    300
gtctacatgg agcttagcag cctgagatct gaggacacgg ccgtgtatta ctgtgctaga    360
ggtagtgctt attactacga ttttgctgac tactggggcc agggaaccct ggtcaccgtc    420
tcctcaggga gtgcatccgc cccaaccctt aagcttgaag aaggtgaatt ttcagaagca    480
cgcgtatcct atgagctgac acagccactc tcagagtcag tggcccaggg acagacggcc    540
aggattacct gtggggaaaa caacattgaa agtagaaatg ttcactggta ccagcagaag    600
ccaggccagg cccctgtgtt ggtcatctat aggataaca accggccctc tgggatccct    660
gagcgattct ctggctccaa ttcggggaac atggccaccc tgaccatcag cagagcccaa    720
gccggggatg cagctgacta ttactgtcag gtgtgggaca actacactgt gctattcggc    780
ggagggacca agctgaccgt cctaggtcag cccaaggctg cccctcggt cactctgttc     840 ccgccgtccg cggccgctgg atccgaacaa aagctgatct cagaagaaga cctaaactca    900
catcaccatc accatcacta a                                              921
```

<210> SEQ ID NO 38
<211> LENGTH: 921
<212> TYPE: DNA
<213> ORGANISM: Artificial sequence
<220> FEATURE:
<223> OTHER INFORMATION: clone pSKK2-3-LB5

<400> SEQUENCE: 38

```
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg gacaagggct tgagtggatg gaataatca ccctagtgg tggtagcaca     240 agctacgcac agaagttcca gggcagagtc accatgaccc gggacacgtc cacgagcaca    300
gtctacatgg agcttagcag cctgagatct gaggacacgg ccgtgtatta ctgtgctaga    360
ggtagtgctt attactacga ttttgctgac tactggggcc agggaaccct ggtcaccgtc    420
tcctcaggga gtgcatccgc cccaaccctt aagcttgaag aaggtgaatt ttcagaagca    480
cgcgtatcct atgagctgac acagccaccc tcagtgcag tggccccagg aaagacggcc    540
aggattacct gtggggaaaa caacattgga agtaaaaatg tgcactggta ccagcagaag    600
```

```
ccaggccagg cccctgtgct ggtcatctat agggatagca accggccctc tgggatccct    660
gagcgattct ctggctccaa ctcggggaac acgccaccc tgaccatcag cagagcccaa     720
gccggggatg aggctgactt ttattgtcag gtgtgggaca actatattgt gctgttcggc    780
ggagggacca agctgaccgt cctgggtcag cccaaggctg cccctcggt cactctgttc     840 ccgccgtccg cggccgctgg atccgaacaa aagctgatct cagaagaaga cctaaactca    900
catcaccatc accatcacta a                                              921

<210> SEQ ID NO 39
<211> LENGTH: 921
<212> TYPE: DNA
<213> ORGANISM: Artificial sequence
<220> FEATURE:
<223> OTHER INFORMATION: clone pSKK2-3-LB6

<400> SEQUENCE: 39
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg acaagggct tgagtggatg gaataatca accctagtgg tggtagcaca      240
agctacgcac agaagttcca gggcagagtc accatgaccc gggacacgtc cacgagcaca    300
gtctacatgg agcttagcag cctgagatct gaggacacgg ccgtgtatta ctgtgctaga    360
ggtagtgctt attactacga ttttgctgac tactggggcc agggaaccct ggtcaccgtc    420
tcctcaggga gtgcatccgc cccaacccct aagcttgaag aaggtgaatt ttcagaagca    480
cgcgtacagg ctgtgctgac tcagccgccc tcagtgtcag tggccccagg acagacggcc    540
aggattccct gtgagggaaa caacattgga agtaaaaatg tccactggta tcggcagaag    600
ccaggccagg tccctgtcct ggtcatgtat gatgatagcg accggccctc agggatccct    660
gagcgattct ctggctccaa ctctgggaac acagccactc tgaccatcag cgggacccag    720
gcgatggatg aggctgacta ctattgtcag gtgtgggaca attacagtgt gctattcggc    780
ggagggacca agctgaccgt cctaggtcag cccaaggctg cccctcggt cactctgttc     840 ccgccgtccg cggccgctgg atccgaacaa aagctgatct cagaagaaga cctaaactca    900
catcaccatc accatcacta a                                              921

<210> SEQ ID NO 40
<211> LENGTH: 921
<212> TYPE: DNA
<213> ORGANISM: Artificial sequence
<220> FEATURE:
<223> OTHER INFORMATION: clone pSKK2-3-LS49

<400> SEQUENCE: 40
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg acaagggct tgagtggatg gaataatca accctagtgg tggtagcaca      240
agctacgcac agaagttcca gggcagagtc accatgaccc gggacacgtc cacgagcaca    300
gtctacatgg agcttagcag cctgagatct gaggacacgg ccgtgtatta ctgtgctaga    360
ggtagtgctt attactacga ttttgctgac tactggggcc agggaaccct ggtcaccgtc    420
```

```
tcctcaggga gtgcatccgc cccaacccTt aagcttgaag aaggtgaatt ttcagaagca    480
cgcgtacagc ctgtgctgac tcagccactc tcagtgtcag tggccccggg acagacggcc    540
aggattacct gtgggggaaa caacattgga agtaaaaatg tgcactggta ccagcagaag    600
ccaggccagg cccctgtact ggtcatctat agggacagca gccggccctc tgggatccct    660
gagcgactct ctggctccaa ctcggggggac acggccaccc tgaccatcag cagagcccag    720
gccggggatg aggctgacta ttactgtcag gtgtgggacg actacattgt ggtcttcggc    780
ggagggacca gctgaccgt cctaggtcag cccaaggctg ccccccggt cactctgttc    840 ccgccgtccg cggccgctgg atccgaacaa aagctgatct cagaagaaga cctaaactca    900
catcaccatc accatcacta a                                             921

<210> SEQ ID NO 41
<211> LENGTH: 921
<212> TYPE: DNA
<213> ORGANISM: Artificial sequence
<220> FEATURE:
<223> OTHER INFORMATION: clone pSKK2-4-LS14

<400> SEQUENCE: 41
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg gacaagggct tgagtggatg ggaataatca accctagtgg tggtagcaca    240
agctacgcac agaagttcca gggcagagtc accatgaccc gggacacgtc cacgagcaca    300
gtctacatgg agcttagcag cctgagatct gaggacacgg ccgtgtatta ctgtgctaga    360
ggtagtgctt attactacga tttttgctgac tactgggggcc aggggaaccct ggtcaccgtc    420 tcctcaggga gtgcatccgc cccaacccTt aagcttgaag aaggtgaatt ttcagaagca    480
cgcgtatcct atgagctgac acagccaccc tcggtgtcag tgaccccagg acagacggcc    540
acgattacct gcgggggcaaa cgacattgga aaagaaatg tccactggta ccaacagagg    600
ccaggccagt cccctgtgtt ggtcattta caggataata gcggccctc agggatccct    660 gagcgattct ctggctccaa ctctgggaac acagccactc tgaccatcag cgggacccag    720
gcgatggatg aggctgacta ctattgtcag gtgtgggaca attacagtgt gctattcggc    780
ggagggacca gctgaccgt cctaggtcag cccaaggctg ccccctcggt cactctgttc    840
ccgccgtccg cggccgctgg atccgaacaa aagctgatct cagaagaaga cctaaactca    900
catcaccatc accatcacta a                                             921

<210> SEQ ID NO 42
<211> LENGTH: 921
<212> TYPE: DNA
<213> ORGANISM: Artificial sequence
<220> FEATURE:
<223> OTHER INFORMATION: clone pSKK2-4-LS21

<400> SEQUENCE: 42
atgaaatacc tattgcctac ggcagccgct ggcttgctgc tgctggcagc tcagccggcc     60
atggcggagg tccagctggt acagtctgga gcagaggtga aaaagcccgg ggagtctctg    120
aaggtttcct gcaaggcatc tggatacacc ttcaccagct actatatgca ctgggtgcga    180
caggcccctg gacaagggct tgagtggatg ggaataatca accctagtgg tggtagcaca    240
agctacgcac agaagttcca gggcagagtc accatgaccc gggacacgtc cacgagcaca    300
```

```
gtctacatgg agcttagcag cctgagatct gaggacacgg ccgtgtatta ctgtgctaga    360
ggtagtgctt attactacga ttttgctgac tactggggcc agggaaccct ggtcaccgtc    420
tcctcaggga gtgcatccgc cccaaccctt aagcttgaag aaggtgaatt ttcagaagca    480
cgcgtacagc ctgtgctgac tcagccatcc tcggtgtcag tggccccagg acagacggcc    540
acgatctcct gtgggggaca acacattggg agtaaaaatg tgcactggta ccagcagagg    600
ccaggccagt ccctgtgtt ggtcatttat caggataata gcggccctc agggatccct     660 gagcgattct ctggctccaa ctctgggaac acagccactc tgaccatcag cgggacccag    720
gcgatggatg aggctgacta ctattgtcag gtgtgggaca attacagtgt gctattcggc    780
ggagggacca agctgaccgt cctaggtcag cccaaggctg cccctcggt cactctgttc      840 ccgccgtccg cggccgctgg atccgaacaa aagctgatct cagaagaaga cctaaactca    900
catcaccatc accatcacta a                                              921

<210> SEQ ID NO 43
<211> LENGTH: 66
<212> TYPE: DNA
<213> ORGANISM: Artificial sequence
<220> FEATURE:
<223> OTHER INFORMATION: Nucleic acid encoding PelB leader sequence

<400> SEQUENCE: 43
atgaaatacc tattgcctac ggcagccgct ggcttgctgc tgctggcagc tcagccggcc     60
atggcg                                                                66

<210> SEQ ID NO 44
<211> LENGTH: 24
<212> TYPE: DNA
<213> ORGANISM: Artificial sequence
<220> FEATURE:
<223> OTHER INFORMATION: Nucleic acid encoding scFv linker

<400> SEQUENCE: 44
gaagaaggtg aatttcaga agca                                             24

<210> SEQ ID NO 45
<211> LENGTH: 30
<212> TYPE: DNA
<213> ORGANISM: Artificial sequence
<220> FEATURE:
<223> OTHER INFORMATION: Nucleic acid encoding c-myc tag

<400> SEQUENCE: 45
gaacaaaagc tgatctcaga agaagaccta                                      30

<210> SEQ ID NO 46
<211> LENGTH: 18
<212> TYPE: DNA
<213> ORGANISM: Artificial sequence
<220> FEATURE:
<223> OTHER INFORMATION: Nucleic acid encoding hexa-histidine tag

<400> SEQUENCE: 46
catcaccatc accatcac                                                   18

<210> SEQ ID NO 47
<211> LENGTH: 31
<212> TYPE: DNA
<213> ORGANISM: Artificial sequence
<220> FEATURE:
```

<223> OTHER INFORMATION: Oligonucleotide primer P41

<400> SEQUENCE: 47
ctgcaggggg cttttggga gtaaaaatgt g                                31

<210> SEQ ID NO 48
<211> LENGTH: 31
<212> TYPE: DNA
<213> ORGANISM: Artificial sequence
<220> FEATURE:
<223> OTHER INFORMATION: Oligonucleotide primer P42

<400> SEQUENCE: 48 cacatttta ctcccaaaaa gccccctgca g                                31

<210> SEQ ID NO 49
<211> LENGTH: 64
<212> TYPE: DNA
<213> ORGANISM: Artificial sequence
<220> FEATURE:
<223> OTHER INFORMATION: Oligonucleotide primer P34

<400> SEQUENCE: 49
catcacgata tcagaaccac cggagccgcc gctaccacct gaggacacgg tgaccagggt    60
tccc                                                                64

<210> SEQ ID NO 50
<211> LENGTH: 35
<212> TYPE: DNA
<213> ORGANISM: Artificial Sequence
<220> FEATURE:
<223> OTHER INFORMATION: Oligonucleotide primer P36

<400> SEQUENCE: 50
ccggccatgg cgcaggtcca gctggtacag tctgg                              35

<210> SEQ ID NO 51
<211> LENGTH: 9
<212> TYPE: PRT
<213> ORGANISM: Artificial sequence
<220> FEATURE:
<223> OTHER INFORMATION: glycine-serine linker

<400> SEQUENCE: 51

Gly Gly Ser Gly Gly Ser Gly Gly Ser
1               5

<210> SEQ ID NO 52
<211> LENGTH: 69
<212> TYPE: DNA
<213> ORGANISM: Artificial sequence
<220> FEATURE:
<223> OTHER INFORMATION: Oligonucleotide primer P35

<400> SEQUENCE: 52
ggtcaccgtc tcctcaggtg gtagcggcgg ctccggtggt tcttcctatg tgctgactca    60
gccatcctc                                                           69

<210> SEQ ID NO 53
<211> LENGTH: 56
<212> TYPE: DNA
<213> ORGANISM: Artificial sequence
<220> FEATURE:
<223> OTHER INFORMATION: ER retention signal

```
<400> SEQUENCE: 53
cctctagatt agtgatggtg atggtgatgg gatcctagga cggtcagctt ggtccc        56

<210> SEQ ID NO 54
<211> LENGTH: 4
<212> TYPE: PRT
<213> ORGANISM: Artificial sequence
<220> FEATURE:
<223> OTHER INFORMATION: ER retention signal

<400> SEQUENCE: 54

Lys Asp Glu Leu
1
```

ANTI-CD16 BINDING MOLECULES

The present invention relates to binding molecules that specifically bind to the human Fc gamma III receptor expressed on the surface of natural killer (NK) cells and macrophages (i.e. FcγRIIIA), and in particular binding molecules that specifically bind the A form FcγRIII but do not bind to the B form of FcγRIII, as well as to the use of such binding molecules in the diagnosis and treatment of disease. The invention further extends to polynucleotides encoding such binding molecules, host cells comprising such polynucleotides and methods of producing binding molecules of the invention using such host cells.

CD16 (also known as FcγRIII), a low affinity receptor for the Fc portion of some IgGs known to be involved in antibody-dependent cellular cytotoxicity (ADCC), is the best-characterized membrane receptor responsible for triggering of target cell lysis by NK cells (Mandelboim et al., 1999, PNAS 96:5640-5644). Human NK cells comprise approximately 15% of all lymphocytes and are defined phenotypically by their expression of CD56 and lack of expression of CD3 (Robertson and Ritz, 1990, Blood 76:2421-2438). The majority (approximately 90%) of human NK cells express CD56 at low density (CD56$^{dim}$) and FcγRIII (CD16) at a high level (Cooper et al., 2001, Trends Immunol. 22:633-640). Human FcγRIII exists as two isoforms, FcγRIIIA and FcγRIIIB, that share 96% sequence identity in their extracellular immunoglobulin-binding regions (van de Winkel and Capel, 1993, Immunol. Today 14(5):215-221).

FcγRIIIA is expressed on macrophages, mast cells, and NK cells as a transmembrane receptor. On NK cells, the alpha chain of FcγRIIIA associates with the immunoreceptor tyrosine-based activation motif (ITAM) containing FcεRI γ-chain and/or the T-cell receptor (TCR)/CD3 ζ-chain to mediate signalling (Wirthmueller et al., 1992, J. Exp. Med. 175:1381-1390). The interaction of FcγRIIIA with different combinations of homo- and hetero-dimers of the γ and ζ chains has been observed in NK cells, offering the possibility of different signalling pathways via variations of the FcγRIIIA complex in NK cells (Anderson et al., 1990, PNAS 87(6):2274-2278; Ackerly et al., 1992, Int. J. Cancer Suppl. 7:11-14).

FcγRIIIB is present on polymorphonuclear granulocytes (PMN) as a glycosyl-phosphatidylinositol (GPI)-anchored receptor (FcγRIIIB isoform), which cannot trigger tumour cell killing (van de Winkel and Capel, 1993, supra). In addition, FcγRIIIB exists as a soluble receptor in serum and upon binding to antibodies may trigger side-effects via the formation of immune complexes in vivo.

FcγR-expressing effector cells have been shown to be involved in destroying tumour cells via ADCC. This has lead to the development of several immunotherapeutic approaches to cancer therapy, which involve the use of FcγR activities, for example, tumour specific monoclonal antibodies can mediate destruction of tumour cells by ADCC induced via binding to FcγRs, and bi-specific molecules with one specificity for tumour cells and the other specificity for either an FcγRI on granulocytes or FcγRIII on NK cells have also been developed in efforts to improve effector cell recruitment (van Spriel et al., 2000 Immunol. Today, 21:391-397).

As cellular mediators of innate immunity, NK cells are professional cell killers and, unlike T cells, tend to exist in constitutively activated states not requiring additional (pre-) stimulation. In contrast, resting cytotoxic T-cells require activation via the binding of an antigen-MHC complex and subsequent co-stimulation via CD28. Thus, amongst the immune effector cells, the NK cell is one of the more attractive candidates for use in immunotherapy, and bi-specific antibodies with specificity to CD16 (FcγRIII) and HER-2/neu or CD16 and CD30 have been developed (Arndt et al., 1999 Blood 94:2562-2568; McCall et al., 2001 J. Immunol. 166:6112-6117).

The majority of anti-CD16 antibodies that have been produced to date, are unable to distinguish between the two CD16 isoforms, FcγRIIIA and FcγRIIIB, with the exceptions being monoclonal antibody (MAb) 1D3, which only binds to the form of CD16 expressed on neutrophils i.e. FcγRIIIB, and the monoclonal antibodies which recognise different allotypic forms of FcγRIIIB (Ory et al. 1989, J. Clin. Invest. 83:1676-81; Huizinga et al. 1990 Blood 75:213-7; Tamm & Schmidt 1996, J. Immunol. 1996 157:1576-1581). However, to date, there have been no examples of molecules that bind specifically to FcγRIIIA, the form expressed on NK cells, and not to FcγRIIIB.

An antibody specific for FcγRIIIA, however, would be particularly useful as a component of a bi- or multispecific binding molecule that is directed against disease-associated cells, as it would mainly recruit NK cells, and would not be bound by circulating soluble FcγRIIIB or diverted from NK cell binding by binding to neutrophils or activated eosinophils. To efficiently mediate NK-cell killing, the FcγRIIIA-specific antibody must not only bind NK cells but also activate them upon binding.

We have identified several new anti-CD16 scFvs, which exhibit this useful property, i.e. they have specificity for FcγRIIIA, they do not bind with specificity to FcγRIIIB and they are also able to activate NK cells upon binding.

It is also known that FcγRIIIA exhibits several allelic polymorphisms, in particular at positions 48 and 158 of the IgG binding domain. Previously described anti-CD16 antibodies have been shown to bind with different affinities to the different polymorphic forms of FcγRIIIA and work by Koene et al. (1997, Blood 90:1109-1114) attributes the difference in binding of some of these antibodies to the polymorphism at position 158. Since the gene frequencies of the FcγRIIIA$^{158F}$ allele and of the FcγRIIIA$^{158V}$ allele are approximately 0.6 and 0.4 respectively, it would be advantageous for any anti CD16A antibody to recognize both allelic forms, to ensure that in any given patient the anti-CD16A antibody would be capable of binding and activating the NK cell population.

Described herein is an anti-CD16A scFv which recognizes both FcγRIIIA$^{158V}$ and FcγRIIIA$^{158F}$ with approximately equal affinity, but which does not bind to FcγRIIIB.

The new scFvs described herein may thus be used to produce novel binding molecules, which may be used as therapeutic agents. The term "binding molecule" as used herein encompasses antibodies and antigen-binding fragments thereof, wherein said antibodies or antigen binding fragments selectively and specifically bind to FcγRIIIA and do not bind with specificity to FcγRIIIB, as well as fusion proteins of such antibodies or antigen-binding fragments, and protein conjugates comprising such antibodies or antigen-binding fragments.

Thus according to the first aspect of the invention, there is provided a binding molecule having specificity for at least one antigen, wherein the at least one antigen is FcγRIIIA and wherein the binding molecule does not specifically bind to FcγRIIIB.

In a preferred embodiment, the specificity for FcγRIIIA is provided by an antibody or antigen-binding fragment thereof. Accordingly, binding molecules of the invention may comprise, or in certain embodiments consist of, at least one antibody (or an antigen binding fragment thereof) which has specificity for FcγRIIIA but not FcγRIIIB.

Antibodies conferring specificity to FcγRIIIA may be naturally occurring antibodies, or they may be recombinant antibodies. Antibodies of the invention may be of any immunoglobulin class, e.g. they may be an IgA, IgD, IgE, IgG or IgM antibody. Preferably the antibody will be an IgG antibody. Antigen-binding fragments suitable for use in the invention may be naturally occurring or recombinant and include immunoglobulin light chains, immunoglobulin heavy chains, $V_H$ domains, $V_L$ domains, Fvs, single chain antibodies (including scFvs), Fabs, di-Fabs, Fab's, F(ab')$_2$s, and CDRs. The skilled man will be very familiar with such antigen-binding fragments and their preparation. For the avoidance of doubt the term single chain antibody as used herein refers to a genetically engineered single chain molecule comprising the variable region of a light chain and the variable region of a heavy chain, linked by a suitable flexible polypeptide linker. Examples of single chain antibodies include a scFv and a diabody.

In one embodiment, the antibody or antigen-binding fragment conferring specificity to FcγRIIIA will comprise at least one human CDR, preferably selected from the CDRs described in Table 1 below.

TABLE 1

Amino acid sequences of human light and heavy chain CDRs from scFvs that selectively and specifically bind to FcγRIIIA and do not bind with specificity to FcγRIIIB

| Chain | CDR1 | CDR2 | CDR3 |
|---|---|---|---|
| 1. Heavy Chain | TSYYMH (SEQ ID NO 17) | IINPSGGSTSYAQKFQG (SEQ ID NO 18) | GSAYYYDFADY (SEQ ID NO 19) |
| 2. Light Chain | SGDKLEEKYVS (SEQ ID NO 20) | QDNKRPS (SEQ ID NO 21) | QVWDNYSVL (SEQ ID NO 22) |
| 3. Light Chain | GGNNIESRNVH (SEQ ID NO 23) | RDNNRPS (SEQ ID NO 24) | QVWDNYTVL (SEQ ID NO 25) |
| 4. Light Chain | GGNNIGSKNVH (SEQ ID NO 26) | RDSNRPS (SEQ ID NO 27) | QVWDNYIVL (SEQ ID NO 28) |
| 5. Light Chain | EGNNIGSKNVH (SEQ ID NO 29) | DDSDRPS (SEQ ID NO 30) | QVWDNYSVL (SEQ ID NO 22) |
| 6. Light Chain | GGNNIGSKNVH (SEQ ID NO 26) | RDSSRPS (SEQ ID NO 31) | QVWDDYIVV (SEQ ID NO 32) |
| 7. Light Chain | GANDIGKRNVH (SEQ ID NO 33) | QDNKRPS (SEQ ID NO 21) | QVWDNYSVL (SEQ ID NO 22) |
| 8. Light Chain | GGHNIGSKNVH (SEQ ID NO 34) | QDNKRPS (SEQ ID NO 35) | QVWDNYSVL (SEQ ID NO 22) |

The skilled man will appreciate that antibodies and antigen-binding fragments thereof, with the exception of single CDRs, in general comprise three light chain CDRs and/or three heavy chain CDRs. Accordingly in further embodiments, the antibody or antigen binding fragment with specificity for FcγRIIIA comprises three human light chain CDRs and/or three human heavy chain CDRs. Preferably the human light chain CDR 1 will have an amino acid sequence selected from SEQ ID NO 20, SEQ ID NO 23, SEQ ID NO 26, SEQ ID NO 29, SEQ ID NO 33, and SEQ ID NO 34, the human light chain CDR 2 will have an amino acid sequence selected from SEQ ID NO 21, SEQ ID NO 24, SEQ ID NO 27, SEQ ID NO 30, SEQ ID NO 31 and SEQ ID NO 35 and the human light chain CDR3 will have an amino acid selected from SEQ ID NO 22, SEQ ID NO 25, SEQ ID NO 28 and SEQ ID NO 32. Preferably the human heavy chain CDR1 will have the amino acid sequence of SEQ ID NO 17, the human heavy chain CDR2 will have the amino acid sequence of SEQ ID NO 18 and the human heavy chain CDR3 will have the amino acid sequence of SEQ ID NO 19.

Where the antibody or antigen-bindings fragment comprises or consists of the variable domain of a light chain it may have one of the following amino acid sequences:

```
SEQ ID NO 10:
SYELMQPPSVSVSSGQTASIPCSGDKLEEKYVSWYQQRPGQSPVLVIYQD

NKRPSGIPERFSGSNSGNTATLTISGTQAMDEADYYGQVWDNYSVLFGGG

TKLTVL;

SEQ ID NO 11:
SYELTQPLSESVAQGQTARITCGGNNIESRNVHWYQQKPGQAPVLVIYRD

NNRPSGIPERFSGSNSGNMATLTISRAQAGDAADYYCQVWDNYTVLFGGG

TKLTVL;

SEQ ID NO 12:
SYELTQPPSVAVAPGKTARITCGGNNIGSKNVHWYQQKPGQAPVLVIYRD

SNRPSGIPERFSGSNSGNTATLTISRAQAGDEADFYCQVWDNYIVLFGGG

TKLTVL;

SEQ ID NO 13:
QAVLTQPPSVSVAPGQTARIPCEGNNIGSKNVHWYRQKPGQVPVLVMYDD

SDRPSGIPERFSGSNSGNTATLTISGTQAMDEADYYCQVWDNYSVLFGGG

TKLTVL;

SEQ ID NO 14:
QPVLTQPLSVSVAPGQTARITCGGNNIGSKNVHWYQQKPGQAPVLVIYRD

SSRPSGIPERLSGSNSGDTATLTISRAQAGDEADYYCQVWDDYIVVFGGG

TKLTVL;
```

-continued

SEQ ID NO 15:
SYELTQPPSVSVTPGQTATITCGANDIGKRNVHWYQQRPGQSPVLVIYQD

NKRPSGIPERFSGSNSGNTATLTISGTQAMDEADYYCQVWDNYSVLFGGG

TKLTVL;

SEQ ID NO 16:
QPVLTQPSSVSVAPGQTATISCGGHNIGSKNVHWYQQRPGQSPVLVIYQD

NKRPSGIPERFSGSNSGNTATLTISGTQAMDEADYYCQVWDNYSVLFGGG

TKLTVL.

Where the antibody or antigen-binding fragment comprises or consists of the variable domain of a heavy chain, it may have the following amino acid sequence (SEQ ID NO 9): EVQLVQSGAEVKKPGESLKVSCKASGYT-FTSYYMHWVRQAPGQGLE WMGIINPSGGSTSYAQK-FQGRVTMTRDTSTSTVYMELSSLRSED-TAVYYCARGS AYYYDFADYWGQGTLVTVSS.

In a preferred embodiment, the antibody or antigen-binding fragment that provides specificity to FcγRIIIA will be fully human.

In further preferred embodiments the binding molecule of the invention will be capable of activating human cells expressing FcγRIIIA upon binding to the FcγRIIIA expressed on such cells, i.e. the binding molecule will be capable or eliciting a biological response, in particular a signaling response, upon binding to FcγRIIIA. Preferably the binding molecule will also be capable of triggering cell killing, in a manner analogous to antibody-dependent cellular cytotoxicity (ADCC), by virtue of its binding to such cells.

In order to test whether binding molecules of the invention are capable of activating human cells expressing FcγRIIIA, they may be tested for their ability to elicit calcium mobilization in peripheral blood NK cells, for example as described herein in the Examples. The ability of binding molecules of the invention to trigger NK-cell mediated cytotoxicity may also be tested as described herein in the Examples, using for example a calcein-release assay to detect re-directed cell lysis using freshly isolated NK cells.

The present invention also provides binding molecules that not only have specificity for FcγRIIIA whilst lacking specificity for FcγRIIIB, but which also have specificity for one or more additional antigens. Thus binding molecules of the invention may be multispecific. The term multispecific as used herein means that a binding molecule of the invention, whilst lacking specificity for FcγRIIIB, has at least two specificities, one of which is for FcγRIIIA. Multispecific binding molecules of the invention thus encompass at least bi-specific, tri-specific, and tetra-specific molecules, such as for example, bi-specific antibodies including single-chain diabodies, (scFv)$_2$, tandem diabodies (TandAbs); tri-bodies (tri-specific antibody); tetra-bodies (tetraspecific antibody); and flexibodies (see Le Gall et al. 1999 FEBS Letts 453:164-168 and WO 03/025018).

By virtue of their multispecificity, binding molecules according to this aspect of the invention may target macrophages or NK cells to further antigens or even to cells bearing such antigens, so that the antigen or cell bearing the antigen may be eradicated via phagocytosis or NK cell mediated cell killing. For example, a binding molecule of the invention may have additional specificity for one or more tumor specific antigens and can thus target NK-cells to the tumor cell. Activation of the NK cell caused by the binding molecule binding to FcγRIIIA will lead to killing of the tumor cells. In this manner binding molecules of the invention may be used to treat and/or eliminate diseased cells and infectious agents (such as for example, bacteria, fungi, mycoplasmas, viruses, parasites, prions), depending on the additional specificity or specificities of the binding molecule.

Thus in a further aspect the invention provides a binding molecule as described hereinbefore, wherein the binding molecule has specificity for at least one additional antigen. In one embodiment the at least one additional antigen is a cell-surface antigen. Examples of cell surface antigens to which binding molecules according to this embodiment of the invention exhibit specificity are CD19, CD20, CD30, the laminin receptor precursor protein (also known as the oncofoetal antigen immature laminin receptor OFA-iLR), EGFR1 (also known as HER-1, ErbB1), EGFR2 (also known as HER-2, ErbB2, neu), EGFR3 (also known as HER-3), Ep-CAM, PLAP (placental alkaline phosphatase), Thomsen-Friedenreich (TF) antigen, MUC-1 (mucin), IGFR, IL4-R alpha, IL13-R, FcεRI and CD5.

In a further embodiment, the at least one additional antigen is an antigen from an infectious agent, for example, the antigen may be secreted from or expressed on the outer surface of a host cell, infected cell, bacterium, fungus, mycoplasma, parasite or virus, or it may be released upon lysis of such an infectious agent. For example, a binding molecule of the invention may have additional specificity for a viral protein such as gp34 or gp68 on the surface of CMV-infected cells, or for haemaglutinin on the presence of the influenza virus, and may thus target either a virally infected cell or the virus directly. Alternatively, where the infectious agent is a prion, the prion protein per se may be the antigen.

In a further embodiment the at least one additional antigen is an allergen, or a molecule involved in the response of the body to an allergen, such as for example circulating IgE, or the FcεRI receptor on (in particular) mast cells.

Preferably, in binding molecules according to this aspect of the invention, the specificity for the at least one additional antigen is provided by an antibody or an antigen-binding fragment thereof. As described above, the skilled man will be familiar with the types of antibodies (IgA, IgD, IgE, IgG and IgM) and with antigen-binding fragments derived from such antibodies (for example, immunoglobulin light chains, immunoglobulin heavy chains, $V_H$ domains, $V_L$ domains, Fvs, scFvs, Fabs, di-Fabs, Fab's, F(ab')$_2$s, and CDRs) which may also be used in this aspect of the invention. In one preferred embodiment the antibody will be an IgG antibody.

Multispecific, and in particular bispecific, binding molecules of the invention may thus have any of the following formats: bispecific IgGs, IgG-scFv$_2$, (scFv)$_4$-IgG, (Fab')$_2$, (scFv)$_2$, (dsFv)$_2$, Fab-scFv fusion proteins, (Fab-scFv)$_2$, (scFv)$_2$-Fab, (scFv-C$_H$2-C$_H$3-scFv)$_2$, bibody, tribody, bispecific diabody, disulfide-stabilized (ds) diabody, 'knob-into-whole' diabody, single-chain diabody (scDb), tandem diabody (TandAb), flexibody, DiBi miniantibody, [(scFv)$_2$-Fc]$_2$, (scDb-C$_H$3)$_2$, (scDb-Fc)$_2$, Di-diabody, Tandemab (reviewed in Kipriyanov & Le Gall, 2004, Curr. Opin. Drug Discov. Devel., 7:233-242 and Marvin and Zhu, 2005, Acta Pharmacol. Sin., 26:649-658). In preferred embodiments the binding molecule will be TandAb or Flexibody. Unlike many other bispecific antibody formats, the TandAb is a homodimer comprising only antibody variable domains, and its formation is determined by the association of complementary $V_H$ and $V_L$ domains located on different polypeptide chains. The TandAb is twice the size of the diabody and (scFv)$_2$, is able to bind bivalently both effector and target cells and possesses improved pharmacokinetic characteristics relative to the diabody and (scFv)$_2$ e.g. it has greater stability and enhanced biological activity both in vitro and in vivo (Kipriyanov et al., 1999, J. Mol. Biol., 293:41-56; Cochlovius et al., 2000, Cancer Res., 60:4336-4341; Reusch et al., 2004, Int. J. Cancer, 112:509-518.). The interchain pairing of the cognate $V_H$ and $V_L$ domains of the same specificity could be also used for the formation of bispecific scFv$^B$-diabody$^A$-scFv$^B$ tandem molecules, so-called 'flexibodies' (A and B may have the same or different specificity). Depending on the tightness of association of complementary domains involved into the interchain pairing and on the length of the linker separating them, dimers, trimers and even tetramers of bispecific single-chain molecules may be formed.

Examples of antibodies and antigen-binding fragments, which may be used in this aspect of the invention and which exhibit specificity for CD19, CD20, CD30, the laminin receptor precursor protein, EGFR1, EGFR2, EGFR3, Ep-CAM, PLAP, Thomsen-Friedenreich (TF) antigen, MUC-1 (mucin), IGFR, CD5, IL4-R alpha, IL13-R, FcεRI and IgE, are described in the art, as are antibodies to infectious agents (see for example, EP-A-1314741, Reff et al. 1994 Blood 83:435-445, EP-A-1005870, WO 01/92340, U.S. Pat. No. 6,033,876, WO 86/03223, Buto et al. 1997 Int. J. Biol. Markers 12:1-5, U.S. Pat. No. 6,699,473, WO 98/50433, U.S. Pat. No. 5,770, 195, EP-A-0502812, Carter et al. 1992 PNAS 89:4285-4289, U.S. Pat. No. 5,968,511, WO 04/106383, Nouri et al. 2000 BJU Int. 86:894-900, EP-A-0429242, Ravn et al. 2004 J. Mol. Biol. 343:985-996, Dahlenborg et al. 1997 Int. J. Cancer 70:63-71, WO 88/05054, WO 02/053596, WO 04/071529, Studnicka et al. 1994 Protein Eng. 7:805-814, Presta et al. 1993 J. Immunol. 151:2623-2632). Where these citations provide amino acid sequences of, or nucleic acid sequences encoding, such antibodies or antigen-binding fragments, the skilled man will be able to utilize such sequences directly in the production of binding molecules of the invention. Where these citations describe hybridomas or cell lines producing such antibodies or antigen-binding fragments, the skilled man will be able to obtain the nucleic acid sequences encoding the desired antibody or antigen-binding fragment from the appropriate hybridoma or cell line using standard molecular biology techniques, and once obtained the nucleic acid sequences may be used in the construction of binding molecules of the invention.

A further aspect of the invention provides for a binding molecule according to any one of the aspects or embodiments described hereinbefore, which is capable of binding to the FcγRIIIA$^{158F}$ allele and the FcγRIIIA$^{158V}$ allele with approximately the same affinity, i.e. the affinity of the binding molecule for the two 158 alleles of FcγRIIIA differs by no more than two-fold. In preferred embodiments according to this aspect of the invention the specificity for FcγRIIIA will be provided by an antibody or antigen binding fragment derived from the 4-LS21 scFv described herein. In particularly preferred embodiments binding molecules according to this aspect of the invention will be in a TandAb format and will comprise antigen binding fragments derived from the 4-LS21 scFv described herein as well as antigen binding fragments having specificity for CD19 or CD30.

The skilled man will appreciate that where it is intended that binding molecules of the invention are to be used in the treatment and/or therapy of humans, the potential immunogenicity of the binding molecule should be minimized. Accordingly, where the specificity for FcγRIIIA and/or the additional antigen(s) is(are) provided by an antibody or antigen-binding fragment, it is preferred that the antibody or antigen-binding fragment is chimeric, CDR-grafted, humanized or fully human. More preferably the antibody or antigen-binding fragment will be humanized or fully human. The use of standard molecular biological techniques to effect the humanization of antibodies is now routine in the art, and provided with a non-human antibody sequence, the skilled man would readily be able to produce a humanized version of such an antibody. The term "fully human" as used herein insofar as it relates to an antibody or antigen-binding fragment means that the amino acid sequences of the antibody or antigen-binding fragment are derived from (i.e. originate or may be found in) humans.

Another technique which may be employed either as an alternative, or in addition, to the methods described above for reducing immunogenicity, is that of deimmunisation. Deimmunisation technology involves the identification and removal of T helper (Th) cell epitopes from antibody and other protein biological therapeutic agents. Th cell epitopes comprise short peptide sequences within proteins that have the capacity to bind to MHC class II molecules. The peptide-MHC class II complexes can be recognized by T cells and can trigger the activation and differentiation of Th cells, which is required to initiate and sustain immunogenicity through interaction with B cells, thus resulting in the secretion of antibodies that bind specifically to the administered biological therapeutic agent. For antibody deimmunisation, the Th-cell epitopes are identified within the antibody sequence, for example by a computer-based method for predicting the binding of peptides to human MHC class II molecules (see Altuvia et al., 1995, J. Mol. Biol., 249:244-2450, and Schueler-Furman et al., 2000, Protein Sci., 9:1838-1846). To avoid recognition by T cells, the Th cell epitopes thus identified are eliminated from the protein sequence by amino acid substitutions. This may be achieved through the use of standard molecular biology techniques, such as for example site-directed mutagenesis to alter the nucleic acid sequence encoding the Th cell epitope in the therapeutic protein. In this way, an antibody or antigen-binding fragment may be modified so that HAMA (Human anti mouse antigenic) and/or anti-idiotypic response(s) are reduced or avoided (Bander et al., 2003, Semin. Oncol., 30:667-676; Nanus et al., 2003, J. Urol., 170: S84-S89). Thus in further embodiments, binding molecules of the invention are modified to remove any Th cell epitopes present in their sequence. Such binding molecules are referred to herein as deimmunised binding molecules.

In a further aspect, binding molecules of the invention comprise a further functional domain. This functional domain may confer effector properties on the binding molecule, for example, the functional domain may be a FcR-binding peptide or the Fc domain of an antibody which, through their capability to bind to Fc receptors, confer effector properties on the binding molecule. Alternatively, the functional domain may be an enzyme that is capable of converting a pro-drug to an active drug. In this way binding molecules of the invention may be used in antibody-dependent enzyme pro-drug therapy (ADEPT). In a further embodiment, the functional domain is a protein or peptide that confers an increased serum half-life on the binding molecule. An example of such a protein is serum albumin or the Fc portion of IgG, which may increase serum half-life of the binding molecule by virtue of its ability to bind to FcγRn (the neonatal Fc receptor). In a further embodiment the functional domain may be a cytokine.

In a further aspect, binding molecules of the invention may be conjugated to a labeling molecule, or a toxin. Where the labeling molecule or toxin is a protein, conjugation to the binding molecule may occur through a peptide bond or through chemical conjugation. Thus a binding molecule according to this aspect of the invention may be in the form of a fusion protein where the labeling molecule or toxin is linked to the binding molecule by a peptide bond, preferably by a peptide linker, or it may be in the form of a chemical conjugate. For the avoidance of doubt, the term conjugation is used herein to mean that two components are physically linked together via a chemical bond, which includes a peptide bond (thus conjugates include fusion proteins), ester linkage, or disulphide bridge.

Conjugation of a binding molecule of the invention to a labeling molecule, such as a radiolabel or a fluorescent or luminescent (including chemiluminescent) label allows the binding molecule to be used as an immunological staining reagent. Such a reagent may be used in detecting, for example, tissue-infiltrating NK cells, macrophages or mast cells expressing FcγRIIIA, or, where the binding molecule exhibits specificity for an additional antigen, in detecting NK-cell-binding molecule-additional antigen complexes. Detection of the latter may be particularly useful in the diagnosis of disease or in the monitoring of disease progression or remission.

Where a binding molecule of the invention is conjugated to a toxin molecule, such as a ribosyl transferase, serine protease, guanyl cyclase activator, calmodulin-dependent adenyl cyclase, ribonuclease, DNA alkylating agent or mitosis inhibitor (e.g. doxorubicin) and the like, it may be used to target and kill NK cells and macrophages. Such a binding molecule may thus be used as an immunosuppressive agent. The skilled man will appreciate that in this aspect of the invention, it is preferred that the binding molecule exhibits specificity for only one antigen, i.e. FcγRIIIA. Suppression of the immune system may also be achieved using binding molecules comprising or consisting of a monovalent antigen binding fragment which binds selectively and specifically to FcγRIIIA. Such monovalent binding molecules are preferred as they will act as molecules that block the FcγRIIIA receptor, will not be cross-linked and will thus not activate the NK-cell or macrophage. Preferred monovalent anti-FcγRIIIA antigen-binding fragments include, scFv, Fab, $V_H$, $V_L$ and a CDR.

The skilled man will appreciate that as an alternative to being tagged with a labeling molecule or toxin via chemical conjugation, peptide labels or peptide toxins may also be used. For example, the binding molecule of the invention may be expressed as a fusion protein with an N- or C-terminal peptide tag such as a tetra-penta- or hexa-histidine tag, a c-myc tag or the like.

Binding molecules of the invention may be produced by expressing nucleic acids encoding them in any suitable protein expression system. Thus in a further aspect the invention provides polynucleotides encoding binding molecules of the invention. Polynucleotides that are particularly suitable for use in this aspect of the invention will encode the CDRs described in Table 1 above. In particular, the skilled man armed with the amino acid sequence of the light and heavy chain CDRs from table 1, will be able to derive polynucleotide sequences encoding the various light and heavy chain CDRs from the following nucleic acid sequences:

```
SEQ ID NO 1:
gaggtccagctggtacagtctggagcagaggtgaaaaagcccggggagtctctgaaggtttcctgcaaggcatctggatacac cttcaccagctactatatgcactgggtgcgacaggcccctggacaagggcttgagtggatgggaataatcaaccctagtggtgg tagcacaagctacgcacagaagttccagggcagagtcaccatgacccgggacacgtccacgagcacagtctacatggagctt agcagcctgagatctgaggacacggccattactgtgctagaggtagtgcttattactacgatttttgctgactactgggcca gggaaccctggtcaccgtctcctca;

SEQ ID NO 2:
tcctatgagctgatgcagccaccctcagtgtccgtgtcctcaggacagacagccagcatcccctgctctggagataaattggag gaaaaatatgtttcctggtatcaacagaggccaggccagtcccctgtgttggtcatttatcaggataataagcggccctcagggat ccctgagcgattctctggctccaactctgggaacacagccactctgaccatcagcgggacccaggcgatggatgaggctgact actattgtcaggtgtgggacaattacagtgtgctattcggcggagggaccaagctgaccgtccta SEQ ID NO 3:
tcctatgagctgacacagccactctcagagtcagtggcccagggacagacggccaggattacctgtggggaaacaacattga aagtagaaatgttcactggtaccagcagaagccaggccaggcccctgtgttggtcatctatagggataacaaccggccctctgg gatccctgagcgattctctggctccaattcggggaacatggccaccctgaccatcagcagagcccaagccggggatgcagctg actattactgtcaggtgtgggacaactacactgtgctattcggcggagggaccaagctgaccgtccta SEQ ID NO 4:
tcctatgagctgacacagccaccctcagtggcagtggcccaggaaagacggccaggattacctgtggggaaacaacattg gaagtaaaaatgtgcactggtaccagcagaagccaggccaggcccctgtgctggtcatctatagggatagcaaccggccctct gggatccctgagcgattctctggctccaactcggggaacacggccaccctgaccatcagcagagcccaagccggggatgag gctgactttattgtcaggtgtgggacaactatattgtgctgttcggcggagggaccaagctgaccgtcctg SEQ ID NO 5:
caggctgtgctgactcagccgccctcagtgtcagtggcccaggacagacggccaggattccctgtgagggaaacaacattg gaagtaaaaatgtccactggtatcggcagaagccaggccaggtccctgtcctggtcatgtatgatgatagcgaccggccctcag ggatccctgagcgattctctggctccaactctgggaacacagccactctgaccatcagcgggacccaggcgatggatgaggct gactactattgtcaggtgtgggacaattacagtgtgctattcggcggagggaccaagctgaccgtccta
```

-continued

SEQ ID NO 6:
cagcctgtgctgactcagccactctcagtgtcagtggccccgggacagacggccaggattacctgtgggggaaacaacattgg aagtaaaaatgtgcactggtaccagcagaagccaggccaggcccctgtactggtcatctatagggacagcagccggccctctg ggatccctgagcgactctctggctccaactcggggga cacggccaccctgaccatcagcagagcccaggccggggatgagg ctgactattactgtcaggtgtgggacgactacattgtggtcttcggcggagggaccaagctgaccgtccta SEQ ID NO 7:
tcctatgagctgacacagccaccctcggtgtcagtgacccaggacagacggccacgattacctgcggggcaaacgacattg gaaaagaaatgtccactggtaccaacagaggccaggccagtcccctgtgttggtcatttatcaggataataagcggccctcag ggatccctgagcgattctctggctccaactctgggaacacagccactctgaccatcagcgggacccaggcgatggatgaggct gactactattgtcaggtgtgggacaattacagtgtgctattcggcggagggaccaagctgaccgtccta SEQ ID NO 8:
cagcctgtgctgactcagccatcctcggtgtcagtggccccaggacagacggccacgatctcctgtgggggacacaacattgg gagtaaaaatgtgcactggtaccagcagaggccaggccagtcccctgtgttggtcatttatcaggataataagcggccctcagg gatccctgagcgattctctggctccaactctgggaacacagccactctgaccatcagcgggacccaggcgatggatgaggctg actactattgtcaggtgtgggacaattacagtgtgctattcggcggagggaccaagctgaccgtccta SEQ ID NO 1 encodes the heavy chain variable region from a human scFv that selectively and specifically binds to FcγRIIIA but which does not bind with specificity to FcγRIIIB. SEQ ID NOs 2-8 encode light chain variable regions from human scFvs that selectively and specifically bind to FcγRIIIA, but which do not bind with specificity to FcγRIIIB. Accordingly, SEQ ID NOs 1 to 8 are also examples of polynucleotides of the invention, and may be used in producing further binding molecules of the invention.

Polynucleotides encoding multispecific binding molecules of the invention, in particular bi-specific binding molecules, may be constructed as described in WO 03/025018, using nucleic acids encoding the $V_H$ and $V_L$ domains of an antibody which binds selectively and specifically to FcγRIIIA but which does not bind specifically to FcγRIIIB, in combination with nucleic acids encoding the $V_H$ and $V_L$ domains of an antibody having specificity for the additional antigen.

In order for a binding molecule to be expressed in a suitable protein expression system the polynucleotide encoding the binding protein will be operably linked to a suitable promoter, and optionally a suitable transcription terminator. This may be achieved by introducing a polynucleotide of the invention into the genome of a host, and utilising a promoter present within the genome to drive expression of the polynucleotide. Alternatively, a polynucleotide of the invention may be introduced into host cells on a vector comprising the polynucleotide operably linked to promoter and optionally a terminator region. Such vectors form yet a further aspect of the invention.

In general, the promoter to which the polynucleotide encoding the binding molecule is operably linked in the vector, will be any promoter capable of driving expression of the binding molecule in the host cell into which the polynucleotide and vector are to be introduced. Thus, if it is desired that the binding molecule be expressed in a bacterial cell, the promoter will be operable in that bacterial cell. Similarly if it is desired that the binding molecule be expressed in a fungal expression system the promoter will be operable in a fungal cell and the same logic prevails if the construct is to be introduced into a mammalian cell culture expression system, an insect cell expression system or a plant expression system. Where polynucleotides of the invention are operably linked to a suitable transcriptional terminator region, this will be one that mediates the termination of transcription in the host cell in which the binding molecule of the invention is to be expressed. Transcriptional terminator regions suitable for this purpose are described in the art.

In preferred embodiments, the polynucleotide of the invention may also be operably linked to a signal sequence, which is capable of directing expression of the binding molecule to a desired cellular or extracellular location. For example, in some embodiments it may be desirable to secrete the binding molecule from the host cell in which it is expressed. Where this is the case, the signal sequence will encode a secretion signal. Suitable bacterial secretion signals are described in the art and one such example is the PelB leader sequence. In other embodiments, for example, those involving expression in eukaryotes, it may be desirable to retain expression of the binding molecule in the endoplasmic reticulum (ER). In this case the signal sequence will comprise an ER retention sequence encoding the "KDEL" (SEQ ED NO 54) motif, and in particular encoding the sequence "SEKDEL" (SEQ ID NO 55).

Polynucleotides of the invention may also be codon optimised according to methods readily available in the art, with the codon bias being altered to suit the particular expression host chosen.

Polynucleotides and vectors of the invention may be introduced into host cells using any appropriate methodology. In eukaryotic cells such techniques include calcium phosphate transfection, DEAE-Dextran, electroporation, particle bombardment, liposome-mediated transfection or transduction using retrovirus, adenovirus or other viruses, such as vaccinia or, for insect cells, baculovirus. In bacterial cells, suitable techniques may include calcium chloride transformation, electroporation or transfection using bacteriophage. In plant cells suitable techniques include *Agrobacterium* mediated transformation, electroporation, microinjection of plant cells and protoplasts, microprojectile bombardment, bacterial bombardement in particular the "fibre" or "whisker" method, depending upon the particular plant species being transformed. Thus in a further aspect the invention provides host cells comprising polynucleotides or vectors of the invention. Host cells from the organisms described below and which comprise polynucleotides or vectors of the invention are thus to be considered as specific embodiments of this aspect.

Suitable expression systems for expression of binding molecules of the invention include microbial expression systems such as bacterial (e.g. *E. coli, Bacillus* expression systems) and fungal systems e.g. yeasts (such as, for example, *Saccharomyces cerevisiae, Schizosaccharomyces pombe, Pichia* species, *Hanensula* species), and other fungal expression systems (e.g. filamentous fungal expressions systems derived from *Aspergillus* species, *Trichoderma reesei*, and *Neurospora crassa*); mammalian expression systems e.g. CHO cells, NS0 cells, HEK 293 cells; insect cell expression systems and plant expression systems. Safflower is particularly preferred as a plant expression system. The skilled man will be familiar with these expression systems, which are described fully in the art.

The present invention also provides methods for the production of binding molecules of the invention. Thus in a further aspect there is provided a method for the production of a binding molecule as described herein, wherein said method comprises introducing into a host cell a polynucleotide or vector of the invention and culturing said host cell under conditions whereby the binding molecule is expressed. Conditions for the growth and maintenance of host cells, and for mediating the expression of binding molecules of the invention from such host cells, are described fully in the art. In one embodiment the method will further comprise the isolation and optionally further purification of the binding molecule.

Where a binding molecule of the invention comprises a labelling molecule or a toxin molecule that has been chemically conjugated to the binding molecule, the conjugated binding molecule may be produced by introducing a polynucleotide or vector of the invention into a host cell, culturing the host cell under conditions whereby a binding molecule of the invention is expressed, isolating the expressed binding molecule and conjugating the isolated binding molecule with an appropriate label or toxin. Typically the conjugation step will involve the use of heterobifunctional agents which result in disulphide or thioether linkages as described in the art (see for example, Hermanson, G. T. "Bioconjugate Techniques" Academic Press, London, 1996, for standard methodologies relating to the use of cross-linking reagents).

The skilled man will appreciate that with some embodiments of the invention it may be desirable to increase the circulatory half-life if the binding molecule in the body. This may be achieved in various ways, for example, through constructing the binding molecule as a fusion protein with, for example, albumin, as described hereinbefore. Further methods of increasing serum half-life of a molecule are well known and include for example, pegylation, sialylation, and glycosylation. Accordingly the present invention encompasses binding molecules as described herein, which have been pegylated, sialylated or glycosylated.

The present invention also comprises compositions comprising a binding molecule and at least one additional component. For example, the skilled man will appreciate that in isolating binding molecules from host cells post expression, compositions may be obtained which comprise substantially purified binding molecule but which also contain an impurity, a diluent, a buffer or the like. Such intermediate compositions may be directly suitable for further use, or the binding molecule may be further purified therefrom.

Compositions of the invention may also comprise a binding molecule of the invention in combination with any suitable pharmaceutically acceptable carrier, excipient, diluent and/or stabiliser. The skilled man will be familiar with such components, which are described in the art. Preferably such a composition will be in any form suitable for administration to a patient, in particular in a form suitable for parenteral administration, for example by injection or infusion.

Where the composition is for injection or infusion it may take the form of a suspension, solution or emulsion in an oily or aqueous vehicle and it may contain formulatory agents such as suspending, preservative, stabilising and/or dispersing agents. Alternatively the binding molecule or composition may be in dry form, for reconstitution before use with an appropriate sterile liquid.

Binding molecules and compositions of the invention, in particular multispecific binding molecules and compositions containing the same, may be used in the diagnosis and/or treatment of disease, such as for example, autoimmune disease, inflammatory disease, infectious disease (including graft-versus-host disease), allergy and cancer (e.g. non-Hodgkin's lymphoma; chronic lymphocytic leukaemia; Hodgkin's lymphoma/disease; solid tumours e.g. those occurring in breast cancer, ovarian cancer, colon cancer, cancer of the kidney, or cancer of the bile duct; minimal residual disease; metastatic tumours e.g. those metastasising in the lungs, bones, liver or brain).

Multispecific binding molecules of the invention wherein the at least one additional specificity is towards the CD19 or CD20 antigen may be of particular use in the treatment of non-Hodgkin's lymphoma.

Multispecific binding molecules wherein the at least one additional specificity is towards EGFR1 may be of particular use in the treatment of cancers wherein EGFR1 expression is up-regulated or altered, for example in cancers of the breast, bladder, head and neck, prostate, kidney, non-small cell lung cancer, colorectal cancer and glioma.

Multispecific binding molecules wherein the at least one additional specificity is towards TF-antigen may be particularly useful in treating breast or colon cancer and/or liver metastases.

Multispecific binding molecules wherein the at least one additional specificity is towards CD30 may be particularly useful in treating Hodgkin's disease.

Multispecific binding molecules wherein the at least one additional specificity is towards the alpha chain of the IL4 receptor (IL4R alpha) may be particularly useful in treating solid tumors, in particular carcinomas of the breast, ovaries, renal system, head and neck, malignant melanoma and AIDS related Kaposi's sarcoma.

Multispecific binding molecules wherein the at least one additional specificity is towards EGFR3/HER3 and/or EGFR2/neu may be particularly useful in treating breast cancer.

Multispecific binding molecules wherein the at least one additional specificity is towards IGFR may be particularly useful in treating prostate cancer, colorectal cancer, ovarian cancer or breast cancer.

Multispecific binding molecules wherein the at least one additional specificity is towards CD5 may be particularly useful in treating chronic lymphocytic leukaemia Multispecific binding molecules wherein the at least one additional specificity is towards MUC-1 may be particularly useful in the treatment of gastric cancer and ovarian cancer.

Multispecific binding molecules wherein the at least one additional specificity is towards EpCAM may be particularly useful in the treatment of carcinomas of the colon, kidney, and breast.

Multispecific binding molecules wherein the at least one additional specificity is towards PLAP may be of particular use in the treatment of ovarian or testicular cancer.

Multispecific binding molecules wherein the at least one additional specificity is towards OFA-iLR may be particularly useful in the treatment of metastatic tumours.

In a further aspect the present invention provides the use of a binding molecule as described hereinbefore in the manufacture of a medicament for the treatment of autoimmune disease, inflammatory disease, infectious disease, allergy or cancer (e.g. non-Hodgkin's lymphoma; chronic lymphocytic leukaemia; Hodgkin's lymphoma; solid tumours e.g. those occurring in breast cancer, ovarian cancer, colon cancer, cancer of the kidney, or cancer of the bile duct; minimal residual disease; metastatic tumours e.g. those metastatising in the lungs, bones, liver or brain). Where specified multispecific binding molecules have been described above as having a particular utility in the treatment of a specified disease, these binding molecules may also be used in the manufacture of a medicament for that specified disease.

In yet a further aspect, binding molecules of the invention may be used as a reagent to stain cells expressing FcγRIIIA. Where the binding molecule has specificity for at least one further antigen, it may be used as the reagent by which the FcγRIIIA-expressing cell-binding molecule-antigen complex can be identified. Binding molecules of the invention may also be used to analyse and type patient samples ex vivo, as a biomarker, and to isolate NK cells for ex-vivo therapy.

Thus in a further aspect, there is provided a kit comprising a binding molecule as described hereinbefore and means for detecting the binding molecule when bound to FcγRIIIA. Where the binding molecule is radiolabeled or labelled with a chemiluminescent label, the detection means may comprise film sensitive to the radio- or chemiluminescent label. Where the binding molecule is tagged with a histidine or c-myc tag, the kit may comprise an antibody which recognises that tag.

Various aspects and embodiments of the present invention will now be illustrated in more detail by way of example. It will be appreciated that modification of detail may be made with out departing from the scope of the invention, and the skilled man will appreciate that further antibodies and antigen binding fragments for use in the invention may be obtained as described herein in Example 2, and their properties with respect to binding to the different isoforms of FcγRIII and even to different allelic forms of FcγRIIIA, may be tested as described herein in the Examples.

For the avoidance of doubt, the terms "FcγRIII", "FcγRIIIA" and "FcγRIIIB" are used herein interchangeably with the terms "CD16", "CD16A" (denoting the A isoform of CD16) and "CD16B" (denoting the B isoform of CD16), respectively.

BRIEF DESCRIPTION OF THE FIGURES

FIG. 6: Amino acid sequence alignment of allelic variants of the CD16A and CD16B isoforms. The signal peptides is shown as shaded. Asterisks and italic text mark the differences within the allelic variants of CD16B. Variations between the CD16A and CD16B isoforms are shown in bold and underlined. The position of the CD16A 158 Val/Phe polymorphism is indicated by the box.

FIG. 8: Target-specific killing by TandAb-activated NK cells. $1\times10^4$ of the indicated calcein-labelled L540CY (results shown in panel [A]) or JOK-1 target cells (results shown in panel [B]) were incubated for 3 hours with $1\times10^5$ NK cells in the presence of the indicated concentrations of CD30×CD16 TandAb (filled rhombus) or CD19×CD16 TandAb (open rhombus). As a control, target cells were incubated with NK cells without antibody (filled square). Percent specific lysis was calculated from the measured fluorescence counts of the released calcein and analysed by non-linear regression using the GraphPadPrism software.

EXAMPLES

Example 1

Figure 1:
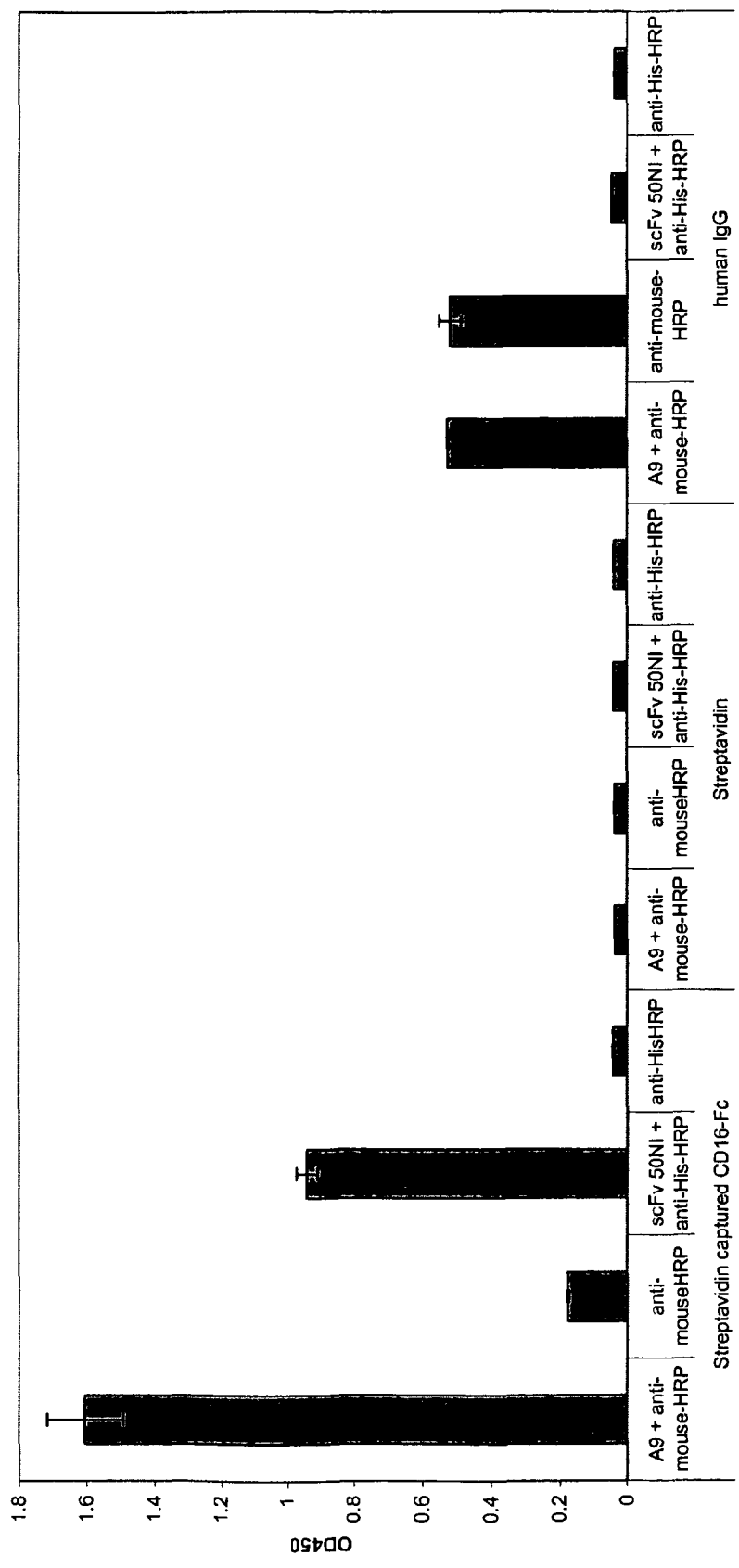
FIG. 1: ELISA Results Demonstrating Binding of scFv 50NI to Streptavidin Captured CD16-Fc ELISA plates were coated with 500 ng Streptavidin and 300 ng human IgG (Sigma-Aldrich, Taufkirchen, Germany) per well in 100 mM NaHCO$_3$, pH 8.6. Subsequently, 300 ng biotinylated CD16A-Fc was absorbed for 30 min at room temperature in PBS. Streptavidin captured CD16A-Fc, Streptavidin and human IgG were incubated with 1 µg/mL murine MAb A9 or 50 µl crude periplasmic extract from clone 50NI in PBS/TWEEN 0.1%/2% skimmed milk powder. Binding of MAb A9 was detected with a goat anti-mouse antibody-HRP conjugate. Binding of scFv 50NI was detected using anti-Penta His antibody-HRP-conjugate. The absorbance at 450 nm of the HRP-substrate tetramethyl benzidine (TMB) was measured following termination of the reaction with 50 µl 0.5M sulphuric acid.

Transient Expression and Purification of a Human CD16A-Fc Fusion Protein

A secreted, soluble form of the CD16A-Fc fusion protein was produced in HEK-293 cells after transient transfection with plasmid pCDM-CD16-Fc encoding human CD16A fused to the Fc portion of human IgG1 (Mandelboim et al., 1999, supra).

HEK-293 cells (ATCC accession number CRL-1573) were cultured in complete DMEM medium (DMEM medium supplemented with 10% heat-inactivated fetal calf serum (FCS), 2 mM L-glutamine, 100 U/mL penicillin G sodium and 100 µg/mL streptomycin sulfate; all from Invitrogen, Karlsruhe, Germany) at 37° C. in a humidified atmosphere with 5% $CO_2$. Calcium phosphate mediated transfection of these cells was effected as follows.

One day prior to transfection $1.5\times10^6$ HEK-293 cells were used to seed 10 mL complete DMEM medium in a 10 cm diameter cell culture plate. 10 µg plasmid DNA was mixed with 500 µL 250 mM $CaCl_2$, which was then added drop-wise to 500 µL 2×HEBS buffer (280 mM NaCl, 1.5 mM $Na_2HPO_4$, 50 mM HEPES, pH7.05) and incubated for 15 min at room temperature. 9 mL complete DMEM medium was added to this transfection cocktail, mixed and transferred to one dish of HEK-293 cells from which the culture medium had been removed. The next day, the transfection medium was exchanged for serum-free DMEM medium (DMEM medium supplemented with 2 mM L-glutamine, 100 U/mL penicillin G sodium and 100 µg/mL streptomycin sulfate and 1× Insulin-Transferrin-Selenium-A supplement (all from Invitrogen). Supernatants containing the secreted CD16A-Fc fusion protein were collected twice in a period of two to six days after transfection, depending on the viability of the cells. After each harvest, fresh serum-free medium was added to the cells. Harvested supernatants were centrifuged to remove cells or cell debris and stored at −80° C. until used for purification of the fusion protein. Transfections were repeated until approximately 1.2 L of supernatant containing CD16A-Fc fusion proteins were harvested.

Purification of the recombinant CD16A-Fc fusion protein was performed on a 2 mL Protein A column (Protein A Sepharose™ Fast Flow, Amersham Pharmacia). The column was equilibrated with ten volumes DMEM pH 7 (Invitrogen; supplemented with 100 µg/mL Streptomycin, 100 u/ml Penicillin, 1× Insulin-Transferrin-Selenium-A and 2 mM L-Glutamine). Before loading the cell culture supernatant (1200 ml) on the column, it was passed through a 0.2 µm sterile filter and adjusted to pH 7 by adding 0.1 M glycine/HCl pH 2.7. The column was run by gravity flow at 4° C. Subsequently, the column was washed with 10 volumes DMEM pH 7. Elution was carried out with 6 volumes 0.1 M glycine/HCl pH 2.7. 1 ml fractions were collected directly into 55 µl 1 M Tris/HCl pH 8.8.

Analysis of fraction numbers 1-10 in a 12% PAA-gel showed the vast majority of the fusion protein in fractions 2-7. These fractions were pooled and dialysed twice against 5 L PBS pH 7.0. The determination of protein concentration according to Bradford (Bradford, 1976, Anal. Biochem. 72:248-254) revealed a total yield of 21 mg CD16A Fc-fusion protein i.e. 17.5 mg of fusion protein was produced per liter of culture supernatant.

Example 2

Identification and Isolation of a CD16-A Specific Antibody

The CD16A-Fc fusion protein was used to screen a large human IgM-derived scFv phage display library, which had been produced using methods similar to those described previously (Dörsam et al., 1997 FEBS Letts 414:7-13, Little et al., 1999 J. Immunol. Methods 231:3-9, Schwarz et al., FASEB J. 18:1704-6). The clones in this library contained nucleotide sequences between the scFv coding sequence and the pIII gene of phage M13, which encoded a hexa-histidine tag, an amber stop codon and a c-myc epitope.

500 µg CD16A Fc-fusion protein was biotinylated using the ECL protein biotinylation module (Amersham Pharmacia Biotech, Uppsala Sweden) and used in three rounds of selection against the phage display library. Prior to selection the library was consecutively pre-adsorbed to polystyrene coated streptavidin and to human IgG (Sigma-Aldrich, Taufkirchen, Germany) in order to remove potential binders to these proteins. Approximately $10^{12}$ phages from the library were resuspended in PBS, 0.1% tween, 2% skimmed milk were incubated with soluble biotinylated CD16A Fc-fusion. Phage antigen complexes were captured by streptavidin coated magnetic beads using a magnetic separator (Dynal, Oslo, Norway). Phage that did not specifically bind to the target antigen were removed by ten washing steps with PBS, 0.1% tween. Bound entities were eluted by using glycine-HCl pH 2.2, and after neutralization with 2 M Tris/HCl, pH 8.0, the eluate was used for infection of freshly grown E. coli XL1 Blue cells at mid log phase ($OD_{600}$ 0.2-0.5). Cells that had been successfully transformed with phagemids encoding the human scFvs were selected for ampicillin resistance and were subsequently infected with M13K07 helper phage to generate phage progeny displaying scFv for the following in vitro selection. After the $3^{rd}$ round of selection, individual colonies were grown in LB medium containing 100 µg/mL ampicillin and 20 µg/mL tetracycline at 30° C. in a PP-Masterblock 2 mL (Greiner, Frickenhausen, Germany). Cells were harvested by centrifugation and resuspended in 200 µL 200 mM Tris-HCl, pH 7.5, 20% Sucrose, 1 mM EDTA. During a 1 hour incubation on ice the outer membrane was destroyed and soluble periplasmic proteins including the scFv were released into the culture medium. After elimination of spheroplasts and cellular debris by centrifugation, the crude periplasmic extracts were tested in ELISA for scFv binding to the CD16A-Fc fusion protein. One clone (50NI) was found on three separate occasions.

Since the affinity selection of this clone from the phage display library was performed on a human Fc-fusion protein, it was necessary to demonstrate specificity of the clone 50NI for the CD16 portion of the molecule.

A periplasmic extract from clone 50NI was prepared as described above and was tested in ELISA for its ability to bind to the CD16A-Fc fusion protein and to human IgG. Anti-CD16 murine monoclonal antibody A9 (Hombach et al. 1993 Int. J. Cancer 55:830-836) was used as a control. A Maxisorb™ ELISA plate was pre-coated with 500 ng Streptavidin and 300 ng human IgG (Sigma-Aldrich, Taufkirchen, Germany) per well in 100 mM $NaHCO_3$, pH 8.6. Subsequently 300 ng biotinylated CD16A-Fc was captured for 30 min at room temperature in PBS.

Streptavidin captured CD16A-Fc, streptavidin and human IgG were incubated with 1 µg/mL MAb A9 or 50 µl crude periplasmic extract from clone 50NI in PBS/TWEEN 0.1%/2% skimmed milk powder. Binding of MAb A9 was detected with a goat anti-mouse-HRP conjugate (0.5 µg/mL, Dianova, Hamburg, Germany), whereas binding of scFv 50NI was detected by an anti-Penta His HRP-conjugate (1 µg/mL, Qiagen, Hilden, Germany). 50 µL of TMB (KPL, Maryland, USA) was used as HRP-substrate and the colour allowed to develop. The reaction was stopped with 50 µL 0.5 M $H_2SO_4$, and absorbance was measured at 450 nm.

The results are illustrated in FIG. 1. MAb A9 and the scFv 50NI clearly recognize the biotinylated streptavidin captured CD16A-Fc fusion protein. The scFv 50NI reveals neither a signal on the human IgG nor on streptavidin alone. The anti-Penta His HRP-conjugate used as a secondary reagent revealed no non-specific binding to the antigens. However, the goat anti-mouse-HRP conjugate used as a secondary reagent for MAb A9 detection caused some background staining due to cross reactivity with the human Fc portion of the CD16 fusion protein and the human IgG used as a negative control.

These results are strongly indicative that the scFv 50NI exhibits specificity for the CD16A portion of the fusion protein and not the Fc portion.

Example 3

Testing scFv 50NI in FACS on Different Cells Lines Stably Expressing the CD16 Isoforms, Human PBMC and Granulocytes To determine whether the 50NI scFv reveals binding to the native CD16A protein on the cell surface, a crude periplasmic extract of the scFv was tested by flow cytometry on two different cell lines expressing CD16A or CD16B, respectively. For this purpose, the cell line BW/CD16A expressing CD16A (Mandelboim et al., 2001, Nature 409:1055-1060);) and the cell line 293-CD16 (HEK-293 cells stably transfected with a plasmid coding for the NA-2 allele of the human CD16B isoform) were used.

To assess whether the 50NI scFv has the ability to bind to CD16A expressed on the surface of natural killer (NK) cells and/or to CD16B present on the surface of neutrophilic granulocytes (van de Winkel and Capel, 1993, supra; van Spriel et al., 2000, Immunol. Today 21(8):391-397), it was tested for binding to freshly isolated peripheral blood mononuclear cells (PBMC) consisting of 10-20% NK cells and on polymorphonuclear cells (PMN) representing more than 95% CD16B-positive neutrophilic granulocytes, using flow cytometry.

Murine MAb A9 and a periplasmic extract from the murine clone $scFv_{18}$ A9 (a scFv derived from MAb A9) were used as controls.

3.1 Growth of Cell Lines and Isolation of PBMC and PMN.

BW/CD16A cells were cultured in DMEM medium supplemented with 10% heat-inactivated foetal calf serum (FCS), 2 mM L-glutamine, 100 U/mL penicillinG sodium, 100 µg/mL streptomycin sulphate, 1% non essential amino acids and 5 mg/mL G418. The 293/CD16B cells were cultured in DMEM medium supplemented with 10% heat-inactivated fetal calf serum (FCS), 2 mM L-glutamine, 100 U/mL penicillinG sodium, 100 µg/mL streptomycin sulfate, and 0.5 mg/mL G418. The non-transfected parental cells lines BW and 293 were cultured as described above for the stable transfectants, but in medium lacking G418.

PBMC and PMN were isolated from heparinized peripheral blood from a healthy donor by density gradient centrifugation. The blood was twice diluted with PBS, layered on a double cushion consisting of 12 mL Histopaque-1119™ (Sigma-Aldrich) and an upper cushion of 12 mL Histopaque-1077. Centrifugation was carried out at 800 g for 25 min. PBMC located on the upper Histopaque-1077™ (Sigma-Aldrich) cushion and the PMN located on the Histopaque-1119™ cushion were collected and washed 3 times with PBS before use.

3.2 Isolation of Periplasmic Extracts Containing scFv 50NI and $scFv_{18}$ A9

Crude periplasmic extracts containing scFvs were isolated from 5 mL bacterial cultures. The freshly inoculated bacteria were grown overnight at 37° C. in LB medium containing 50 mM glucose, 100 µg/mL ampicillin and 20 µg/mL tetracycline. The overnight cultures were diluted to $OD_{600nm}$=0.1 in LB medium with ampicillin and tetracycline and further grown at 37° C. till $OD_{600nm}$=0.8. The bacteria were harvested by centrifugation and resuspended in LB medium containing 0.1 mM isopropyl-β-D-thiogalactopyranoside (IPTG), 100 µg/mL ampicillin and 20 µg/mL tetracycline. After overnight incubation of induced bacteria at 21° C., 300 µL periplasmic extracts were isolated as described for ELISA. Before use in FACS analysis, the periplasmic extracts were dialyzed against PBS overnight.

3.3 Flow Cytometry

For flow cytometric analysis, $1 \times 10^6$ cells BW, BW/CD16A, HEK-293, 293/CD16B, PBMC and PMN were stained with either the monoclonal antibody A9 or a periplasmic extract containing $scFv_{18}$A9 and 50NI.

$1 \times 10^6$ cells were incubated with 100 µL of the dialyzed periplasmic extracts or with MAb A9 (10 µg/mL) for 45 min on ice. Antibody/scFv, incubations with PBMC and PMN were supplemented with polyclonal human IgG at 1 mg/mL to block Fc receptors on the surface of subpopulations of PBMC and PMN. After washing with FACS buffer (PBS supplemented with 2% heat-inactivated FCS and 0.1% sodium azide) the cells were incubated on ice for 45 minutes with 0.1 mL of 0.01 mg/mL anti-$(His)_6$ mouse MAb 13/45/31-2 (Dianova, Hamburg, Germany) in the same buffer. After a second washing cycle, the cells were incubated with 0.1 mL of 0.015 mg/mL FITC-conjugated goat anti-mouse IgG antibodies (Dianova, Hamburg, Germany) under the same conditions. The cells were then washed again and resuspended in 0.5 mL of FACS buffer containing 2 µg/mL propidium iodide (Sigma-Aldrich) to exclude dead cells. The fluorescence of $1 \times 10^4$ stained cells was measured using a Beckman-Coulter Epics XL flow cytometer. Mean fluorescence intensities were calculated using System-II and Expo32 software (Beckman-Coulter, Krefeld, Germany). Fluorescence caused by background staining of the cells with the secondary agents alone was subtracted from the results and histograms plotted (not shown) to aid analysis.

3.4 Results

The murine monoclonal anti-CD16 antibody A9 and the A9-derived anti-CD16 $scFv_{18}$ served as positive controls and revealed clear binding to BW/CD16A in comparison to the non-transfected parental cells (BW). The scFv 50NI also showed unambiguous staining of the BW/CD16A cells at a level comparable to A9.

Both monoclonal antibody A9 and scFv$_{18}$ A9 exhibited strong binding to 293/CD16B transfectants, which express the CD16B isoform on their surface, whilst 50 NI did not bind to this cell line.

The monoclonal antibody A9 and the scFv$_{18}$ A9 revealed a clear staining of a small subpopulation of the PBMC representing the NK cell fraction. The scFv 50NI similarly exhibited binding to this subpopulation.

In contrast to A9 and the scFv derived from A9, both of which showed a strong signal on the purified granulocytes, the 50 NI scFv failed to bind to PMN.

This data indicates that the 50NI scFv binds specifically to the CD16A isoform and does not bind to the CD16B isoform. The scFv 50NI also recognizes not only recombinant CD16A but also the native antigen as expressed on the surface of NK cells.

Example 4

Binding of Human Anti-CD16A scFv 50NI to Enriched NK Cells

To demonstrate that the PBMC subpopulation that was recognized by 50NI as shown in example 3 comprises natural killer (NK) cells, an enriched population of NK cells was isolated from PBMC and analysed for binding to scFv 50NI by flow cytometry.

PBMCs were isolated from heparinized peripheral blood from a healthy donor by density gradient centrifugation. The blood sample was twice diluted with PBS, layered on a cushion of Histopaque-1077™ (Sigma-Aldrich) and centrifuged at 800 g for 25 min. PBMC located in the interface were collected and washed 3 times with PBS. For isolation of NK cells, the PBMC were resuspended in 2% FCS/PBS and were subjected to one round of negative selection using the Easy-SEP™ negative NK cell enrichment kit (CellSystems) according to the manufacturers instructions. Staining of the PBMC and NK cells and flow cytometric analysis was performed essentially as described in example 3 above: 1×10$^6$ of the cells were stained with 10 µg/mL of the MAb A9 or the anti-CD56 monoclonal antibody MAb B159 (BD Biosciences/Pharmingen) followed by 15 µL FITC-conjugated goat anti-mouse IgG. The murine scFv$_{18}$ A9 and the human scFv 50NI were used for staining at a concentration of 50 µg/mL, and cell bound scFv were detected with 10 µg/mL MAb anti-(His)$_6$ followed by 15 µL FITC-conjugated goat anti-mouse IgG. All stainings were performed in the presence of 1 mg/mL polyclonal human IgG. Dead cells were excluded by propidium iodide staining as described above. Data analysis was carried out as described in Example 3 above.

4.1 Results

Staining of PBMC with the anti-CD56 and anti-CD16 antibodies clearly identified a subpopulation representing the NK cell fraction. The scFv 50NI also recognized a similar small cell population indicating binding to NK cells.

After negative enrichment of the NK cells, all four antibodies/scFvs revealed unambiguous staining. Whilst the anti CD56 MAb exhibited binding to the entire NK cell population, a small fraction of the cells were not stained using the antibodies directed against CD16. This might reflect the presence of some cells with a CD16-negative phenotype.

Example 5

Ca$^{2+}$ Flux Measurement after scFv 50NI Binding

CD16A, the low affinity receptor for IgG, is expressed on the majority of human peripheral blood NK cells in association with the immunoreceptor tyrosine-based activation motif (ITAM) containing the γ chain from FcεRI or the ζ chain from the TCR/CD3 complex. Binding of CD16A to antibodies or immune complexes triggers NK cell cytotoxicity and cytokine secretion. The activation involves phosphorylation of the γ chain or ζ chain, respectively, and subsequent intracellular signal transduction such as Ca$^{2+}$ mobilization.

To test whether the human anti-CD16 scFv 50NI possesses NK-activating properties, Ca$^{2+}$ flux measurements with freshly isolated NK cells were performed after ligation of surface receptors with anti-CD16 monoclonal antibodies or scFv. Since some anti-CD16 antibodies need cross-linking by secondary reagents to elicit a clear increase of intracellular calcium, anti-c-myc and anti-(His)$_6$ in combination with anti-mouse IgG were used to cross-link cell-bound anti-CD16 antibodies.

For NK preparation, PBMC were isolated from heparinized peripheral blood from a healthy donor by density gradient centrifugation. The blood sample was twice diluted with PBS, layered on a cushion of Histopaque-1077™ and centrifuged at 800 g for 25 min. PBMC located in the interface were collected and washed 3 times with PBS. For isolation of NK cells the PBMC were resuspended in 2% FCS/PBS and subjected to one round of negative selection using the Easy-SEP™ negative NK cell enrichment kit according to the instructions of the manufacturer (Cell Systems). The NK cells were washed once with HBSS and then labelled with the calcium-indicator Fluo-4-acetoxymethyl (AM) ester (Molecular Probes, Leiden, The Netherlands) at a concentration of 2 µM for 30 min at room temperature in the dark. After washing with HBSS the cells were incubated for further 20 min in HBSS to allow complete de-esterification of intracellular AM esters and washed again with HBSS. For flow cytometric analysis of intracellular calcium changes aliquots of labelled NK cells were first measured without any antibody on a Beckman-Coulter Epics XL flow cytometer to determine background fluorescence. After approximately 60 sec, anti-CD16 antibodies (2 µg MAb A9 or 5 µg scFv18 A9 or 5 µg 50NI scFv) were added and the measurement was continued. At 180 sec after starting, 20 µg polyclonal goat anti-mouse IgG antibodies (GAM) were added to the MAb A9 sample to cross-link A9 bound to CD16 on the surface of NK cells. To cross-link the scFvs 2.5 µg anti-(His)$_6$ mouse MAb 13/45/31-2 and 2.5 µg anti-c-myc MAb 9E10 were applied before continuing measurement. In the case of the samples with the scFvs 20 µg polyclonal goat anti-mouse IgG antibodies were added at later time points to further cross-link anti-(His)$_6$ and/or anti-c-myc MAbs bound to the scFv. The mean fluorescent intensities from short time intervals were determined using the Expo32 software (Beckman-Coulter, Krefeld, Germany) and plotted against time (not shown).

The fluorometry tracings obtained with freshly isolated NK cells clearly showed that MAb A9 elicits a strong increase in the intracellular calcium concentration upon cross-linking with anti-mouse IgG antibodies, which is reflected by higher fluorescence signals. In contrast to MAb A9, the scFv derived from A9 (scFv$_{18}$ A9) induced little or no increase of intracellular calcium even after cross-linking with anti-(His)$_6$, anti-c-myc and anti-mouse IgG antibodies. The human scFv 50NI, however, elicited a clear (although slightly weak) fluorescence signal after ligation of the cell surface bound scFv with cross-linking antibodies. This demonstrates that the human scFv 50NI possesses binding characteristics that are suitable for triggering NK cell activity via CD16A.

Example 6

Affinity Maturation of the 50NI scFv by Light Chain Shuffling

To obtain anti-CD16 scFvs with increased affinity, a chain shuffled library based on the clone 50NI was generated by rearrangement of the 50NI V$_H$ chain with a V$_L$ gene repertoire.

The $V_\kappa$ and $V_\lambda$ gene repertoires were excised from pEX-HAM1 DNA originating from a large human naïve scFv library previously described (Schwarz et al. supra, 2004). This repertoire reflects approximately $10^5$ individual $V_\kappa$ and $V_\lambda$ chains each. Rearrangement with the 50NI heavy chain by cloning into the MluI and NotI sites of pEXHAM1 and transformation of 1 μg into E. coli XL1 blue (1.8 kV, 0.1 cm gap cuvette 25 μF, 200Ω) resulted in a $2.6 \times 10^6$ ($V_\kappa$) and $2.2 \times 10^6$ ($V_\lambda$ member library.

Sequence analysis of 32 randomly picked clones after transformation showed that each clone contained an individual light chain and 24 clones revealed expression of full length scFvs detectable by an anti-His antibody (Qiagen, Hilden, Germany) in a Western Blot.

Four rounds of selection were performed on a biotinylated CD16A-Fc fusion protein as described in example 2. Selection pressure favouring high affinity binders was created by successively limiting the antigen concentration ($1^{st}$ round 20 nM, $2^{nd}$ round 1 nM, $3^{round}$ round 0.1 nM, $4^{th}$ round 0.01 nM. The κ- and λ rearranged libraries were kept separately.

Approximately $10^8$ phage from each library resuspended in PBS/0.1% TWEEN/2% skimmed milk were incubated with biotinylated CD16A-Fc fusion. Phage antigen complexes were rescued by adding streptavidin coated magnetic beads and non-specific antigen binding phage were removed by ten washing steps with PBS/0.1% TWEEN. In a first step, bound entities were eluted by using glycine-HCl pH 2.2. After neutralisation with 2 M Tris/HCl pH 8, freshly grown E. coli XL1 Blue (mid log phase $OD_{600}$ 0.2-0.5) were added in order to recover phage which could not be removed by low pH. Cells eluted by acidic elution were also mixed with logarithmic growing XL1 blue host cells.

Cells successfully transduced with phagemid, encoding a human scFv were selected for ampicillin resistance and subsequently infected with M13K07 helper phage to generate phage presenting scFv for the following in vitro selection. In subsequent rounds of selection, phage recovered by acidic elution and infection of XL1 blue were handled separately. After the $3^{rd}$ and $4^{th}$ round of affinity selection, individual colonies were tested in ELISA as described in example 2.

None of the clones tested from the rearranged K-library showed significant signals above that of the parental clone 50NI grown as reference in the same master block. However, several clones were sequenced and proved to be identical to the parental clone, indicating that no suitable κ-chain was found which improved the binding properties.

In contrast, analysis of clones derived from the rearranged λ-library revealed numerous clones generating signals up to five fold over the reference. 30 clones were selected for sequencing after the $3^{rd}$ and 34 clones were selected for sequencing after the $4^{th}$ round of bio panning. Sequencing was performed with the Long Read Tower (Visible Genetics, Toronto Canada) using the Deaza Kit (Visible Genetics, Toronto Canada) following the manufacturers guidelines. Acidic elution of bound phage particles or direct infection of the host cells had no obvious effect on the later distribution of the clones. Five different groups of enriched clones and several individuals were identified. Table 2 gives an overview of the different groups.

TABLE 2

Designations of clones representing a certain group in subsequent examples are highlighted in bold

| Group | Total Frequency | $3^{rd}$ round 30 clones sequenced | $4^{th}$ round 34 clones sequenced |
| --- | --- | --- | --- |
| A | 19/64 | 3-LB1, 3-LB24, 3-LB36, 3-LB48, 3-LS1, 3-LS4, 3-LS19 | 4-LB28, 4-LB34, 4-LB27, 4-LB43, 4-LS6, 4-LS10, 4-LS22, 4-LS26, 4-LS68; 4-LS80, 4-LS88 |
| B | 9/64 | 3-LB3, 3-LB41, 3-LS23, 3-LS35, 3-LS87 | 4-LB46, 4-LS38, 4-LS12, 4-LS39 |
| C | 13/64 | 3-LB5, 3-LB10, 3-LB32, 3-LS17, 3-LS22, 3-LS79, 3-LS36, 3-LS89 | 4-LB4, 4-LB13, 4-LB41 4-LS25, 4-LB25 |
| D | 5/64 | 3-LS72 | 4-LS73, 4-LB32, 4-LB33, 4-LB33 |
| E | 5/64 |  | 4-LS14, 4-LS37, 4-LS87, 4-LS72, 4-LS44 |
| individuals |  | 3-LB6, 3-LB23, 3-LS49; 3-LS34, 3-LS60, 3-LS28, 3-LS30, 3-LS55, 3-LS40 | 4-LS5, 4-LB14, 4-LS21, 4-LS46 |

Clones forming group A represent the parental clone 50NI which was also present in the shuffled library due to re-ligated or uncut parental vector or due to rearrangement during library construction. This finding correlates with the fact that clones from this group yielded the weakest ELISA signals.

All other groups contain newly arranged light chains revealing increased ELISA signals compared to the parental clone. Clones from group C and D were found in comparable numbers after the $3^{rd}$ and $4^{th}$ selection round.

Analysis of the sequences using a V-base alignment software (http://vbase.mrc-cpe.cam.ac.uk) revealed that all new $V_\lambda$ chains belong to the VL3 family as well as the VL chain from the parental clone.

Amino acid sequences of the common $V_H$ chain shared by all clones is given herein as SEQ ED NO 9 and the specific $V_L$ chain for clones 50NI, 3-LB3, 3-LB5, 3-LB6, 3-LS49, 4-LS14 and 4-LS21 are given herein as SEQ ID NOs 10-16 respectively. The nucleic acid sequence encoding the common VH chain is given herein as SEQ ID NO 1, and the nucleic acid sequences encoding the individual VL chains for clones 50NI, 3-LB3, 3-LB5, 3-LB6, 3-LS49, 4-LS14 and 4-LS21 are given herein as SEQ ID NOs 2-8 respectively. The amino acid sequences of the individual heavy and light chain CDRs are given in Table 1, with the common heavy chain CDRs shown as the first entry in the table, followed by light chain CDRs for 50NI, 3-LB3, 3-LB5, 3-LB6, 3-LS49, 4-LS14 and 4-LS21 (shown as entries 2-8, respectively).

Example 7

FACS Analysis of Affinity Matured scFv on Cell Lines Transfected with CD16A and CD16B A preliminary FACS analysis with crude periplasmic extracts from all individual clones showed that all chain shuffled scFv retained their ability to bind CD16A. For this test, HEK-293 cells transiently transfected with CD16A were used (data not shown). Based on this test, the clones 3-LB3, 3-LB5, 3-LB6, 3-LS49, 4-LS14 and 4-LS21 were selected for further characterisation.

Nucleic acids encoding these scFvs were subcloned into the expression vector pSKK2, where they were cloned in-frame with a N-terminal PelB leader sequence, and C-terminal hexa-histidine and c-myc tags. The nucleotide sequences of these sub-clones are as follows:

```
pSKK2-50NI (SEQ ID NO 36)
atgaaatacctattgcctacggcagccgctggcttgctgctgctggcagctcagccggccatggcggaggtccagctggtaca gtctggagcagaggtgaaaaagcccggggagtctctgaaggtttcctgcaaggcatctggatacaccttcaccagctactatat gcactgggtgcgacaggcccctggacaagggcttgagtggatgggaataatcaaccctagtggtggtagcacaagctacgca cagaagttccagggcagagtcaccatgacccgggacacgtccacgagcacagtctacatggagcttagcagcctgagatctg aggacacggccgtgtattactgtgctagaggtagtgcttattactacgattttgctgactactggggccagggaaccctggtcacc gtctcctcagggagtgcatccgccccaacccttaagcttgaagaaggtgaattttcagaagcacgcgtatcctatgagctgatgc agccaccctcagtgtccgtgtcctcaggacagacagccagcatccctgctctggagataaattggaggaaaaatatgtttcctg gtatcaacagaggccaggccagtcccctgtgttggtcatttatcaggataataagcggccctcagggatccctgagcgattctct ggctccaactctgggaacacagccactctgaccatcagcgggacccaggcgatggatgaggctgactactattgtcaggtgtg ggacaattacagtgtgctattcggcggagggaccaagctgaccgtcctaggtcagcccaaggctgcccctcggtcactctgtt cccgccgtccgcggccgctggatccgaacaaaagctgatctcagaagaagacctaaactcacatcaccatcaccatcactaa pSKK2-3-LB3 (SEQ ID NO 37)
atgaaatacctattgcctacggcagccgctggcttgctgctgctggcagctcagccggccatggcggaggtccagctggtaca gtctggagcagaggtgaaaaagcccggggagtctctgaaggtttcctgcaaggcatctggatacaccttcaccagctactatat gcactgggtgcgacaggcccctggacaagggcttgagtggatgggaataatcaaccctagtggtggtagcacaagctacgca cagaagttccagggcagagtcaccatgacccgggacacgtccacgagcacagtctacatggagcttagcagcctgagatctg aggacacggccgtgtattactgtgctagaggtagtgcttattactacgattttgctgactactggggccagggaaccctggtcacc gtctcctcagggagtgcatccgccccaacccttaagcttgaagaaggtgaattttcagaagcacgcgtatcctatgagctgacac agccactctcagagtcagtggcccaggacagacgccaggattacctgtggggaaacaacattgaaagtagaaatgttcac tggtaccagcagaagccaggccaggcccctgtgttggtcatctatagggataacaaccggccctctgggatccctgagcgattc tctggctccaattcggggaacatggccacccttgaccatcagcagagcccaagccggggatgcagctgactattactgtcaggt gtgggacaactacactgtgctattcggcggagggaccaagctgaccgtcctaggtcagcccaaggctgcccctcggtcactc tgttcccgccgtccgcggccgctggatccgaacaaaagctgatctcagaagaagacctaaactcacatcaccatcaccatcact aa pSKK2-3-LB5 (SEQ ID NO 38)
atgaaatacctattgcctacggcagccgctggcttgctgctgctggcagctcagccggccatggcggaggtccagctggtaca gtctggagcagaggtgaaaaagcccggggagtctctgaaggtttcctgcaaggcatctggatacaccttcaccagctactatat gcactgggtgcgacaggcccctggacaagggcttgagtggatgggaataatcaaccctagtggtggtagcacaagctacgca cagaagttccagggcagagtcaccatgacccgggacacgtccacgagcacagtctacatggagcttagcagcctgagatctg aggacacggccgtgtattactgtgctagaggtagtgcttattactacgattttgctgactactggggccagggaaccctggtcacc gtctcctcagggagtgcatccgccccaacccttaagcttgaagaaggtgaattttcagaagcacgcgtatcctatgagctgacac agccaccctcagtggcagtggcccaggaaagacggccaggattacctgtggggaaacaacattggaagtaaaaatgtgca ctggtaccagcagaagccaggccaggcccctgtgctggtcatctatagggatagcaaccggccctctgggatccctgagcgat tctctggctccaactcggggaacacggccacccttgaccatcagcagagcccaagccggggatgaggctgactttattgtcag gtgtgggacaactatattgtgctgttcggcggagggaccaagctgaccgtcctgggtcagcccaaggctgcccctcggtcact ctgttcccgccgtccgcggccgctggatccgaacaaaagctgatctcagaagaagacctaaactcacatcaccatcaccatcac taa
```

-continued pSKX2-3-LB6 (SEQ ID NO 39)
atgaaatacctattgcctacggcagccgctggcttgctgctgctggcagctcagccggccatggcggaggtccagctggtaca
gtctggagcagaggtgaaaaagcccggggagtctctgaaggtttcctgcaaggcatctggatacaccttcaccagctactatat
gcactgggtgcgacaggcccctggacaagggcttgagtggatgggaataatcaaccctagtggtggtagcacaagctacgca
cagaagttccagggcagagtcaccatgacccgggacacgtccacgagcacagtctacatggagcttagcagcctgagatctg
aggacacggccgtgtattactgtgctagaggtagtgcttattactacgattttgctgactactggggccagggaaccctggtcacc
gtctcctcagggagtgcatccgccccaacccttaagcttgaagaaggtgaattttcagaagcacgcgtacaggctgtgctgactc
agccgccctcagtgtcagtggccccaggacagacggccaggattccctgtgagggaaacaacattggaagtaaaaatgtcca
ctggtatcggcagaagccaggccaggtccctgtcctggtcatgtatgatgatagcgaccggccctcagggatccctgagcgatt
ctctggctccaactctgggaacacagccactctgaccatcagcgggacccaggcgatggatgaggctgactactattgtcaggt
gtgggacaattacagtgtgctattcggcggagggaccaagctgaccgtcctaggtcagcccaaggctgcccctcggtcactct
gttcccgccgtccgcggccgctggatccgaacaaaagctgatctcagaagaagacctaaactcacatcaccatcaccatcacta
a pSKK2-3-LS49 (SEQ ID NO 40)
atgaaatacctattgcctacggcagccgctggcttgctgctgctggcagctcagccggccatggcggaggtccagctggtaca
gtctggagcagaggtgaaaaagcccggggagtctctgaaggtttcctgcaaggcatctggatacaccttcaccagctactatat
gcactgggtgcgacaggcccctggacaagggcttgagtggatgggaataatcaaccctagtggtggtagcacaagctacgca
cagaagttccagggcagagtcaccatgacccgggacacgtccacgagcacagtctacatggagcttagcagcctgagatctg
aggacacggccgtgtattactgtgctagaggtagtgcttattactacgattttgctgactactggggccagggaaccctggtcacc
gtctcctcagggagtgcatccgccccaacccttaagcttgaagaaggtgaattttcagaagcacgcgtacagcctgtgctgactc
agccactctcagtgtcagtggccccgggacagacggccaggattacctgtgggggaaacaacattggaagtaaaaatgtgca
ctggtaccagcagaagccaggccaggcccctgtactggtcatctatagggacagcagccggccctctgggatccctgagcga
ctctctggctccaactcggggggacacggccaccctgaccatcagcagagcccaggccggggatgaggctgactattactgtca
ggtgtgggacgactacattgtggtcttcggcggagggaccaagctgaccgtcctaggtcagcccaaggctgccccccggtc
actctgttcccgccgtccgcggccgctggatccgaacaaaagctgatctcagaagaagacctaaactcacatcaccatcaccat
cactaa pSKK2-4-LS14 (SEQ ID NO 41)
atgaaatacctattgcctacggcagccgctggcttgctgctgctggcagctcagccggccatggcggaggtccagctggtaca
gtctggagcagaggtgaaaaagcccggggagtctctgaaggtttcctgcaaggcatctggatacaccttcaccagctactatat
gcactgggtgcgacaggcccctggacaagggcttgagtggatgggaataatcaaccctagtggtggtagcacaagctacgca
cagaagttccagggcagagtcaccatgacccgggacacgtccacgagcacagtctacatggagcttagcagcctgagatctg
aggacacggccgtgtattactgtgctagaggtagtgcttattactacgattttgctgactactggggccagggaaccctggtcacc
gtctcctcagggagtgcatccgccccaacccttaagcttgaagaaggtgaattttcagaagcacgcgtatcctatgagctgacac
agccaccctcggtgtcagtgacccaggacagacggccacgattacctgcggggcaaacgacattggaaaagaaatgtcca
ctggtaccaacagaggccaggccagtccctgtgttggtcatttatcaggataataagcggccctcagggatccctgagcgattc
tctggctccaactctgggaacacagccactctgaccatcagcgggacccaggcgatggatgaggctgactactattgtcaggtg
tgggacaattacagtgtgctattcggcggagggaccaagctgaccgtcctaggtcagcccaaggctgcccctcggtcactctg
ttcccgccgtccgcggccgctggatccgaacaaaagctgatctcagaagaagacctaaactcacatcaccatcaccatcactaa pSKK2-4-LS21 (SEQ ID NO 42)
atgaaatacctattgcctacggcagccgctggcttgctgctgctggcagctcagccggccatggcggaggtccagctggtaca
gtctggagcagaggtgaaaaagcccggggagtctctgaaggtttcctgcaaggcatctggatacaccttcaccagctactatat
gcactgggtgcgacaggcccctggacaagggcttgagtggatgggaataatcaaccctagtggtggtagcacaagctacgca -continued

```
cagaagttccagggcagagtcaccatgacccgggacacgtccacgagcacagtctacatggagcttagcagcctgagatctg aggacacggccgtgtattactgtgctagaggtagtgcttattactacgattttgctgactactggggccagggaaccctggtcacc gtctcctcagggagtgcatccgccccaaccct taagcttgaagaaggtgaattttcagaagcacgcgtacagcctgtgctgactc agccatcctcggtgtcagtggcccca ggacagacggccacgatctcctgtgggggacacaacattgggagtaaaaatgtgca ctggtaccagcagaggccaggccagtccctgtgttggtcatttatcaggataataagcggccctcagggatccctgagcgatt ctctggctccaactctgggaacacagccactctgaccatcagcgggacccaggcgatggatgaggctgactactattgtcaggt gtgggacaattacagtgtgctattcggcggagggaccaagctgaccgtcctaggtcagcccaaggctgcccctcggtcactct gttccc gccgtccgcggccgctggatccgaacaaaagctgatctcagaagaagacctaaactcacatcaccatcaccatcacta a
```

The nucleotide sequence encoding the PelB leader sequence is atgaaataccta ttgcctacggcagc-cgctggcttgctgctgctggcagctcagccggccatggcg (SEQ ID NO 43).

The nucleotide sequence encoding the linker region between the light and heavy chain variable domains of each scFv is gaagaaggtgaattttcagaagca (SEQ ID NO 44).

The nucleotide sequence of the c-myc and hexa-histidine tags are gaacaaaagctgatctcagaagaagaccta (SEQ ID NO 45) and catcaccatcaccatcac (SEQ ID NO 46), respectively.

The vectors comprising the sub-clones were transformed into *E. coli* RV308, expressed in 2 liter shake flask cultures and purified by immobilized metal ion affinity chromatography (IMAC) according to Le Gall et al. (2004, J. Immunol. Methods 285:111-127).

To assess whether the chain shuffled scFv retained their specificity for CD16A as indicated for 50NI in Example 3, transfected cell lines expressing either CD16A or CD16B were tested with IMAC purified scFv. For flow cytometric analysis, the following cell lines were used: BW and BW/CD16A transfectants were cultured as described previously. 293 cells and 293-CD16B transfectants were handled as described previously. 293-CD16A and 293-NKp46 were generated by transient transfection of 293 cells with plasmids encoding the extracellular domains of CD16A or NKp46, respectively, fused to the transmembrane and cytoplasmic domain of the human CD3ζ chain (pcDNA3-CD16A-zeta and pcDNA3-NKp46-zeta, obtained from Dr. O. Mandelboim, University of Jerusalem, Israel). The transient transfections were performed using the calcium phosphate method as described in Example 1 and were used for flow cytometric staining and analysis two days after transient transfection. Flow cytometric staining and analysis was performed as essentially described before. $1 \times 10^6$ of the indicated cells were stained with 50 µg/mL of the purified scFv followed by 10 µg/mL MAb 13/45/31-2 (anti-hexa His) and 15 µg/mL FITC-conjugated goat anti-mouse IgG.

Figure 2:
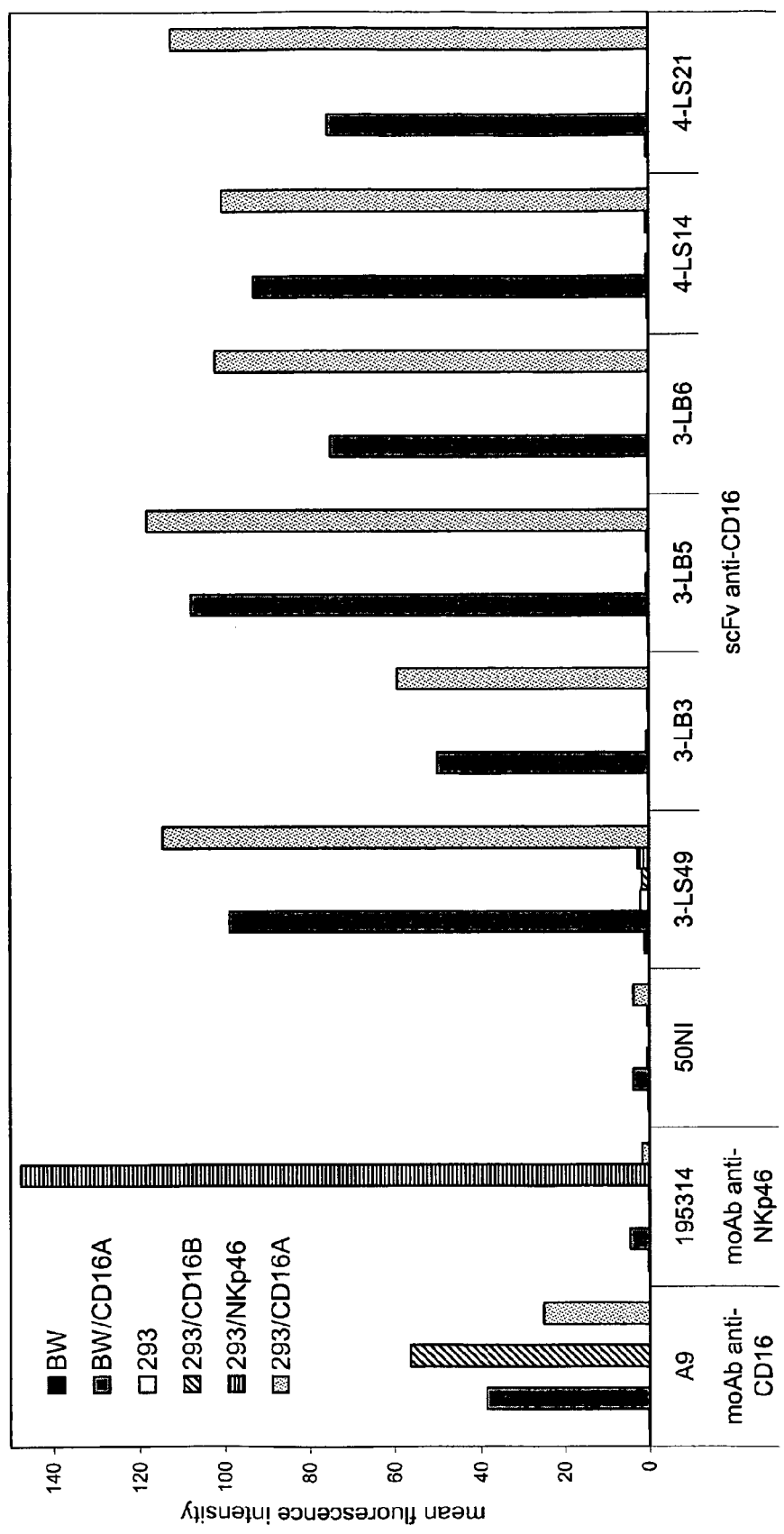
FIG. 2: Affinity-matured human anti-CD16 scFv bind to cell transfectants expressing CD16A but not cells expressing CD16B. Murine BW cells and BW cells stably transfected with CD16A (BW/CD16A), HEK-293 cells and HEK-293 cells transfected with CD16B (293/CD16B), CD16A (293/CD16A) or NKp46 (293/NKp46) were stained with 10 µg/mL of the MAb A9 (anti-CD16) or MAb 195314 (anti-NKp46) followed by 15 µg/mL FITC-conjugated goat anti-mouse IgG. The anti-CD16 scFv were used at a concentration of 50 µg/mL and were detected with 10 µg/mL MAb 13/45/31-2 (anti-Hexa His) followed by FITC-conjugated goat anti-mouse IgG. The mean fluorescence intensities obtained from flow cytometric analysis were corrected by subtracting the fluorescence values from cell stainings with the secondary reagents alone, and plotted in the diagram.

To demonstrate that the transfected cells express the corresponding antigens on their cell surface, cells were stained in parallel with 10 µg/mL of MAb A9 and anti-NKp46 monoclonal, MAb 195314 (R&D Systems, Wiesbaden, Germany). MAbs A9 and 195314 were detected with 15 µg/mL FITC-conjugated goat anti-mouse IgG. The mean fluorescence intensities obtained from the flow cytometric analysis were corrected by subtracting the fluorescence values from stainings with the secondary reagents alone, and the results shown in FIG. 2.

MAb A9 used as a positive control stains bound as expected to all cell lines transfected with CD16, irrespective of the isoform. No binding to the NKp46-transfectants was observed, whereas staining with MAb 195314 directed against NKp46 clearly showed that the cells were successfully transfected with the control plasmid encoding NKp46.

The parental human anti-CD16 scFv 50NI used as a reference revealed weak staining of the two cell lines expressing CD16A on their surface (the BW/CD16 A and 293/CD16A cells). In contrast, the newly isolated scFv with rearranged light chains exhibited highly improved binding to these cells. None of the new variants bound 293 cells stably transfected with CD16B, demonstrating specificity for the A isoform of CD16.

Example 8

Figure 5:
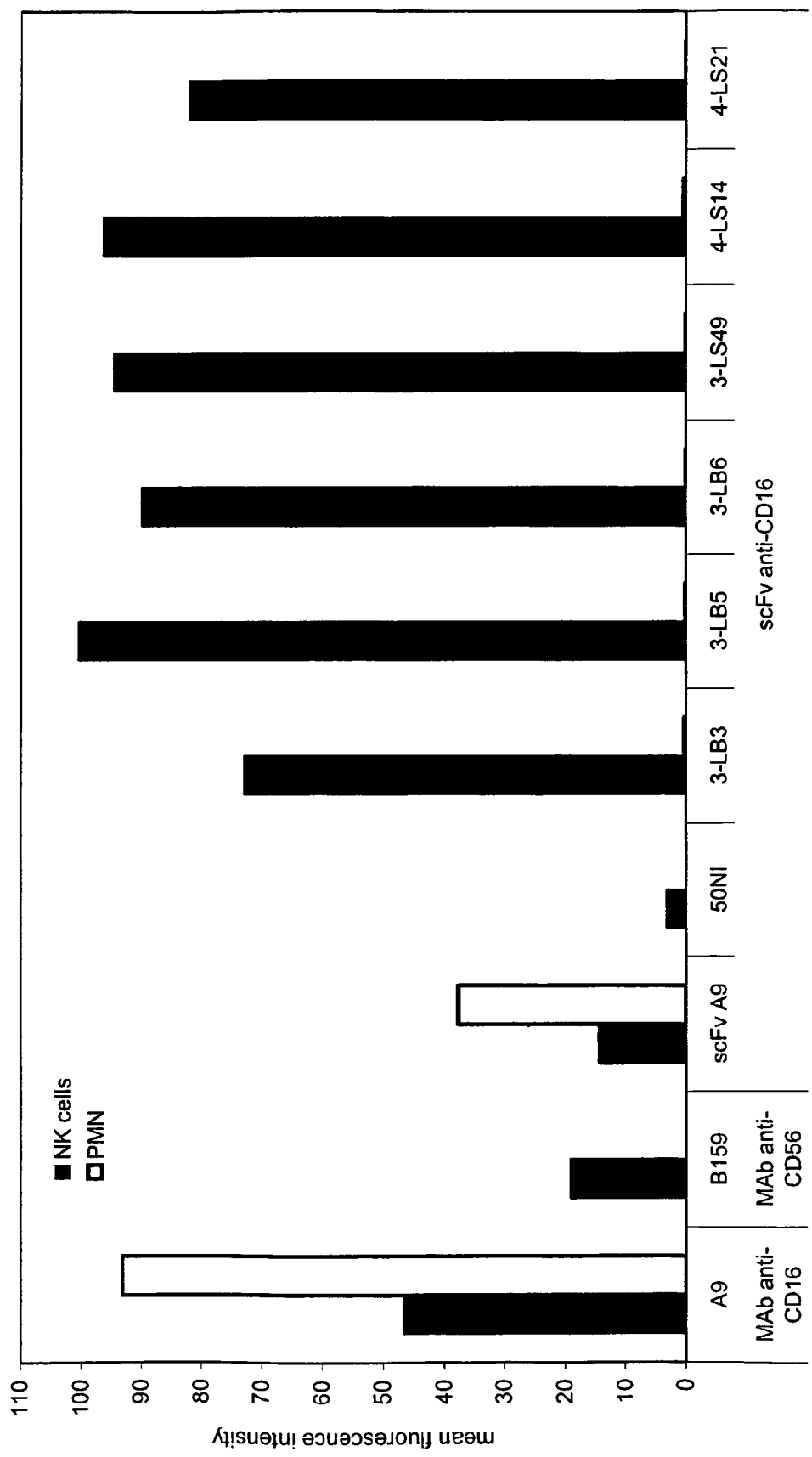
FIG. 5: Flow cytometric analysis of affinity-matured anti-CD16 scFv on PMN and NK cells. Polymorphonuclear cells (PMN) and natural killer (NK) cells were isolated from peripheral blood from a healthy donor and used for flow cytometric staining and analysis. The cells were stained with 10 µg/mL of the anti-CD16 MAb A9 and anti-CD56 MAb B159 followed by 15 µg/mL FITC-conjugated goat anti-mouse IgG. All scFv were used at a concentration of 50 µg/mL and were detected with 10 µg/mL anti-(His)$_6$ followed by 15 µg/mL FITC-conjugated goat anti-mouse IgG. The mean fluorescence intensities obtained from flow cytometric analysis were corrected by subtracting the fluorescence values from cell stainings with the secondary reagents alone and were plotted in the diagram.

Testing Affinity Matured scFv Fragments on Freshly Isolated PMN and Enriched NK-Cells To assess whether the improved scFv retained their ability to specifically bind to CD16A expressed on leukocytes, freshly isolated PMN and enriched NK cells from donor blood were stained as described previously using IMAC-purified scFv. Enrichment of NK cells was performed by negative selection as described above. Mean fluorescence intensities obtained from flow cytometric analysis are shown in FIG. 5.

Staining of the enriched leukocyte population with anti-CD16 MAb A9 and anti-CD56 MAb B159 clearly demonstrates that the population consists of $CD16^+/CD56^+$ peripheral blood NK cells. The MAb A9 and the murine scFv derived from A9 stained the CD16A-positive NK cell fraction and showed an even stronger signal on CD16B-positive granulocytes.

MAb A9 recognized a subpopulation (18.5%) of PBMCs corresponding to CD16-positive NK cells. Strong binding was observed on enriched NK cells and isolated granulocytes (data not shown).

The parental clone 50NI revealed weak but clear binding to enriched NK-cells, whilst no staining of the granulocytes was visible. The affinity matured variants 3-LB3, 3-LB5, 3-LB6, 3-LS49, 4-LS14 and 4-LS21 revealed staining patterns resembling that of 50NI, but with improved binding signals. This data provides further support for the fact that the affinity matured scFvs are able to distinguish specifically between the two isoforms of CD16 and bind specifically to CD16A.

Example 9

ELISA on Recombinant CD16A-Fc and CD16B

In order to generate further supporting data concerning the CD16A specificity of the scFvs, an ELISA was performed using the CD16A-Fc fusion protein (Example 1) and commercially available recombinant CD16B-Fc (Allele NA-2; BSA free; RD Systems). A gp34-Fc fusion protein was used as a negative control. The recombinant proteins were coated overnight at a concentration of 80 nM in 100 mM $NaHCO_3$ at pH 8.8.

Detection of scFv bound to the recombinant proteins was carried out by using an anti-c-myc-HRP conjugate (10 µg/ml). The positive control comprised MAb A9 (1 µg/mL) followed by a goat anti-mouse IgG HRP-conjugate (0.5 µg/mL). Binding to the recombinant CD16B was tested by directly staining with anti-His-HRP (1 µg/mL) and binding to the Fc-Fusion proteins was tested by an anti-human IgG-HRP conjugate (0.15 µg/mL).

Figure 3:
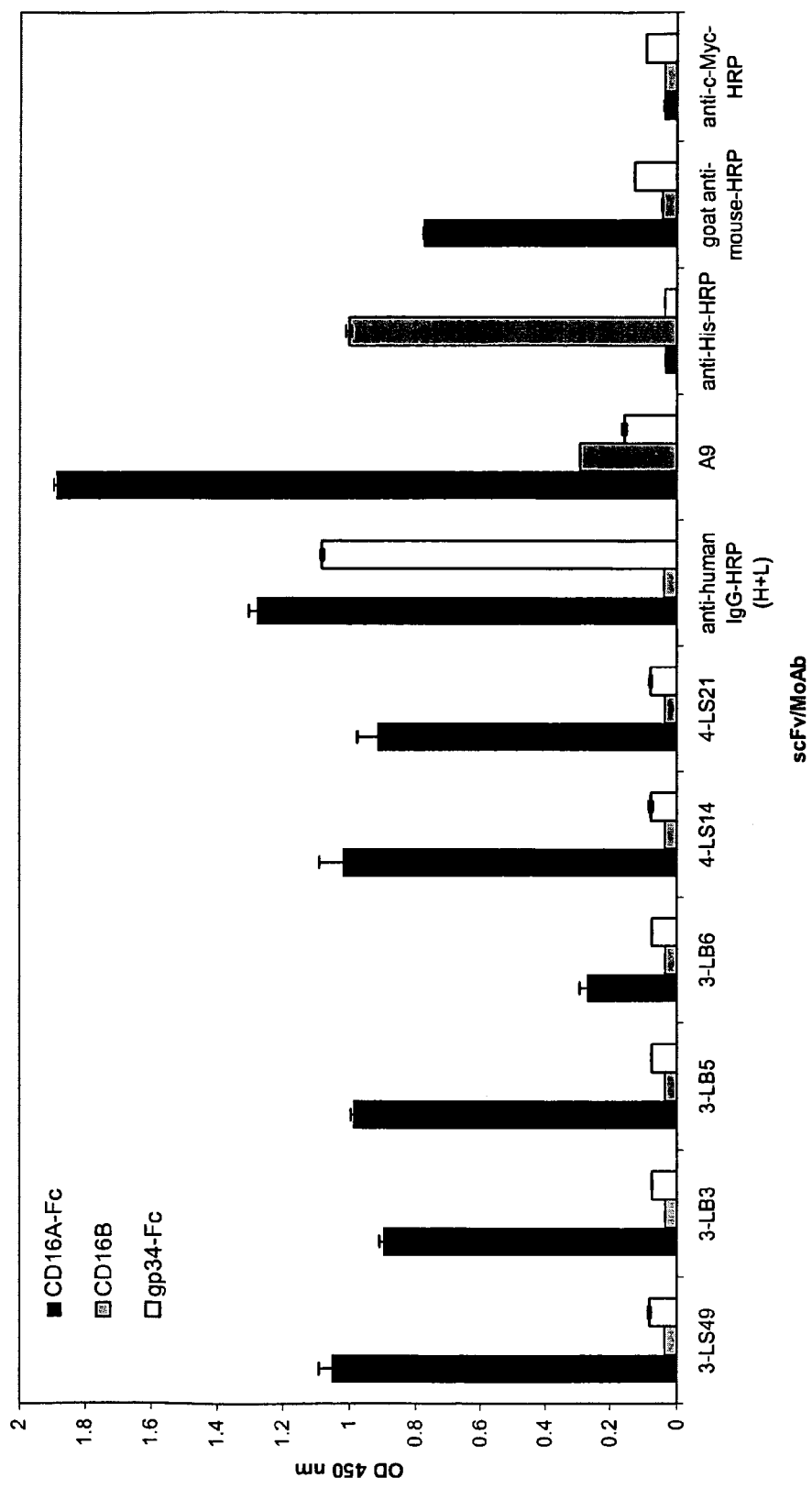
FIG. 3: ELISA on recombinant CD16A-Fc and CD16B. Recombinant CD16A-Fc and CD16B proteins were coated at 80 nM in 0.1 M NaHCO$_3$, pH 8.8. Wells were blocked with PBS, 2% skimmed milk. The binding of the scFv to the recombinant proteins and to gp34-Fc (negative control) was detected using an anti-c-Myc-HRP conjugate (10 µg/ml). Incubation with anti-CD16 MAb A9 (1 µg/mL) was followed by a goat anti-mouse IgG HRP-conjugate (0.5 µg/mL). Coated recombinant CD16B was directly detected by staining with an anti-His-HRP (1 µg/mL) and coating of the Fc-Fusion proteins was tested by an anti-human IgG-HRP conjugate (0.5 µg/mL). As HRP-substrate, 50 µL of TMB were used. After termination of the reaction with 50 µL 0.5 M H$_2$SO$_4$, absorbance was measured at 450 nm.

All of the scFv showed strong binding to CD16A-Fc, whereas no binding to CD16B was observed (FIG. 3). A slightly increased background binding was noticed with gp34-Fc. This was probably due to a small amount of unspecific binding to gp34-Fc, since all secondary antibodies tested alone also revealed slightly increased background signals on this protein.

As expected, A9 strongly recognized CD16A-Fc. However, it must be considered that the secondary goat anti-mouse-HRP conjugated antibody shows significant cross reactivity with the human Fc fusion (see control with goat anti mouse-HRP alone). Reproduction of this assay using a preadsorbed goat anti-mouse IgG-HRP conjugate with minimal cross reactivity to human IgG (data not shown) revealed no significant reduction in background binding.

MAb A9 showed a clear signal on CD16B, which was not influenced by the secondary reagent.

Example 10

Western Blot on Recombinant CD16A-Fc Under Reducing and Non Reducing Conditions

For further characterization all of the anti-CD16A scFv were tested for binding in Western Blot on recombinant CD16A-Fc and NKp46-Fc.

CD16A-Fc and NKp46-Fc serving as a negative control were separated by 12% SDS-gel under reducing condition and on a 8% gel under non reducing conditions. The proteins were transferred on a nitrocellulose membrane by electroblotting. After staining with Ponceau S, the membrane was cut into strips of 5 mm width. Each nitrocellulose strip was individually incubated with scFv (4 µg/ml) in PBS, 0.1% tween, 2% skimmed milk. Detection was carried out with the anti-Penta His HRP-conjugate (1 µg/mL) using diaminobenzidine (DAB) as a peroxidase substrate. Control strips were incubated with A9 (1 µg/mL) or anti-NKp46 195314 followed by a goat anti-mouse IgG HRP-conjugate (0.2 µg/mL, minimal cross reactivity). As an additional positive control, a goat anti-human IgG HRP-conjugate (0.16 µg/mL) was used for detection of the Fc portion of the fusion proteins.

The monoclonal antibodies A9 and 195314 recognized their antigen under reducing as well as under non reducing conditions. The goat anti-mouse-HRP conjugate used as a secondary reagent for MAb A9 revealed slight cross reactivity with the Fc portion of the CD16A-Fc fusion protein. In contrast, binding of the anti-CD16 scFvs was only observed under non-reducing conditions indicating that a secondary structure stabilized by disulfide bridges is required for recognition. The parental clone 50NI shows weaker signals compared to the affinity matured scFvs. No binding of the scFv 3-LB6 could be detected and none of the scFv revealed cross reactivity with the NKp46-Fc control protein, confirming specificity for CD16.

Example 11

Analysis of the scFv by Size Exclusion Chromatography on a Superdex 200 Column

To determine whether the higher affinities of the scFv variants are primarily due to improved monovalent binding, the protein preparations were analysed for their oligomeric composition on a Superdex 200 gel filtration column. The LMW Gel Filtration Calibration Kit (Amersham Pharmacia Biosciences, Freiburg, Germany) served as a standard. Table 3 gives an summary of the molecular forms present in the individual protein preparations.

TABLE 3

Molecular forms of scFvs present in individual protein preparations. 3-LB5 was not analysed due to low protein concentration.

| scFv | Monomer | Dimer |
| --- | --- | --- |
| 3-LS49 | 67.2% | 32.8% |
| 3-LB3 | 87.8% | 12.2% |
| 3-LB6 | 100% | — |
| 4-LS14 | 57.6% | 42.4% |
| 4-LS21 | 100% | — |

Size exclusion chromatography clearly demonstrated that the scFv 3-LB6 and 4-LS21 were solely monomeric.

In contrast 3-LS49, 3-LB3 and 4-LS14 revealed significant proportions of dimeric molecules, indicating that the improved binding properties of these molecules may not be only due to higher affinity, as for 3-LB6 and 4-LS21, but may also reflect an avidity effect due to dimer formation.

Example 12

Determination of scFv Affinity by Surface Plasmon Resonance (SPR)

The affinity constants ($K_D$ values) of the scFv were determined by SPR using the BIAcore 2000 biosensor system (Amersham-Pharmacia). The CD16A-Fc fusion protein and BSA used as a negative control were immobilized on the carboxymethyldextran-coated sensor chip CM5 using conventional NHS/EDC chemistry for the amine coupling procedure (BIAcore). Purified scFvs were diluted in HBS-EP buffer (BIAcore, Uppsala, Sweden). Binding data was generated by passing varying concentrations of the scFv antibodies (100 nM, 200 nM, 400 nM, 800 nM and 1600 nM) over the immobilized antigen. The anti-CD16 MAb A9 served as positive control. All SPR measurements were performed at a constant flow rate of 20 µL/min in HBS-EP buffer at 25° C. Each injected sample (100 µl) was in contact with antigen for 5 minutes. The dissociation was followed for 30 minutes. After each cycle, the surface of the sensor chip was flushed with HBS-EP buffer. Signals from the control channel coated with BSA were automatically subtracted. Kinetic constants were calculated according to the 1/1 Langmuir binding model using the BIAevaluation version 3.0 software (BIAcore). The calculated off- and on-rate constants and respective $K_D$ values are summarized in table 3. For MAb A9, used as a control, a $K_D$ of $1.75 \times 10^{-9}$ M was calculated correlating with the value of $1.55 \times 10^{-9}$ M described in the literature (Renner et al., 2001 Cancer Immunol. Immunother. 50:102-108). Additionally, equilibrium dissociation constants were deduced from steady state analysis for the scFv 50NI, 4-LS21 and 3-LB6 of the SPR data.

TABLE 4

Data for the kinetics of binding for individual scFvs

| scFv | $k_{on}$ (M$^{-1}$s$^{-1}$) | $k_{off}$ (s$^{-1}$) | $K_D = k_{off}/k_{on}$ (M) | $K_{eq}$ (M) |
|---|---|---|---|---|
| 50NI | $(1.76 \pm 1.37) \times 10^4$ | $(2.17 \pm 0.55) \times 10^{-2}$ | $1.23 \times 10^{-6}$ | $2.56 \times 10^{-6}$ |
| 4-LS21 | $(5.60 \pm 1.88) \times 10^4$ | $(6.30 \pm 0.48) \times 10^{-3}$ | $1.13 \times 10^{-7}$ | $2.03 \times 10^{-7}$ |
| 3-LB6 | $(5.48 \pm 0.48) \times 10^4$ | $(6.52 \pm 0.44) \times 10^{-3}$ | $1.19 \times 10^{-7}$ | $1.06 \times 10^{-7}$ |
| 3-LS49 | $(2.93 \pm 1.05) \times 10^4$ | $(4.01 \pm 0.93) \times 10^{-3}$ | $1.37 \times 10^{-7}$ | n.d. |
| 3-LB3 | $(2.16 \pm 0.44) \times 10^4$ | $(2.97 \pm 0.48) \times 10^{-3}$ | $1.38 \times 10^{-7}$ | n.d. |
| 4-LS14 | $(5.09 \pm 0.99) \times 10^4$ | $(5.57 \pm 1.31) \times 10^{-3}$ | $1.09 \times 10^{-7}$ | n.d. |
| 3-LB5 | $(7.33 \pm 0.44) \times 10^4$ | $(2.97 \pm 0.48) \times 10^{-3}$ | $4.05 \times 10^{-8}$ | n.d. |
| MA5 A9 | $(1.01 \pm 0.46) \times 10^5$ | $(1.77 \pm 0.84) \times 10^{-4}$ | $1.75 \times 10^{-9}$ | n.d. |

Kinetic constants calculated independently by these two methods correlate well and direct comparison with the parental clone 50NI revealed more than twenty-fold improvement of affinity by light chain shuffling. All three scFv form solely monomeric protein populations (compare Table 3, Example 11) indicating that the improved binding properties are due to higher affinity based on optimisation of the antigen scFv interface and not to avidity effects.

The scFv 3-LS49, 3-LB-3 and 3-LS14 reveal comparable $K_D$ values but show an inhomogeneous molecule population comprising significant percentages of dimeric molecules (compare table 2, example 13). Thus, improved affinities of these antibodies may be at least partially due to multivalent binding.

Example 13

Induction of Ca$^{2+}$ Flux in NK Cells by Binding of Affinity Matured Anti-CD16 scFv To assess whether the affinity-matured scFv retained their ability to elicit Ca$^{2+}$ mobilization in peripheral blood NK cells as shown for the parental anti-CD16 scFv 50NI, NK cells were isolated and enriched from peripheral blood and used for Ca$^{2+}$ flux measurements by flow cytometry as described above in Example 5.

The results clearly demonstrate that the addition of MAb anti-(His)$_6$ followed by polyclonal goat anti-mouse IgG antibodies (GAM) alone did not induce significant changes of the intracellular calcium concentration in freshly isolated NK cells. However, a clear increase of the fluorescence signal was observed when scFv 50NI was added and cross-linked by MAb anti-(His)$_6$ followed by GAM as already shown in Example 5.

When the affinity-matured anti-CD16 scFv (3-LS49 or 4-LS21, used as illustrative examples) were applied, the increase in induced signal after cross-linking by anti-(His)$_6$ followed by GAM was at least as strong as the signal triggered by 50NI. Thus, it may be concluded that all scFv that are derived from the human scFv 50NI by chain-shuffling retain their ability to activate NK cells and to trigger an intracellular calcium mobilization by binding to CD16A.

Example 14

Triggering of Cytolytic Activity in Freshly Isolated NK Cells

CD16A is involved in antibody-dependent cellular cytotoxicity (ADCC) mediated by NK cells. In vitro it was shown that activating monoclonal antibodies of the IgG isotype specific for CD16 can trigger killing of FcR-positive target cell lines. To determine whether the affinity-matured anti-CD16A scFv that induce calcium mobilization in NK cells are also able to mediate NK cytotoxicity, these scFv were tested in a redirected killing assay with freshly isolated NK cells against murine FcR-positive P815 cells. Since the scFv lack the Fc portion of IgG, they were used together with an anti-(His)$_6$ murine monoclonal antibody. The redirected cell lysis was measured in a calcein-release assay.

NK cells were isolated and enriched from PBMC of a healthy donor as described above. Flow cytometric analysis demonstrated that the NK population consists of 81% CD16-positive and 94% CD56-positive cells; CD3-positive or CD19-positive cells could not be detected in significant amounts (data not shown). The murine P815 cell line (kindly provided by Dr. G. Moldenhauer, DKFZ, Heidelberg, Germany) was cultured in RPMI 1640 medium supplemented with 10% heat-inactivated fetal calf serum (FCS), 2 mM L-glutamine, 100 U/mL penicillinG sodium, 100 µg/mL streptomycin sulfate, and 50 µM β-mercaptoethanol. For the assay, the P815 target cells were labelled with 10 µM CalceinAM (Molecular Probes) in RPMI 1640 medium without FCS for 30 min at 37° C. After washing twice with RPMI 1640 medium the labelled P815 cells were resuspended in RPMI 1640 medium supplemented with 10% heat-inactivated FCS, 2 mM L-glutamine, 100 U/mL penicillinG sodium, 100 µg/mL streptomycin sulfate, to a density of 1×10$^6$/mL. From this suspension, 50 µL corresponding to 1×10$^4$ cells were seeded in individual wells of a 96 well round bottom microtiter plate. 1×10$^5$ freshly isolated NK cells were added in 50 µL to the wells giving an effector-to-target ratio of 10:1. Anti-CD16 antibodies and control antibodies were added to the wells to a final concentration of 1 µg/mL and where indicated 1 µg/mL anti-(His)$_6$ mouse MAb 13/45/31-2 was applied. Monoclonal antibodies OKT3 (an anti-CD3 MAb), A9 and 13/45/31-2 anti-(His)$_6$ were a kind gift from Dr. G. Moldenhauer, DKFZ, Heidelberg, Germany. Antibody B159 anti-CD56 was purchased from BD Biosciences/Pharmingen (Heidelberg, Germany) and 195314 anti-NKp46 from R&D Systems (Wiesbaden, Germany). The plates were incubated for 3 hours at 37° C. in a humidified atmosphere with 5% CO$_2$. To some wells, 1% Triton X 100 was added (Roth, Karlsruhe, Germany) to give maximum lysis of target cells. Spontaneous release of calcein was determined by incubating the target cells without effector cells and without antibodies. After incubation, the microtiter plates were centrifuged at 500 g for 5 min and 100 µL of the supernatant was harvested to measure fluorescence (F) of released calcein with a multilabel reader at 520 nm (Victor3, Perkin Elmer, Rodgau, Germany). The percentage of lysis was calculated according to the formula: [F$_{(sample)}$−F$_{(spontaneous)}$]/

Figure 4:
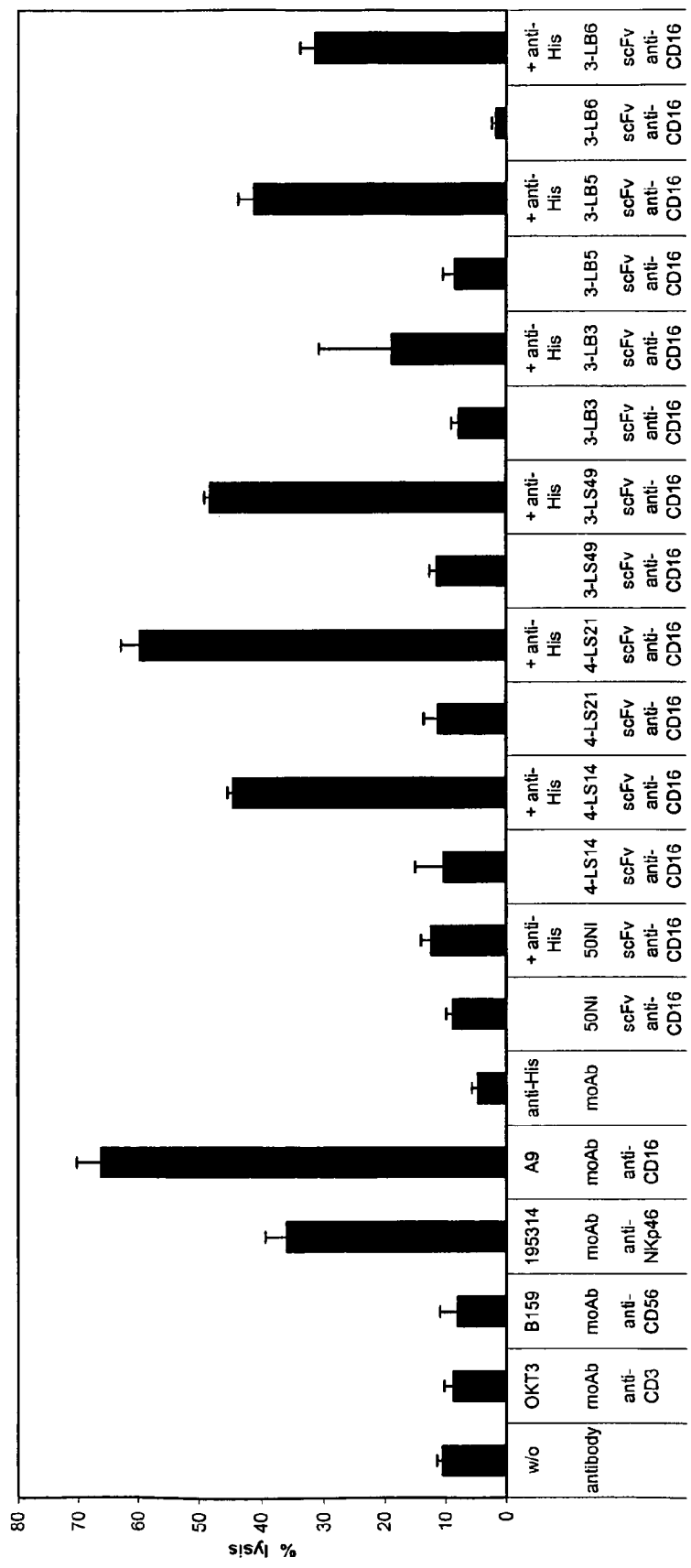
FIG. 4: Triggering of redirected cytotoxicity in freshly isolated NK cells by human, affinity-matured anti-CD16 scFv. NK cells were isolated and enriched from the peripheral blood of a healthy donor and used as effector cells in a cytotoxicity assay with calcein-labelled P815 as target cells. Effector (E) and target (T) cells were incubated for 3 hours at an E:T-ratio of 10:1 in the presence of 1 µg/mL of the indicated antibodies. Percentage of specific lysis was calculated from the measured fluorescence counts of the released calcein in the supernatant. Mean values and standard deviations from triplicates were plotted.

$[F_{(maximum)}-F_{(spontaneous)}] \times 100\%$. Mean values and standard deviations were determined from triplicate samples and plotted in FIG. 4.

As predicted the OKT3 anti-CD3, B159 anti-CD56 and anti-$(His)_6$ MAbs that were used as control antibodies induced only background killing similar to that of samples without any antibody. This demonstrates that binding of an antibody to a non-activating receptor like CD56 is not sufficient to induce NK cell cytotoxicity. In addition, the control antibodies exclude cytotoxic effects of IgGs that are binding to Fc receptors on P815 target cells but not to effector molecules on NK cells. In contrast, MAb 195314 (anti-NKp46) and A9 (anti-CD16), both targeting activating NK receptors, triggered a strong lysis of P815 targets that was in the range of 35% and 65%, respectively. The lysis of the target cells in the presence of the anti-CD16 scFv was between 1.8% and 11.5% indicating that the scFv alone could not activate NK cells. However, the addition of MAb anti-$(His)_6$ that facilitates cross-linking and binding to FcR-positive P815 target cells triggered a strong lysis in all samples. In the case of the affinity-matured scFv 4-LS21, almost 60% of the target cells were lysed. In comparison, the parental anti-CD16 scFv 50NI in combination with MAb anti-$(His)_6$ induced only a slight enhancement of the redirected killing of P815 targets by NK cells.

The results from the redirected cytotoxicity assay with the affinity-matured anti-CD16 scFv clearly demonstrate that the anti-CD16A scFv not only elicit calcium mobilization in NK cells but also trigger NK cytotoxicity.

Example 15

Generation of the Nucleic Sequences Encoding for the Human CD16A-Fc$^{48R/158F}$ F Variant and for the Three Different Human CD16B-Fc Allelic Variants Human FcγRIII exists as two isoforms, FcγRIIIA (transmembrane protein) and FcγRIIIB (GPI-anchored), that share 96% sequence identity in their extracellular immunoglobulin-binding regions (van de Winkel and Capel, 1993, Immunol. Today 14(5):215-221). For these two isoforms different allelic variants are described (Koene et al., 1997 Blood 90:1109-1114; Koene et al., 1998 Blood 91:673-679). FIG. 6 shows an alignment of the amino acid sequences of the allelic variants of the A and B isoforms.

The soluble CD16A-Fc fusion protein produced in HEK-293 cells after transient transfection with the plasmid pCDM-CD16-Fc and described in Example 1, is the human CD16A-Fc$^{48R/158V}$ (Mandelboim et al., 1999, supra). In position 158 of this isoform a bi-allelic polymorphism (FcγRIII-A 158Val/Phe), occurs in humans, which influences the affinity of the Fcγ RIII-A receptor on natural killer cells for IgG. For FcγRIII-A 158 Val, a higher affinity for IgG is reported in comparison to the allelic 158 Phe form (Koene et al., 1997 supra).

To demonstrate binding of the scFv 4-LS21 to the Phe variant, site-directed mutagenesis of the pCDM-CD16A-Fc$^{48R/158V}$ was performed to create the pCDM-CD16A-Fc$^{48R/158F}$. 10 ng of the pCDM-CD16A-Fc$^{48R/158V}$ plasmid was incubated with 125 ng of the primers P41, 5' CTG-CAGGGGGCTTTTTGGGAGTAAAAATGTG 3' (SEQ ID NO 47) and P42, 5' CACATTTTTACTCCCAAAAAGC-CCCCTGCAG 3' (SEQ ID NO 48), 25 mM of each dNTP and 2.5 units of the PfuUltra HF DNA polymerase (Stratagene). The reaction was performed for 30 sec at 95° C., followed by 16 cycles with 30 sec at 95° C., 60 sec at 66° C. and 318 sec at 68° C. The product was digested by DpnI restriction enzyme for 3 hours and the reaction was stopped finally by incubation at 80° C. for 20 min. Chemocompetent TOP10/P3 cells (Invitrogen) were transformed with 2 µl of the reaction mixture and 150 µl spread on LB plates containing 10 µg/ml tetracycline and 25 µg/ml ampicillin. The nucleic sequence encoding for the pCDM-CD16A-Fc$^{48R/158F}$ was confirmed by sequencing. CD16A-Fc$^{48R/158F}$ was expressed and purified as described Example 1.

The FcγRIIIB receptor is expressed in humans as three different allelic variants designated NA1, NA2 and SH respectively (Koene et al., 1997 supra; Koene et al., 1998 supra). Three synthetic genes encoding the human extracellular domain of the CD16B allelic forms were synthesized by Geneart (Regensburg, Germany). The nucleic acid sequences were cloned as a HindIII/BamHI fragment into the pSEC plasmid containing the nucleic sequence of the Fc region of the receptor. CD16B-Fc$^{NA1}$, CD16B-Fc$^{NA2}$ and CD16B-Fc$^{SH}$ were expressed and purified as described Example 1.

Example 16

Western-Blot on Different Allelic Variants of Human CD16

To demonstrate specificity of the scFv 4-LS21 for the CD16A isoform, Western-Blot analysis was performed on the different allelic variants of CD16A and CD16B. 750 ng of each of CD16A-Fc$^{48R/158V}$, CD16A-Fc$^{48R/158F}$, CD16B-Fc$^{SH}$, CD16B-Fc$^{NA1}$, CD16B-Fc$^{NA2}$ and NKp46-Fc (negative control) were loaded on an 8% SDS gel under non-reducing conditions and blotted onto a membrane.

The anti-CD16 scFv A9, the anti-CD16A scFv 4-LS21 and the anti-NKp46 scFv (negative control) were incubated at 4 µg/ml with the blot. Detection of scFv bound to the recombinant proteins was carried out using an anti-His-HRP conjugate (1 µg/mL). As controls HRP conjugated anti-human IgG and anti-His-HRP conjugate (1 µg/mL) were used.

The 4-LS21 scFv revealed strong binding to the allelic forms of CD16A only: no binding to the CD16B alleles was observed. This clearly demonstrated specificity of the human 4-LS21 scFv for the A isoform of CD16 and that 4-LS21 recognised both allelic variants of CD16A. In contrast the murine anti-CD16 scFv A9 showed uniform binding to all allelic variants of both CD16A and CD16B.

Example 17

ELISA on Different Allelic Variants of Human CD16

To further demonstrate specificity of the scFv 4-LS21 for the CD16A isoform, an ELISA was performed using the different allelic variants. Wells of a Maxisorp™ plate were coated with 100 mM NaHCO$_3$ containing 200 ng of CD16A-Fc$^{48R/158V}$, CD16A-Fc$^{48R/158F}$, CD16B-Fc$^{SH}$, CD16B-Fc$^{NA1}$, CD16B-Fc$^{NA2}$ or NKp46-Fc (negative control), respectively.

Figure 7B:
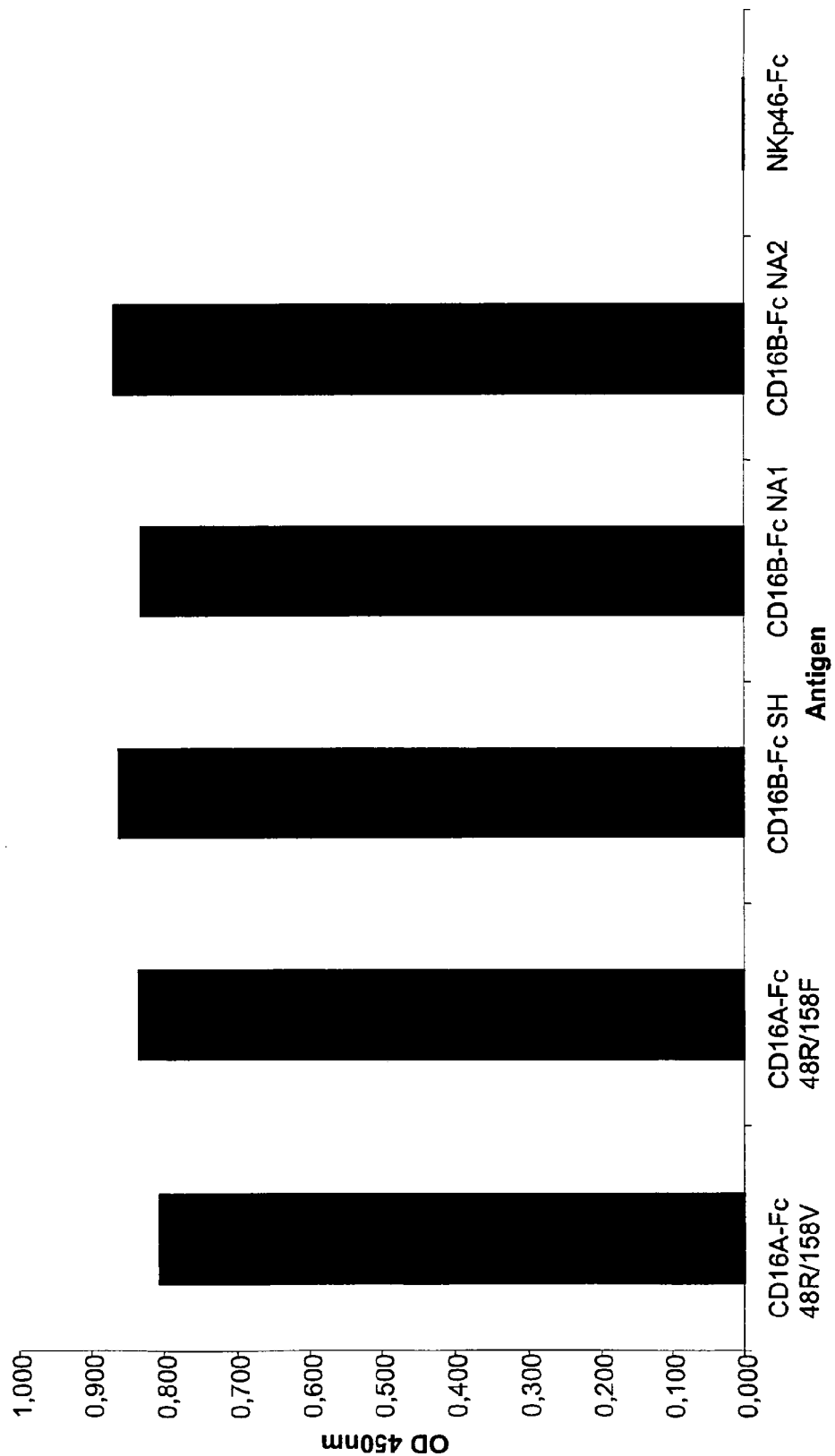
FIG. 7: ELISA on different CD16 isoforms. Wells of a Maxisorp™ plate were coated with 100 mM NaHCO$_3$ containing 200 ng of CD16A-Fc$^{48R/158V}$, CD16A-Fc$^{48R/158F}$, CD16B-Fc$^{SH}$, CD16B-Fc$^{NA1}$, CD16B-Fc$^{NA2}$ and NKp46-Fc. All antigens were incubated with [A] the scFv 4-LS21 followed by a HRP conjugated anti-His antibody or [B] with the MAb A9 followed by a goat anti-mouse HRP conjugate (minimal cross reactivity with human IgG). An anti-NKp46 scFv used as a primary antibody acted as a negative control.

The anti-CD16A 4-LS21 scFv and the anti-NKp46 scFv were incubated with the plate at a concentration of 4 µg/ml. Detection of scFv bound to the recombinant proteins was carried out using an anti-His-HRP conjugate (1 µg/ml). The scFv 4-LS21 showed strong binding to both allelic forms of CD16A, whereas no binding to the CD16B alleles was observed (FIG. 7A), thus demonstrating clear specificity of the 4-LS21 scFv for the CD16A isoform.

In a parallel assay (FIG. 7B) anti-CD16 MAb A9 (1 µg/ml) was assayed against an identically coated plate. The MAb A9 (1 µg/mL) incubation was followed by a goat anti-mouse IgG HRP-conjugate at 0.5 µg/ml (minimal cross reactivity to human Fc). MAb A9 bound strongly to all allelic variants (both CD16A and CD16B).

Example 18

Comparison of the Affinity of the scFv 4-LS21 and the Monoclonal Ab A9 to Different Allelic Forms of Human CD16 by Surface Plasmon Resonance (SPR)

The affinity constants ($K_D$ values) of scFv 4-LS21 and MAb A9 were determined by SPR for the allelic variants CD16A-Fc$^{48R/158V}$, CD16A-Fc$^{48R/158F}$, CD16B-Fc$^{SH}$, CD16B-Fc$^{NA1}$ and CD16B-Fc$^{NA2}$ using the BIAcore 2000 biosensor system (Amersham-Pharmacia) according to the protocol described in Example 12. The calculated off- and on-rate constants and the respective $K_D$ values are summarized below in Table 5.

As expected for MAb A9 (used as a control) a $K_D$ in the range of $4$-$6 \times 10^{-9}$ M was calculated for all allelic variants, demonstrating promiscuous binding of MAb A9 to all alleles of all forms. In contrast scFv 4-LS21 again proved to be highly specific for the CD16A isoform. The 4-LS21 scFv exhibited a $K_D$ in the region of $6 \times 10^{-8}$M for CD16A-Fc$^{48R/158V}$ and in the region of $4 \times 10^{-8}$ M for CD16A-Fc$^{48R/158F}$, indicating that 4-LS21 scFv binds to both allelic forms of CD16A with approximately equal affinity. In contrast 4-LS21 exhibited no binding to any of the allelic forms of CD16B.

TABLE 5

Data for the kinetics of binding of the scFv 4-LS21 and the MAb A9 to allelic variants of the CD16A and CD16B isoforms.

| scFv/Mab | Isoform & allelic variant | $k_{on}$ (M$^{-1}$s$^{-1}$) | $k_{off}$ (s$^{-1}$) | $K_D$ (M) ($k_{off}/k_{on}$) |
|---|---|---|---|---|
| 4-LS21 | CD16A | $5.54 \pm 1.97 \times 10^4$ | $3.42 \pm 0.14 \times 10^{-3}$ | $6.17 \times 10^{-8}$ |
| MAb A9 | Fc$^{48R/158V}$ | $7.86 \pm 2.16 \times 10^4$ | $4.06 \pm 1.0 \times 10^{-4}$ | $5.17 \times 10^{-9}$ |
| 4-LS21 | CD16A | $7.13 \pm 2.47 \times 10^4$ | $3.23 \pm 0.09 \times 10^{-3}$ | $4.53 \times 10^{-8}$ |
| MAb A9 | Fc$^{48R/158F}$ | $9.94 \pm 3.46 \times 10^4$ | $3.80 \pm 1.0 \times 10^{-4}$ | $3.82 \times 10^{-9}$ |
| 4-LS21 | CD16B Fc$^{SH}$ | | NO BINDING | |
| MAb A9 | | $7.79 \pm 1.90 \times 10^4$ | $5.28 \pm 4.93 \times 10^{-4}$ | $1.14 \times 10^{-8}$ |
| 4-LS21 | CD16B Fc$^{NA1}$ | | NO BINDING | |
| MAb A9 | | $7.72 \pm 4.86 \times 10^4$ | $4.87 \pm 4.72 \times 10^{-4}$ | $8.91 \times 10^{-9}$ |
| 4-LS21 | CD16B Fc$^{NA2}$ | | NO BINDING | |
| MAb A9 | | $7.57 \pm 2.90 \times 10^4$ | $4.78 \pm 4.23 \times 10^{-4}$ | $9.63 \times 10^{-9}$ |

Example 19

Construction of the Plasmid pSKK3 CD30×CD16$^{LS21}$ and Ab/(G$_2$S)$_3$ for Expression of TandAb Molecule in Bacteria The genes encoding the V$_H$ and V$_L$ variable domains of the anti-CD30 and anti-CD16A antibodies, were derived from the hybridoma HRS-3 or from the human scFv library, respectively, using the plasmids pHOG_scFv$_{(G2S)3}$ αCD30 (HRS-3) and pSKK2_scFv αCD16A (LS21).

The VH αCD16$^{LS21}$ was amplified by polymerase chain reaction with the primers P34, 5' CATCACGATATCA-GAACCACCGGAGCCGCCGCTACCACCT-GAGGACACGGTG ACCAGGGTTCCC 3' (SEQ ID NO 49), and P36, 5' CCGGCCATGGCGCAGGTC CAGCTGG-TACAGTCTGG 3'(SEQ ID NO 50), to introduce a nucleic acid sequence coding for the 9 amino acid linker (GlyGly-Ser)$_3$ (SEQ ID NO 51) at the 3' end of the PCR product The resulting PCR fragment was digested with the restriction enzymes Nco I/Eco RV and cloned into the Nco I/Eco RV pHOG_scFv$_{(G2S)3}$αCD30 (HRS-3) to create the hybrid plasmid pHOG_VHαCD16$^{LS21}$$_{(G2S)3}$VLαCD30$_{(G2S)3}$ VHαCD30.

The V$_L$ of the anti-CD16A antibody 4-LS21 was amplified by polymerase chain reaction with the primers P35, 5' GGT-CACCGTCTCCTCAGGTGGTAGCGGCGGCTC CGGTGGTTCTTCCTATGTGCTGACTCAGCCATCCTC 3' (SEQ ID NO 52), and P37, 5'CCTCTAGATTAGTGATG-GTGATGGTGATGGGATCCTAGGACGGTCAG CTTG-GTCCC 3' (SEQ ID NO 53), to introduce the nucleic sequence coding for the 9 amino acid linker (GlyGlySer)$_3$ (SEQ ID NO 52) at the 5' end of the PCR product. The resulting PCR fragment was digested with the restriction enzymes Bsm BI/Xba I and was cloned into the linearized Bsm BI/Xba I digested hybrid plasmid pHOG_VHαCD16$^{LS21}$$_{(G2S)3}$VLαCD30$_{(G2S)3}$VHαCD30 resulting in the plasmid pHOG CD30×CD16$^{LS21}$ TandAb/(G$_2$S)$_3$. This plasmid was cut by NcoI/XbaI and ligated into the NcoI/XbaI linearized plasmid pSKK3.

Example 20

Construction of the Plasmids pSKK3 CD19×CD16$^{LS21}$ TandAb/(G$_2$S)$_3$ for Expression of TandAb Molecules in Bacteria The genes encoding the V$_H$ and V$_L$ variable domains of the anti CD19 antibody was derived from the hybridoma HD37 using the plasmid pSKK3_scFv$_{(G2S)3}$ αCD19 (HD37).

Plasmid pSKK3_scFv$_{(G2S)3}$ αCD19 (HD37) was cut by Nco I/Bsm BI and the insert was purified on an agarose gel. The purified fragment was then digested with the restriction enzyme Eco RV. The Eco RV/Bsm BI digested fragment was cloned into the linearized Eco RV/Bsm BI plasmid pHOG CD30×CD16$^{LS21}$ TandAb/(G$_2$S)$_3$, resulting in the plasmid pHOG CD19×CD16$^{LS21}$ TandAb/(G$_2$S)$_3$. The plasmid pHOG CD19×CD16$^{LS21}$ TandAb/(G$_2$S)$_3$ was cut by NcoI/ XbaI and ligated in the NcoI/XbaI linearized plasmid pSKK3. The resulting plasmid is pSKK3 CD19×CD16A$^{LS21}$ TandAb/ (G$_2$S)$_3$ encoding the anti CD19× anti CD16A TandAb.

Example 21

Expression and Purification of the CD30×CD16$^{LS21}$ TandAb/(G$_2$S)$_3$ and CD19×CD16$^{LS21}$ TandAb/(G$_2$S)$_3$ Molecules in Bacteria Samples of *E. coli* K12 strain RV308 (Maurer et al., 1980, J. Mol. Biol. 139:147-161) transformed with the expression plasmids pSKK3 CD30×CD16$^{LS21}$ TandAb/(G$_2$S)$_3$ and pSKK3 CD19×CD16$^{LS21}$ TandAb/(G$_2$S)$_3$ were grown overnight in 2×YT medium with 50 μg/ml ampicillin and 100 mM glucose (2×YT$_{GA}$) at 28° C. Dilutions (1:50) of the overnight cultures in 2×YT$_{GA}$ were grown as flask cultures at 28° C. with shaking at 200 rpm. When cultures reached an OD$_{600}$ of 0.8, bacteria were sedimented by centrifugation at 9500 g for 15 min and 20° C. and resuspended in the same volume of fresh YTBS medium (2×YT containing 1 M sorbitol and 2.5 mM glycine betaine; Blacwell & Horgan, 1991, FEBS Letters 295:10-12) supplemented with 50 μg/ml ampicillin. IPTG was added to a final concentration of 0.2 mM and growth was continued at 21° C. for 18-20 h. Cells were harvested by centrifugation at 14000 g for 20 min at 4° C. To isolate soluble periplasmic proteins, the sedimented bacteria were resuspended in 5% of the initial volume of ice-cold 200 mM Tris-HCl, 20% sucrose, 1 mM EDTA, pH 8.0. After a 1 hour incubation on ice with occasional stirring, the spheroplasts were centrifuged at 14000 g for 60 min at 4° C. leaving the soluble periplasmic extract in the supernatant, and the spheroplasts plus the insoluble periplasmic material in the pellet. The periplasmic fractions were dialyzed against start buffer (50 mM Tris-HCl, 1 M NaCl, 50 mM Imidazole pH 7.0) at 4° C. The dialyzed solution containing recombinant product was centrifuged at 14000 g for 30 min at 4° C. Immobilized metal affinity chromatography (IMAC) was performed at 4° C. using a 1 ml column of Chelating Sepharose Fast Flow (GE Healthcare Biosciences, Freiburg, Germany) charged with Cu$^{2+}$ and equilibrated with 50 mM Tris-HCl, 1 M NaCl, pH 7.0 (start buffer). The sample was loaded by passing the sample over the column. It was then washed with twenty column volumes of start buffer followed by start buffer containing 50 mM imidazole until the absorbency (280 nm) of the effluent was minimal (about thirty column volumes). Absorbed material was eluted with 50 mM Tris-HCl, 1 M NaCl, 300 mM imidazole, pH 7.0. The eluted fractions containing the TandAb molecules were identified by Western-blot analysis using a Penta His™ Antibody BSA-free (Qiagen, Hilden, Germany) followed by a goat anti-mouse IgG labeled with horseradish peroxidase (Dianova, Hamburg, Germany).

The positive fractions were pooled and subjected to buffer exchange with 50 mM Imidazole, 50 mM NaCl (pH 6.0) or 50 mM MES, 50 mM NaCl (pH 5.5) using pre-packed PD-10 (GE Healthcare Biosciences, Freiburg, Germany) (CD30×CD16$^{LS21}$ TandAb/(G$_2$S)$_3$ and CD19×CD16$^{LS21}$ TandAb/(G$_2$S)$_3$, respectively). The turbidity of protein solution was cleared by centrifugation. The final purification was achieved by ion-exchange chromatography on a MonoS HR5/5 column (GE Healthcare Biosciences, Freiburg, Germany) in 50 mM Imidazole, 50 mM NaCl (pH 6.0) or 50 mM MES, 50 mM NaCl (pH 5.5) (CD30×CD16$^{LS21}$ TandAb/(G$_2$S)$_3$ and CD19×CD16$^{LS21}$ TandAb/(G$_2$S)$_3$, respectively), with a linear 0-1 M NaCl gradient. The eluted fractions containing the TandAb molecules were identified by reducing 15% SDS-PAGE followed by Coomassie staining. The positive fractions were collected and buffer exchanged with PBS containing 50 mM Imidazole and 10 mM Trehalose (pH 6.0 or 7.0) (CD30×CD16$^{LS21}$ TandAb/(G$_2$S)$_3$ and CD19×CD16$^{LS21}$ TandAb/(G$_2$S)$_3$, respectively) using pre-packed PD-10 (GE Healthcare Biosciences, Freiburg, Germany).

Example 22

Characterization of the CD30×CD16$^{LS21}$ Tandab/(G$_2$S)$_3$ and CD19×CD16$^{LS21}$ TandAb/(G$_2$S)$_3$ Molecules by Flow Cytometry To measure binding to CD16A, HEK-293 cells were transiently transfected using the calcium phosphate method with the pcDNA3-CD16A-zeta plasmid (Dr. O. Mandelboim, University of Jerusalem, Israel) and harvested 40 hours after transfection for flow cytometry as described in Example 7. The hairy cell leukemia cell line JOK-1 (Schwartz-Albiez R, Dorken B, Monner D A, Moldenhauer G, (1991) Int Immunol 3:623, a kind gift from Dr. G. Moldenhauer, DKFZ, Heidelberg) was used to determine binding to CD19. For testing reactivity with CD30, staining was performed with the human Hodgkin cell line L540CY (kindly provided by Dr. V. Diehl, University of Cologne, Germany; Kapp U, Wolf J, von Kalle C, Tawadros S, Rottgen A, Engert A, Fonatsch C, Stein H, Diehl V. (1992) Ann Oncol. September; 3 Suppl 4:21-3). Cell staining and analysis carried out essentially as described supra. All recombinant antibodies were detected by 10 μg/mL MAb anti-hexa His 13/45/31-2 (Dianova, Hamburg, Germany) followed by 15 μg/mL FITC-conjugated goat anti-mouse IgG (Dianova).

The flow cytometric analyses demonstrated strong binding of both the CD30×CD16$^{LS21}$ TandAb and the CD19×CD16$^{LS21}$ TandAb antibody to cells expressing the corresponding antigen. Both TandAb antibodies bound to CD16A-expressing cells with approximately equal affinity.

Example 23

Affinity Measurements

Determination of the K$_D$ values of the scFv 4-LS21 on the allelic variants 48R/158V and 48R/158F of the CD16A antigen revealed comparable K$_D$ values of about 5×10$^{-8}$M, as measured by surface plasmon resonance, indicating that both allelic variants are recognized with approximately the same affinity (see Example 12). This finding was confirmed with the 4-LS21 derived TandAb CD30×CD16$^{LS21}$, which was also shown to bind both allelic variants of CD16A with almost identical affinities. In comparison to the 4-LS21 scFv, an improvement in affinity of more than factor 10 was observed with the TandAb antibody due to increased avidity.

Example 24

Characterization of the CD30×CD16$^{LS21}$ TandAb/(G$_2$S)$_3$ and CD19×CD16$^{LS21}$ TandAb/(G$_2$S)$_3$ Molecules by Cytotoxicity Assays To determine whether the CD30×CD16$^{LS21}$ and CD19×CD16$^{LS21}$ TandAb antibodies could mediate in vitro cell cytotoxicity by recruiting NK cells to target cells and activation of the NK cells by crosslinking activatory receptors, non-radioactive cytotoxicity assays were performed essentially as described by T. Dreier et al. (2002, Int J Cancer 100:690-697). NK cells that were used as effector cells were enriched from PBMC as described previously. Purity and antigen expression of the enriched NK cells was checked by flow cytometry in each case (data not shown).

CD30$^+$ L540CY target cells or CD19$^+$ JOK-1 or Raji target cells were cultured in RPMI 1640 medium supplemented with 10% FCS, 2 mM L-glutamine and 100 IU/mL penicillin G sodium and 100 μg/mL streptomycin sulfate (herein referred to as RPMI medium; all components from Invitrogen). For the cytotoxicity assay cells were labeled with 10 μM calcein AM (Molecular Probes/Invitrogen) for 30 min in RPMI medium at 37° C. After gently washing the labeled cells were resuspended in RPMI medium to a density of 1×10$^5$/mL. 1×10$^4$ target cells were then seeded together with 1×10$^5$ enriched NK cells with either the CD30×CD16$^{LS21}$ TandAb or the CD19×CD16A$^{LS21}$ TandAb in individual wells of a round-bottom 96-well microtiter plate in a total volume of 200 µL/well. After centrifugation for 2 min at 200 g the assay was incubated for 3 hours at 37° C. in a humidified atmosphere with 5% $CO_2$. 15 minutes prior to the end of incubation 20 µL of 10% Triton X-100 in RPMI medium was added to the wells containing target cells only. 20 µL RPMI medium was added to all other wells. 100 µL of cell culture supernatant was harvested from each well after an additional centrifugation for 5 min at 500 g, and the fluorescence of the released calcein was measured at 520 nm using a fluorescence plate reader (Victor 3, Perkin Elmer). On the basis of the measured counts, the specific cell lysis was calculated according to the following formula: [fluorescence (sample)–fluorescence (spontaneous)]/[fluorescence (maximum)–fluorescence (spontaneous)]×100%. Fluorescence (spontaneous) represents the fluorescent counts from target cells in the absence of effector cells and antibodies and fluorescence (maximum) represents the total cell lysis induced by the addition of Triton X-100. Sigmoidal dose response curves were plotted using the Prism software (GraphPad Software) see FIG. 8.

The results demonstrate the specific lysis of target cells by TandAb-activated NK cells. In contrast, the CD19×CD16$^{LS21}$ TandAb did not mediate lysis of CD19-L540CY target cells, and vice-versa, the CD30×CD16$^{LS21}$ TandAb did not activate NK cells to kill CD30⁻ JOK-1 cells. In the absence of NK cells neither the CD30×CD16$^{LS21}$ TandAb nor the CD19×CD16$^{LS21}$ TandAb showed any cytotoxic activity against target cells.

The invention claimed is:

1. An isolated antibody or antigen-binding fragment thereof having specificity for FcγRIIIA but does not bind to FcγRIIIB, comprising:
   (a) a heavy chain CDR1 having the amino acid sequence set forth in SEQ ID NO:17; a heavy chain CDR2 having the amino acid sequence set forth in SEQ ID NO:18; a heavy chain CDR3 having the amino acid sequence set forth in SEQ ID NO:19; a light chain CDR1 having an amino acid sequence selected from the group consisting of SEQ ID NOs:20, 23, 26, 29, 33, and 34; a light chain CDR2 having an amino acid sequence selected from the group consisting of SEQ ID NOs:21, 24, 27, 30, 31, and 35; and a light chain CDR3 having an amino acid sequence selected from the group consisting of SEQ ID NOs:22, 25, 28, and 32; or
   (b) a light chain variable region having an amino acid sequence selected from the group consisting of SEQ ID NOs:10-16 and a heavy chain variable region; or
   (c) a heavy chain variable region having the amino acid sequence set forth in SEQ ID NO:9 and a light chain variable region, wherein the antigen-binding fragment is selected from the group consisting of Fv, Fab, di-Fab, Fab', F(ab')$_2$, scFv, and single chain antibody.

2. An isolated antibody or antigen-binding fragment thereof according to claim 1, wherein the antibody or antigen-binding fragment is fully human.

3. An isolated antibody or antigen-binding fragment thereof according to claim 1, which is capable of activating human cells expressing FcγRIIIA.

4. An isolated antibody or antigen-binding fragment thereof according to claim 3, which is capable of inducing NK-cell mediated cell killing.

5. An isolated antibody or antigen-binding fragment thereof according to claim 2, which inhibits activation of human cells expressing FcγRIIIA.

6. An isolated antibody or antigen-binding fragment thereof according to claim 1, wherein said antibody or antigen-binding fragment thereof comprises at least one additional antigen-binding fragment having specificity for at least one additional antigen.

7. An isolated antibody or antigen-binding fragment thereof according to claim 6, wherein the at least one additional antigen is a cell-surface antigen.

8. An isolated antibody or antigen-binding fragment thereof according to claim 7, wherein the cell-surface antigen is selected from the group consisting of CD19, CD20, CD30, the Laminin Receptor Precursor, EGFR1, EGFR2, EGFR3, Ep-CAM, PLAP, Thomsen-Friedenreich antigen, MUC-1, IL4-R alpha, IL13-R, IGFR, FcεRI and CD5.

9. An isolated antibody or antigen-binding fragment thereof according to claim 7, wherein the cell-surface antigen is CD19 or CD30.

10. An isolated antibody or antigen-binding fragment thereof according to claim 6, wherein the at least one additional antigen is from an infectious agent.

11. An isolated antibody or antigen-binding fragment thereof according to claim 10 wherein the infectious agent is a virus, a bacterium, a fungus, a mycoplasma, a parasite or a prion.

12. An isolated antibody or antigen-binding fragment thereof according to claim 1, wherein the antibody is selected from the group consisting of a chimeric antibody, a CDR-grafted antibody, a humanized antibody, and a fully human antibody.

13. An isolated antibody or antigen-binding fragment thereof according to claim 1, wherein the antibody or antigen-binding fragment thereof is a diabody or a TandAb.

14. An isolated antibody or antigen-binding fragment thereof according to claim 1, wherein said antibody or antigen-binding fragment thereof further comprises a functional domain.

15. An isolated antibody or antigen-binding fragment thereof according to claim 14, wherein the functional domain is an antibody Fc domain, an enzyme suitable for antibody-dependent enzyme prodrug therapy, a peptide capable of binding to Fc receptors, or a protein or peptide for increasing the serum half-life of the antibody or antigen-binding fragment thereof.

16. An isolated antibody or antigen-binding fragment thereof according to claim 1, wherein said antibody or antigen-binding fragment thereof is capable of binding to the FcγRIIIA$^{158F}$ allelic variant with approximately the same affinity with which it binds to the FcγRIIIA$^{158V}$ allelic variant.

17. An isolated antibody or antigen-binding fragment thereof according to claim 1, wherein the antibody or antigen-binding fragment thereof is conjugated to a labeling molecule or a toxin.

18. An isolated antibody or antigen-binding fragment thereof according to claim 17, wherein the labeling molecule is a radiolabel, a fluorescent label or a luminescent label.

19. A composition comprising an isolated antibody or antigen-binding fragment thereof according to claim 1 and at least one additional component.

20. A composition according to claim 19, wherein at least one additional component is a suitable pharmaceutical carrier, excipient, diluent stabilizer.

21. A kit comprising an isolated antibody or antigen-binding fragment thereof according to claim 1 and means for detecting the isolated antibody or antigen-binding fragment thereof when bound to FcγRIIIA.

* * * * *